United States Patent
Ilan et al.

(10) Patent No.: US 9,981,037 B2
(45) Date of Patent: May 29, 2018

(54) COMBINATION THERAPY OF BETA-GLYCOLIPIDS AND ANTIBODIES FOR THE TREATMENT OF IMMUNE-RELATED DISORDERS

(71) Applicants: HADASIT MEDICAL RESEARCH SERVICES AND DEVELOPMENT LTD., Jerusalem (IL); The Brigham and Women's Hospital, Inc., Boston, MA (US)

(72) Inventors: Yaron Ilan, Jerusalem (IL); Howard L. Weiner, Brookline, MA (US)

(73) Assignees: The Brigham and Women's Hospital, Inc., Boston, MA (US); Hadasit Medical Research Services and Development Ltd., Jerusalem (IL)

( * ) Notice: Subject to any disclaimer, the term of this patent is extended or adjusted under 35 U.S.C. 154(b) by 697 days.

(21) Appl. No.: 14/183,248

(22) Filed: Feb. 18, 2014

(65) Prior Publication Data
US 2014/0255420 A1   Sep. 11, 2014

Related U.S. Application Data

(63) Continuation of application No. 12/863,162, filed as application No. PCT/IL2009/000072 on Jan. 18, 2009, now abandoned.

(60) Provisional application No. 61/021,959, filed on Jan. 18, 2008.

(51) Int. Cl.
| | |
|---|---|
| A61K 39/395 | (2006.01) |
| A61K 31/7032 | (2006.01) |
| A61K 45/06 | (2006.01) |
| C07K 16/28 | (2006.01) |
| A61K 31/7028 | (2006.01) |

(52) U.S. Cl.
CPC ...... *A61K 39/3955* (2013.01); *A61K 31/7028* (2013.01); *A61K 31/7032* (2013.01); *A61K 45/06* (2013.01); *C07K 16/2809* (2013.01)

(58) Field of Classification Search
None
See application file for complete search history.

(56) References Cited

U.S. PATENT DOCUMENTS

| | | | |
|---|---|---|---|
| 6,143,297 A | 11/2000 | Bluestone | |
| 6,406,696 B1 | 6/2002 | Bluestone | |
| 2003/0153073 A1 | 8/2003 | Rogers et al. | |
| 2005/0196395 A1 | 9/2005 | Weiner et al. | |
| 2006/0198839 A1 | 9/2006 | Levetan | |
| 2007/0117778 A1 | 5/2007 | Ilan | |
| 2011/0200617 A1 | 8/2011 | Ilan et al. | |

FOREIGN PATENT DOCUMENTS

| | | |
|---|---|---|
| WO | WO03/009812 | 2/2003 |
| WO | WO05/048935 | 6/2005 |
| WO | WO 2006/002532 | 1/2006 |
| WO | WO07/060652 | 5/2007 |

OTHER PUBLICATIONS

Tolman et al. (Diabetes Care, vol. 30, No. 3, Mar. 2007, pp. 734-743).*
Roberts et al., Compr Physiol. Jan. 2013 ; 3(1): 1-119.*
Sasaki et al., J Biol Chem 278:27896-27902, 2003.*
Tagami et al. (J Biol Chem. Feb. 1, 2002;277(5):3085-92).*
Summers et al., Diabetes 54:591-602, 2005.*
Bauer et al., "Linkage between monokine production and regulation of the negative surface charge density of human monocytes," Immunol. Invest., 21(6):507-521 (Oct. 1992) Abstract Only.
Office Action issued in Canadian Application No. 2,712,404 dated Dec. 11, 2014.
Adorini et al., "Pathogenesis and immunotherapy of autoimmune diseases," Immunol Today, 18:209-211 (1997).
Akbari et al., "Antigen-specific regulatory T cells develop via the ICOS-ICOS-ligand pathway and inhibit allergen-induced airway hyperreactivity," Nat. Med., 8:1024-1032 (2002).
Alegre et al., "Effect of a single amino acid mutation on the activating and immunosuppressive properties of a "humanized" OKT3 monoclonal antibody," J. Immunol., 148(11):3461-8 (1992).
Ali et al., "Latency associated peptide has in vitro and in vivo immune effects independent of TGF-beta1," PLoS ONE, 3:e1914 (2008).
Baecher-Allan and Hafler, "Human regulatory T cells and their role in autoimmune disease," Immunological Reviews, 212:203-216 (2006).
Belkaid, "Regulatory T cells and infection: a dangerous necessity," Nature Reviews, 7:875-888 (2007).
Bisikirska et al., "TCR stimulation with modified anti-CD3 mAb expands CD8+ T cell population and induces CD8+CD25+ Tregs," The Journal of Clinical Investigation, 115:2904-2913 (2005).
Bluestone and Tang, "How do CD4+CD25+ regulatory T cells control autoimmunity?" Current Opinion In Immunology, 17:638-642 (2005).
Chatenoud and Bach, "Regulatory T cells in the control of autoimmune diabetes: the case of the NOD mouse," International Reviews Of Immunology, 24:247-267 (2005).
Chen et al., "Regulatory T cell clones induced by oral tolerance: suppression of autoimmune encephalomyelitis," Science, 265:1237-1240 (1994).

(Continued)

*Primary Examiner* — Zachary S Skelding
(74) *Attorney, Agent, or Firm* — Fish & Richardson P.C.

(57) ABSTRACT

The present invention relates to a combination therapy for the treatment of immune-related disorders. More particularly, the invention relates to oral or mucosal synergistic compositions combining beta-glycolipids, preferably, β-glycosphin-golipids with immunoglobulin molecules specific for at least one antigen derived from a component of the immune system, specifically an anti-CD3 antibody. The invention further provides methods kits and uses of the combined compositions of the invention for immune-modulation and thereby for the treatment of immune-related disorders. In a preferred embodiment, anti-CD3 antibody (OKT3) is orally administered in combination with β-glucosylceramide (also known as glycocerebroside) in an animal model of type 2 diabetes.

6 Claims, 24 Drawing Sheets

(56) References Cited

OTHER PUBLICATIONS

Chiba et al., "Human colonic intraepithelial and lamina proprial lymphocytes: cytotoxicity in vitro and the potential effects of the isolation method on their functional properties," Gut, 22:177-182 (1981).
Das et al., "A Shared and Unique Epitope(s) on Human Colon, Skin, and Biliary Epithelium Detected by a Monoclonal Antibody," Gastroenterology 98:464-69 (1990).
Dasgupta et al., "Circulating immunoglobulin G1 antibody in patients with ulcerative colitis against the colonic epithelial protein detected by a novel monoclonal antibody," Gut 35:1712-17 (1994).
Davignon et al., "Rapid T cell receptor modulation accompanies lack of in vitro mitogenic responsiveness of double negative T cells to anti-CD3 monoclonal antibody in MRL/Mp-lpr mice," J. Irnmunol., 141(6):1848-54 (1988).
Fantini et al., "Cutting edge: TGF-beta induces a regulatory phenotype in CD4+CD25− T cells through Foxp3 induction and downregulation of Smad7," J. Immunol., 172:5149-5153 (2004).
Faria and Weiner, "Oral tolerance and TGF-beta-producing cells," Inflammation & Allergy Drug Targets, 5:179-190 (2006).
Faria and Weiner, "Oral tolerance," Immunological Reviews, 206:232-259 (2005).
Faria and Weiner, "Oral tolerance: therapeutic implications for autoimmune diseases," Clin. Dev. Immunol., 13:143-157 (2006).
Frenken et al., "The role of antibody isotype in IFN-gamma and IL-2 production during anti-CD3-induced T cell proliferation," Transplantation, 51(4):881-7(1991).
Frey and Brauer, "Regulatory T cells: magic bullets for immunotherapy?" Arch. Immuno Ther. Exp. (Warsz), 54:33-43 (2006).
Gandhi et al., "Cutting Edge: Immature human dendritic cells express latency-associated peptide and inhibit T cell activation in a TGF-beta-dependent manner," J. Immunol., 178:4017-4021 (2007).
Herold et al., "Anti-CD3 monoclonal antibody in new-onset type 1 diabetes mellitus," N.E.J.M., 346(22) :1692-1698 (2002).
Hibi et al., "Circulating antibodies to the surface antigens on colon epithelial cells in ulcerative colitis," Clin. Exp. Immunol., 54:163-168 (1983).
Hong et al., "Induction of CD4+CD25+ regulatory T cells by copolymer-I through activation of transcription factor Foxp3," Proceedings of the National Academy of Sciences of the United States of America, 102:6449-6454 (2005).
Hyytiainen et al., "Latent TGF-beta binding proteins: extracellular matrix association and roles in TGF-beta activation," J. Critical Reviews in Clinical Laboratory Sciences, 41:233-264 (2004).
Ilan et al., "Alleviation of acute and chronic graft-versus-host disease in a murine model is associated with glucocerebroside-enhanced natural killer T lymphocyte plasticity," Transplantation, 83:458-467 (2007).
International Search Report issued in PCT/IL2009/000072 dated Dec. 1, 2009.
Ishikawa et al., "Inhibition of autoimmune diabetes by oral administration of anti-CD3 monoclonal antibody," Diabetes, 56:2103-2109 (2007).
Khalil, "TGF-beta: from latent to active," Microbes and infection, 1:1255-1263 (1999).
Kim et al., "NKT cells play critical roles in the induction of oral tolerance by inducing regulatory T cells producing IL-10 and transforming growth factor β, and by clonally deleting antigen-specific T cells," Immunology, 118:101-111 (2006).
Kotronen et al., "Fatty Liver: A Novel Component of the Metabolic Syndrome," Arterioscler. Thromb. Vasc. Biol., 28:27-38 (2008).
Lalazar et al., "Glycolipids as immune modulatory tools," Mini Reviews In Medicinal Chemistry, 6:1249-1253 (2006).
Lawrence, Latent-TGF-beta: an overview, Molecular and Cellular Biochemistry, 219:163-170 (2001).
Le and Chao, "Regulating regulatory T cells," N. Bone Marrow Transplant, 39:1-9 (2007).
Levy and llan, "Oral Immune Regulation: A New Mode of Therapy Against Chronic Viral Infections," Recent patents on anti-infective drug discovery, 2:217-221 (2007).
Lockhoff et al., "Glycolipids as immunomodulators syntheses and properties," Angewandte Chemie, 30(12):1611-1620 (1991).
Macia et al., "Impairment of dendritic cell functionality and steady-state number in obese mice," J. Immunol., 177:5997-6006 (2006).
Macpherson and Smith, "Mesenteric lymph nodes at the center of immune anatomy," The Journal Of Experimental Medicine, 203:497-500 (2006).
Madsen et al., "Interleukin 10 prevents cytokine-induced disruption of T84 monolayer barrier integrity and limits chloride secretion," Gastroenterology, 113:151-159 (1997).
Margalit et al., "Glucocerebroside treatment ameliorates ConA hepatitis by inhibition of NKT lymphocytes," American Journal Of Physiology, 289:G917-925 (2005).
Marie et al., "TGF-beta1 maintains suppressor function and Foxp3 expression in CD4+CD25+ regulatory T cells," The Journal Of Experimental Medicine, 201:1061-1067 (2005).
Milling et al., "Regulation of intestinal immunity: effects of the oral adjuvant *Escherichia coli* heat-labile enterotoxin on migrating dendritic cells," European Journal Of Immunology, 37:87-99 (2007).
Miyamoto et al., "The ICOS molecule plays a crucial role in the development of mucosal tolerance," J. Immunol., 175:7341-7347 (2005).
Mizoguchi et al., "Cytokine imbalance and autoantibody production in T cell receptor-alpha mutant mice with inflammatory bowel disease," J. Exp. Med., 183:847-856, (1996).
Neurath et al., "Experimental granulomatous colitis in mice is abrogated by induction of TGF-beta-mediated oral tolerance," J. Exp. Med., 183:2605-2616 (1996).
Nicolls et al., "Induction of long-term specific tolerance to allografts in rats by therapy with an anti-CD3-like monoclonal antibody," Transplantation, 55:459-468 (1993).
Niess and Reinecker, "Dendritic cells: the commanders-in-chief of mucosal immune defenses," Curro Opin. Gastroenterol., 22:354-360 (2006).
Nikoopour et al., "Therapeutic benefits of regulating inflammation in autoimmunity," Inflamm. Allergy Drug Targets, 7:203-210 (2008).
Ochi et al., "Oral CD3-specific antibody suppresses autoimmune encephalomyelitis by inducing CD4+ CD25− LAP+ T cells," Nat. Med., 12:627-635 (2006).
Oida et al., "CD4+CD25− T cells that express latency-associated peptide on the surface suppress CD4+CD45RBhigh-induced colitis by a TGF-beta-dependent mechanism," J. Immunol, 170:2516-2522 (2003).
Oklu and Hesketh, "The latent transforming growth factor beta binding protein (LTBP) family," The Biochemical Journal, 352(3):601-610 (2000).
Peng et al., "TGF-beta regulates in vivo expansion of Foxp3-expressing CD4+CD25+ regulatory T cells responsible for protection against diabetes," Proceedings of the National Academy of Sciences of the United States of America, 101:4572-4577 (2004).
Piccirillo and Shevach, "Naturally-occurring CD4+CD25+ immunoregulatory T cells: central players in the arena of peripheral tolerance," Semin. Immunol , 16:81-88 (2004).
Raedler et al., "Elevated numbers of peripheral T cells in inflammatory bowel diseases displaying T9 antigen and Fc alpha receptors," Clin. Exp. Immunol., 60:518-526 (1985).
Randolph and Fathman, "Cd4+Cd25+ regulatory T cells and their therapeutic potential," Annual Review of Medicine, 57:381-402 (2006).
Safadi et al., "Amelioration of hepatic fibrosis via beta-glucosylceramide-mediated immune modulation is associated with altered CD8 and NKT lymphocyte distribution," International Immunology, 19(8):1021-1029 (2007).
Safadi et al., "RETRACTION of: Amelioration of hepatic fibrosis via betaglucosylceramide-mediated immune modulation is associated with altered CD8 and NKT lymphocyte distribution," International Immunology, 23(7):465 (2011).

(56) References Cited

OTHER PUBLICATIONS

Saharinen et al. "Latent transforming growth factor-beta binding proteins (LTBPs)—structural extracellular matrix proteins for targeting TGF-beta action," Cytokine and Growth Factor Reviews, 10:99-117 (1999).
Shoelson et al., "Inflammation and insulin resistance," The Journal of Clinical Investigation, 116:1793-1801 (2006).
Strober et al., "Reciprocal IFN-gamma and TGF-beta responses regulate the occurrence of mucosal inflammation," Immunol Today, 18:61-64. (1997).
Strom et al., Therapeutic Immunology, edited by Austen et al., Blackwell Science, Cambridge, MA, pp. 451-456 (1996).
Stuenkel et al., "Synthetic glycolipids with immunopotentiating activity on humoral immunity evaluation in vivo," Progress In Leukocyte Biology, 9:575-579 (1988).
Takahashi et al., "Isolation and Characterization of a colonic autoantigen Specifically Recognized by Colon Tissue-bound Immunoglobulin G from Idiopathic Ulcerative Colitis," J. Clin. Invest., 76:311-318 (1985).
Tanaka et al., "Characterization of a CD3-like rat T cell surface antigen recognized by a monoclonal antibody," J. Immunol, 142:2791-2795 (1989).
Tang and Bluestone, "Regulatory T-cell physiology and application to treat autoimmunity," Immunological Reviews, 212: 217-237 (2006).
Trop et al., "Role of NK1.1+ and AsGm-1+ cells in oral immunoregulation of experimental colitis," Inflammatory Bowel Diseases, 9:75-86 (2003).
Van Deventer et al., "Multiple Doses of Intravenous Interleukin 10 in Steroid-Refractory Crohn's Disease," Gastroenterology, 113:383-389 (1997).
Verma et al., "Structure and function of latency-associated nuclear antigen," Current Topics in Microbiology and Immunology, 312:101-136 (2007).
von Boehmer, "Oral tolerance: is it all retinoic acid?" The Journal Of Experimental Medicine, 204:1737-1739 (2007).
von Herrath et al., "Type 1 diabetes as a relapsing-remitting disease?" Nature Reviews, 7:988-994 (2007).
Wahl et al., "TGF-beta: A mobile purveyor of immune privilege," Immunological Reviews, 213:213-227 (2006).
Walther et al., "Upregulation of TGF-beta, FOXP3, and CD4+CD25+ regulatory T cells correlates with more rapid parasite growth in human malaria infection," Immunity, 23:287-296 (2005).
Weiner et al., "Oral tolerance: immune mechanisms and treatment of autoimmune diseases," Immunol. Today, 18: 335-343 (1997).
Worbs et al., "Oral tolerance originates in the intestinal immune system and relies on antigen carriage by dendritic cells," The Journal Of Experimental Medicine, 203:519-527 (2006).
Yang et al., "Absence of integrin-mediated TGFbeta1 activation in vivo recapitulates the phenotype of TGFbeta1-null mice," The Journal Of Cell Biology, 176:787-793 (2007).
Yeh et al., "Tai chi chuan exercise decreases A1C levels along with increase of regulatory T-cells and decrease of cytotoxic T-cell population in type 2 diabetic patients," Diabetes Care, 30:716-718 (2007).
Young et al., "The tryptophan-rich motifs of the thrombospondin type 1 repeats bind VLAL motifs in the latent transforming growth factor-beta complex," The Journal Of Biological Chemistry, 279:47633-47642 (2004).
Zeissig et al., "Role of NKT cells in the digestive system. III. Role of NKT cells in intestinal immunity," American Journal of Physiology, 293:G1101-1105 (2007).
Zigmond et al., "Beta-glucosylceramide: a novel method for enhancement of natural killer T lymphoycte plasticity in murine models of immune-mediated disorders," Gut, 56:82-89 (2007).
Zigmond et al., Hepatology, 44(4 Suppl. 1):657A-658A (Oct. 2006).
Zou, "Regulatory T cells, tumour immunity and immunotherapy," Nat. Rev. Immunol., 6:295-307 (2006).
Belghith et al., "TGF-beta-dependent mechanisms mediate restoration of self-tolerance induced by antibodies to CD3 in overt autoimmune diabetes," Nat Med., 9(9):1202-1208. Epub Aug. 24, 2003.
Chatenoud et al., "CD3-specific antibody-induced active tolerance: from bench to bedside," Nat Rev Immunol., 3(2):123-132, Feb. 2003.
van Exel et al., "Low production capacity of interleukin-10 associates with the metabolic syndrome and type 2 diabetes : the Leiden 85-Plus Study," Diabetes, 51(4):1088-1092, Apr. 2002.

\* cited by examiner

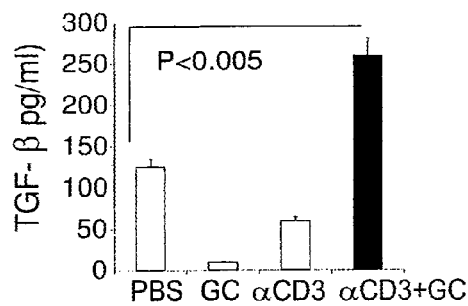
Fig. 4A
Fig. 4B
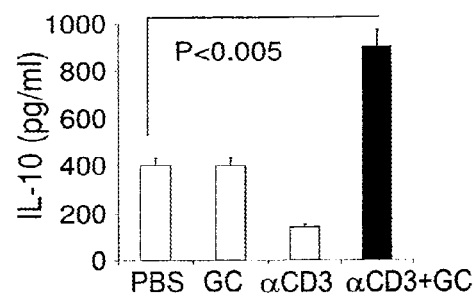
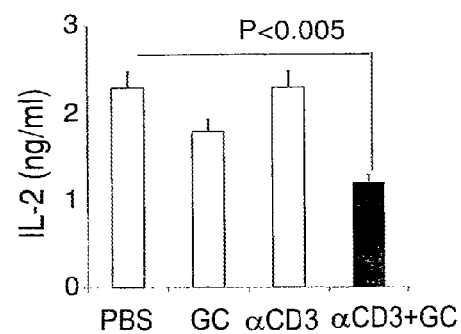
Fig. 4C
Fig. 4D
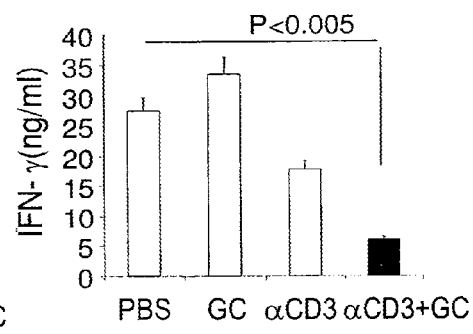
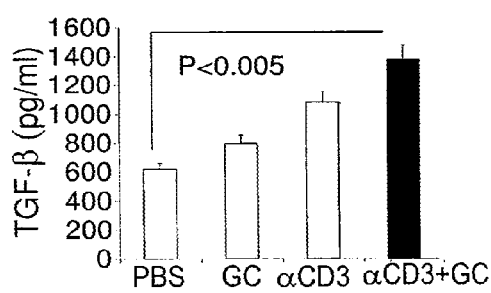
Fig. 4E
Fig. 4F
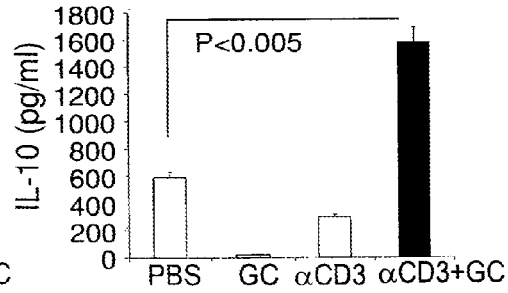

PBS anti-CD3+GC

COMBINATION THERAPY OF BETA-GLYCOLIPIDS AND ANTIBODIES FOR THE TREATMENT OF IMMUNE-RELATED DISORDERS

FIELD OF THE INVENTION

The present invention relates to a combination therapy for treating immune-related disorders. More particularly, the invention relates to oral or mucosal compositions combining beta-glycolipids, preferably, beta-glycosphingolipids with immunoglobulin molecules, specifically, anti CD3 antibodies. The invention further provides methods, kits using the combined compositions for immuno-modulation and thereby for the treatment of immune-related disorders.

BACKGROUND OF THE INVENTION

Throughout this application, various publications are referred to. These publications, and references included therein, are incorporated herein in their entirety.

In many instances, combination therapies employing two or more therapeutic compounds are required to adequately address different medical conditions and/or effects of a certain disorder under treatment. Thus, β-glycolipides which were previously shown by part of the inventors as having an immuno-modulatory effect may be employed together with various other therapeutic agents, and specifically with antibodies recognizing antigens derived from an immune-system component, to address a broader spectrum of immune-related disorders. Combining at least two immunomodulatory medications safely and effectively improves overall beneficial effect on different immune-related abnormalities.

Immune therapy involves the exposure of components of the immune system to various elements (cytokines, disease, associated antigens and natural metabolites) to combat disease processes in which a dysregulated immune response is thought to play a role. Immune dysregulation is thought to play a major part in the pathogenesis or disease course of a great number of disease processes, including various neoplastic, inflammatory, autoimmune, infectious and genetic entities.

These disorders can be perceived as a dysbalance between pro-inflammatory (Th1) and anti-inflammatory (Th2) cytokines. Both CD4 and CD8 lymphocytes can be typed as either Th1 cells that produce IL-2 and IFNγ, or Th2 cells that produce IL-4, and IL-10. The way the immune system responds to foreign and self antigens, is the result of a balance between the two subtypes of responses [Weiner, H. L., et al. Immunol. Today 18: 335-343 (1997); Adorini, L., et al. Immunol. Today 18:209-211 (1997)]. A Th1 type response is involved in the pathogenesis of several autoimmune and chronic inflammatory disorders such as IBD [Adorini, L., et al. (1997) ibid.; Mizoguchi, A., et al. J. Exp. Med. 183:847-856, (1996)]. Thus experimental autoimmune diseases in humans can be perceived as a dysbalance between pro-inflammatory Th1-type and anti-inflammatory Th2-type cytokines. It has been previously shown, in both animals and humans, that anti-inflammatory cytokines such as IL-10 can down regulate the pro-inflammatory effects of Th1-mediated cytokines, thereby alleviating immune-mediated disorders [Mizoguchi, A., et al. (1996) ibid.; Madsen, K. L., et al. Gastroenterology 113:151-159 (1997); Van Deventer Sander, J., et al. Gastroenterology 113:383-389 (1997)].

In the past few years it has been become increasingly clear that T cells capable of actively suppressing immune responses are thought to be in part responsible for the maintenance of peripheral self tolerance. In healthy rodents and humans, $CD4^+$ T cells constitutively expressing the interleukin IL-2 receptor alpha-chain (CD25) are able to exert such suppressive function in vitro and in vivo [Piccirillo, C. A. and Shevach, E. M. Semin. Immunol. 16:81-88 (2004)]. Immunoregulatory cytokines such as IL-10 or TGF-β may be critical for the suppressive effect of these cells. Regulatory T cells have potential role in human autoimmune or chronic inflammatory diseases and can be used for diagnostic or therapeutic purposes [Frey, O. and Brauer, R. Arch. Immuno. Ther. Exp. (Warsz) 54:33-43 (2006)].

Regulatory T cells (Tregs) are a specialized subpopulation of T cells that act to suppress activation of other immune cells and thereby maintain immune system homeostasis, self-tolerance as well as control excessive response to foreign antigens [Le, N. T. and Chao, N. Bone Marrow Transplant 39:1-9 (2007)]. The two best-characterized subsets are the naturally arising, intrathymic-generated Tregs. (natural Tregs.) and the peripherally generated, inducible Tregs. (inducible Tregs.) [Le (2007) ibid.].

Strategies for therapeutic targeting of regulatory T cells and the effect of regulatory T cells on current immunotherapeutic and vaccine regimens have been recently described [Zou, W. Nat. Rev. Immunol. 6:295-307 (2006)].

Self/non-self discrimination is a complex process that involves maintaining tolerance to auto-antigens while preserving the potential to generate an effective humoral and cellular immune responses against invading pathogens. CD4 (+)CD25(+) Treg, have emerged as a dominant T cell population capable of mediating peripheral tolerance to autoantigens, but whose functions have now been extended to regulation of T cell responses directed to foreign antigens [Piccirillo (2004) ibid.].

Autoimmunity results from the dysregulation of the immune system leading to tissue damage. Th1 and Th17 cells are known to be cellular mediators of inflammation in autoimmune diseases. The specific cytokine milieu within the site of inflammation or within secondary lymphatic tissues is important during the priming and effector phases of T cell response. Dendritic cell subsets can change the balance between major players in autoimmunity, namely Th1, Th17 and regulatory T cells. Th17 cells, once thought to only act as pathogenic effectors through production of IL-17, have been shown to have regulatory properties as well with co-production of the anti-inflammatory cytokine IL-10 by a subset now referred to as regulatory Th17 cells [Nikoopour, E. et al. Inflamm. Allergy Drug Targets 7:203-210 (2008)]. IL-17 is important in the induction of autoimmune diseases such as experimental autoimmune encephalomyelitis (EAE) and inflammatory bowel disease (IBD).

Promotion of regulatory T cells is important for the treatment of immune mediated disorders, and for infectious, inflammatory, malignant or any disease in which the immune system plays a deleterious role or have a role in their pathogenesis.

WO 2007/060652, which is a previous publication by part of the present inventors, discloses the use of beta-glycolipides as an immuno-modulatory compound in the treatment of immune-related disorders. More specifically, this publication showed that a particular mixture of β-lactosyl-ceramide with β-glucosylceramide is a powerful immuno-modulating medicament useful in the treatment of immune-related disorders.

WO 2005/048935, which is another publication by part of the present inventors, describes the immunomodulatory effect of an anti CD3 antibody on autoimmune disorders. More specifically, this publication shows that oral and mucosal administration of anti-CD3 antibody suppresses experimental allergic encephalomyelitis (EAE, an animal model of multiple sclerosis (MS), delays allograft rejection in a dose-dependent fashion, reduces the severity of arthritis and prevents the onset of diabetes in NOD mouse model.

There is growing evidence that there may be a link between inflammation and the pathogenesis of Type 2 diabetes [Shoelson, S. E. et al. The Journal of clinical investigation 116:1793-1801 (2006)]. This evolving concept which suggests that insulin resistance and type 2 diabetes may have an immune component provides a new avenue to investigate immunotherapeutic approaches to both understand the pathogenesis of type 2 diabetes and to develop new treatments for the disease. Regulatory T cells have been implicated as playing in a key role in classic autoimmune diseases in which deficiencies have been identified and strategies to induce Tregs for treatment of these diseases are being actively pursued [Baecher-Allan, C. and Hafler, D. A. Immunological reviews 212:203-216 (2006); Belkaid, Y. Nature reviews 7:875-888 (2007); Tang, Q. and Bluestone, J. A. Immunological reviews 212: 217-237 (2006)]. Although Tregs have been extensively investigated in animals models and human subjects with type 1 diabetes [Tang, Q. and Bluestone, J. A. Immunological reviews 212: 217-237 (2006); Bluestone, J. A. and Tang, Q. Current opinion in immunology 17:638-642 (2005); Chatenoud, L. and Bach, J. F. International reviews of immunology 24:247-267 (2005); Randolph, D. A. and Fathman, Annual review of medicine 57:381-402 (2006); von Herrath, M. et al. Nature reviews 7:988-994 (2007)] their potential role in type 2 diabetes has not been well explored and is not fully understood [Yeh, S. H. et al. Diabetes care 30:716-718 (2007)].

The present invention now shows a surprising and clear synergistic effect of β-glycolipides, specifically, β-glucosylceramide (GC), and anti-CD3 antibody on immune-related disorders. More specifically, the invention demonstrates that the induction of regulatory T cells by oral administration of a combination of anti-CD3 plus β-glycosphingolipid alleviates the metabolic syndrome in ob/ob mice in a TGF-β dependent manner. More particularly, a marked decrease in pancreatic islet cell hyperplasia and decreased accumulation of fat in the liver accompanied by lower blood glucose and liver enzymes was demonstrated in animals treated with the combined composition. Moreover, the invention shows that the combined composition of GC and anti-CD3 leads to elevation in serum levels of insulin. These effects were mediated by the induction of CD4+LAP+ Tregs by oral anti-CD3 plus GC. Adoptive transfer of CD4+LAP+ Tregs ameliorated the metabolic changes and pathologic abnormalities in a TGF-β dependent fashion. The results of the present invention suggest that immune abnormalities may play an important role in type 2 diabetes and identify a unique immunologic approach for treatment by induction of regulatory T cells.

Thus, a combination of these two compounds, specifically, GC, and anti-CD3 antibody promote different types of regulatory cells in the bowel or systemically. Additionally, this combination activates antigen presentation by promoting APC, including but not limited to dendritic cells. Both compounds in a synergistic combination alter the secretion of chemokines or cytokines that may together enhance the function of any component of the immune system. The invention further shows a remarkable anti-inflammatory effect of the combined composition on a tissue related to the treated disorder, e.g., fat tissue. More particularly, using the ob/ob model, the combined composition of the invention demonstrated suppression of pro-inflammatory cytokine expression, followed by elevation in anti-inflammatory cytokines production in adipocytes. Furthermore, the combined composition of the invention led to a marked decreased inflammatory cell infiltration to the fat tissue of the treated subject.

Overall, these two compounds in combination exert a synergistic effect and enhance the cross talk between different regulatory T cells, effector cells, and other component of the immune system.

Without being bound by any theory, the inventors speculate and show that the combination of these two compounds, antibody and glycosphingolipid, lead to this synergistic effect by activation of antigen presenting cells, different type of T regulatory cells, adipocytes cells or any other immune-cells. Such activation induces the secretion of different cytokines or chemokines and thereby promotes specific cell-cell interaction and induction of specific signal transduction pathways, leading to modulation of the Th1-Th2, Th3 cell balance in each immune-mediated disorder.

The invention therefore provides an oral or mucosal immuno-modulatory composition combining β-glycolipides, specifically, GC, and antibodies specific for CD3 for treating immune-related disorders.

Another object of the invention is to provide methods and kits for treating immune-related disorders using the combined composition of the invention.

These and other objects of the invention will become clearer as the description proceeds.

SUMMARY OF THE INVENTION

In a first aspect the invention relates to a composition comprising a combination of at least one natural or synthetic beta-glycolipid and at least one immunoglobulin molecule specific for an epitope derived from a component of the immune system or any functional fragments thereof. The composition of the invention may optionally further comprises at least one pharmaceutically acceptable carrier, diluent, excipient and/or additive.

A specifically preferred immunomodulatory composition may be a composition combining beta-glucosylceramide (GC) and an anti-CD3 antibody.

According to another embodiment, the combined composition of the invention is an immuno-modulatory composition.

The invention further provides a pharmaceutical composition for treating, preventing, ameliorating or delaying the onset of an immune-related disorder in a subject in need thereof. The pharmaceutical composition comprises as an active ingredient a therapeutically effective amount of a combination of at least one natural or synthetic beta-glycolipid and at least one immunoglobulin molecule specific for an epitope derived from a component of the immune system or any functional fragments thereof, and optionally at least one additional therapeutic agent, with a pharmaceutically acceptable carrier.

Still further the invention provides an oral or mucosal pharmaceutical composition made by combining a therapeutically effective amount of at least one natural or synthetic beta-glycolipid and at least one immunoglobulin molecule specific for an epitope derived from a component of the immune system or any functional fragments thereof, and optionally at least one additional therapeutic agent, with a pharmaceutically acceptable carrier.

Another aspect of the invention relates to a method of treating, preventing, ameliorating or delaying the onset of an immune-related disorder in a subject in need thereof. According to one specifically preferred embodiment, the method of the invention comprises the step of administering to the treated subject a therapeutically effective amount of at least one of:

(a) a combination of at least one natural or synthetic beta-glycolipid and at least one immunoglobulin molecule specific for an epitope derived from a component of the immune system or any functional fragments thereof;

(b) an immune-cell treated with (a) or with a composition comprising the same;

(c) an immune-cell obtained from a subject treated with any one of (a), (b) or with a composition comprising the same; and (d) a composition comprising any one of (a), (b), (c), or any combination or mixture thereof, said composition optionally further comprises at least one pharmaceutically acceptable carrier, diluent, excipient and/or additive.

According to a further aspect, the invention provides the use of a therapeutically effective amount of a combination of at least one natural or synthetic beta-glycolipid and at least one immunoglobulin molecule specific for an epitope derived from a component of the immune system or any functional fragments thereof, in the preparation of a medicament for the treatment of an immune-related disorder.

Another aspect of the invention relates to a pharmaceutical unit dosage form comprising a combination of at least one natural or synthetic β-glycolipid and at least one immunoglobulin molecule specific for an epitope derived from a component of the immune system or any functional fragments thereof, and a pharmaceutically acceptable carrier or diluent.

According to another aspect, the invention relates to a kit for achieving a therapeutic effect in a subject suffering from an immune-related disorder. The kit of the invention comprises: (a) at least one natural or synthetic beta-glycolipid or a pharmaceutically acceptable derivative thereof and a pharmaceutically acceptable carrier or diluent in a first unit dosage form; (b) at least one immunoglobulin molecule specific for an epitope derived from a component of the immune system or any functional fragments thereof, and a pharmaceutically acceptable carrier or diluent in a second unit dosage form; and (c) container means for containing said first and second dosage forms.

These and other aspects of the invention will become apparent by the hand of the following Figures.

BRIEF DESCRIPTION OF THE FIGURES

FIG. 2B. shows GTT (glucose tolerance test) of mice treated with PBS (clear bar) or the combination of anti-CD3 (5 μg) plus GC (100 μg). Blood glucose levels were measured at different times using a glucometer. Abbreviations: ser. (serum), bl. (blood), lev. (levels), T (time), min. (minutes).

FIG. 3B. presents quantification of pancreatic islet cell area (10 islets per field).

FIG. 3C. Quantification of fat area in liver (pixels×1000/field). All slides were read in a random fashion, blinded to treatment group. Abbreviations: Pan. (pancreas), Liv. (liver), Mus. (Muscle), Isl. (islet), ce. (cell), ar. (area), fie. (field), Fa. (fat), Oi. R. (il red), Pix. (pixels).

FIG. 4A-4F. Production of TGF-β and IL-10 in the mesenteric lymph node, pancreas, and gut following oral combination of anti-CD3 plus GC TGF-β (FIG. 4A) IL-10 (FIG. 4B), IL-2 (FIG. 4C) and IFN-γ (FIG. 4D) levels were measured in MLN cells following in vitro anti-CD3 stimulation (1 ug/ml) 5 days after the last treatment.

TGF-β and IL-10 content was measured in supernatants from homogenized pancreas (FIG. 4E) and gut (FIG. 4F) 10 days after the last treatment.

Figure 5A:
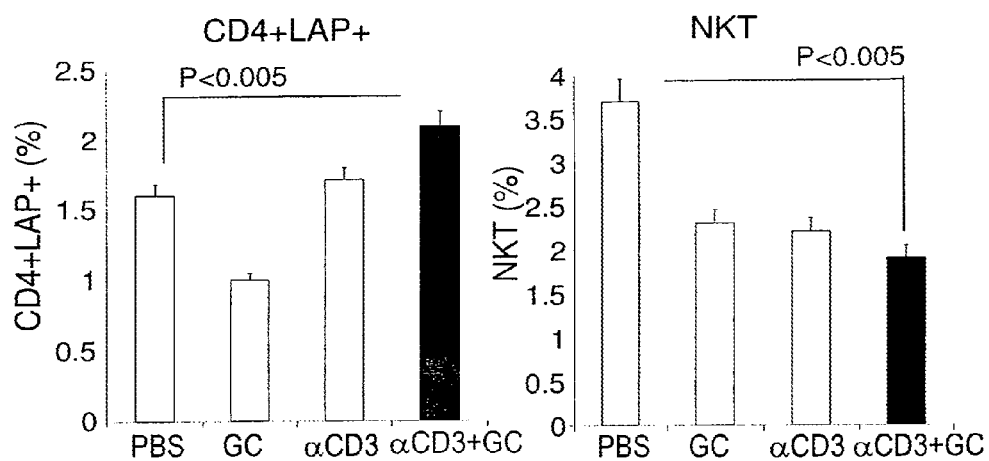
Figure 5B:
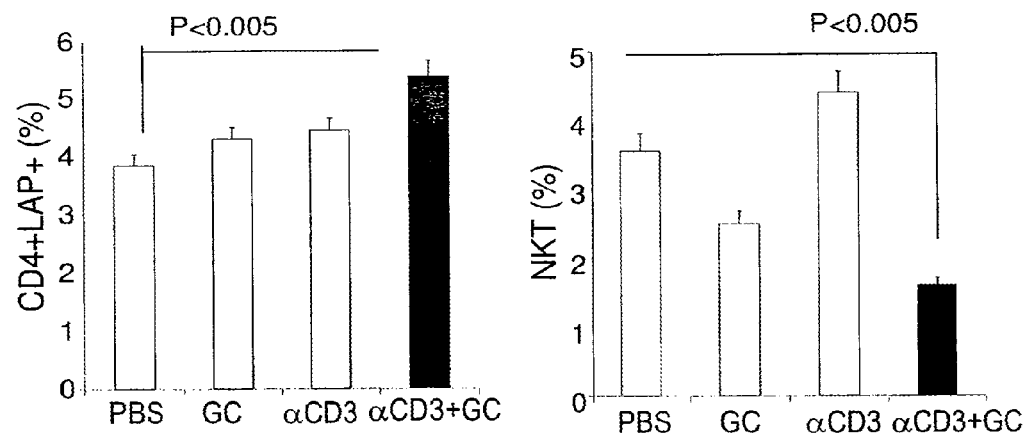
Figure 5C:
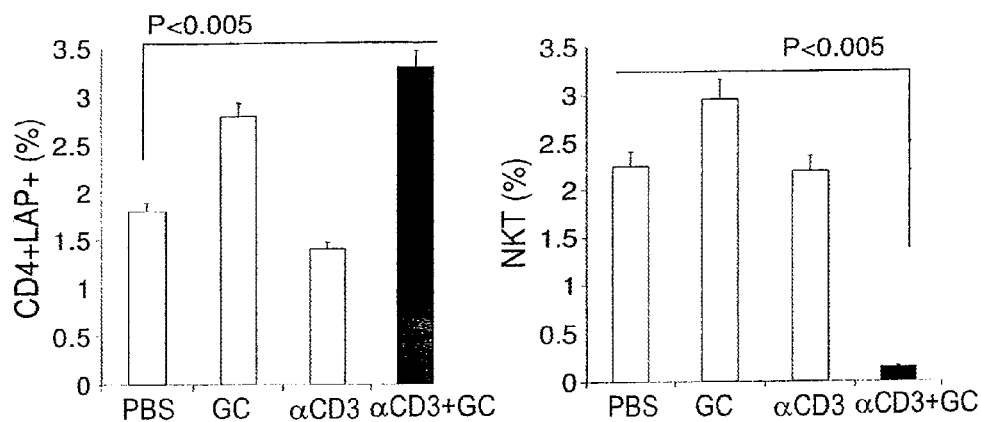

FIG. 5A-5C. Oral anti-CD3 plus GC increases CD4+ LAP+ cells and decreases NKT cells in MLN, spleen and blood The percentage of CD4+LAP+, and NKT cells were measured by FACS analysis in MLN (FIG. 5A), spleen (FIG. 5B) and blood (FIG. 5C) of ob/ob mice fed with a combination of anti-CD3 plus GC, anti-CD3, GC or PBS 5 days after the last treatment.

FIG. 6A-6G. Adoptive transfer of CD4+LAP+ T cells ameliorates metabolic abnormalities and decreases IL-17, IFN-γ and IL-6 in ob/ob mice in a TGF-β dependent fashion CD4+LAP+ cells ($40\times10^3$) harvested from ob/ob mice fed with the combination of anti-CD3 plus GC were adoptively transferred into naive ob/ob mice to measure the effect of CD4+LAP+ cells on the metabolic syndrome (FIGS. 6A, 6B, 6C and 6D) and inflammatory cytokine patterns (FIGS. 6E, 6F and 6G) of the recipients. Abbreviations: Glu. (glucose), TG (triglycerides).

FIG. 7A-7F. Dendritic cells from the MLN of ob/ob mice fed anti-CD3 plus GC have increased expression of TGF-β and IL-10 and suppress IL-2, IL-6, and IL-17 secretion CD11C+ DCs were isolated from MLN 3 days after feeding using anti-CD11c magnetic microbeads and TGF-β and IL-10 (FIGS. 7A, 7B, respectively) expression measured by RT PCR. Values are expressed as fold increase or decrease relative to the expression of GAPDH.

FIGS. 7C-7F. DCs isolated from the MLN of ob/ob mice fed PBS, or anti-CD3 antibody plus GC were tested for their ability to induce proliferation and secretion of IL-2, IL-6 or IL-17 (7C, 7D, 7E and 7F) by CD4 T cells harvested from PBS or combination of anti-CD3 plus GC fed mice. T cells were stimulated with 1 ug/ml anti-CD3 in vitro. Abbreviations: rel. (relative) Exp. (expression) Prol. (proliferation), ce. (cells)

Figure 8:
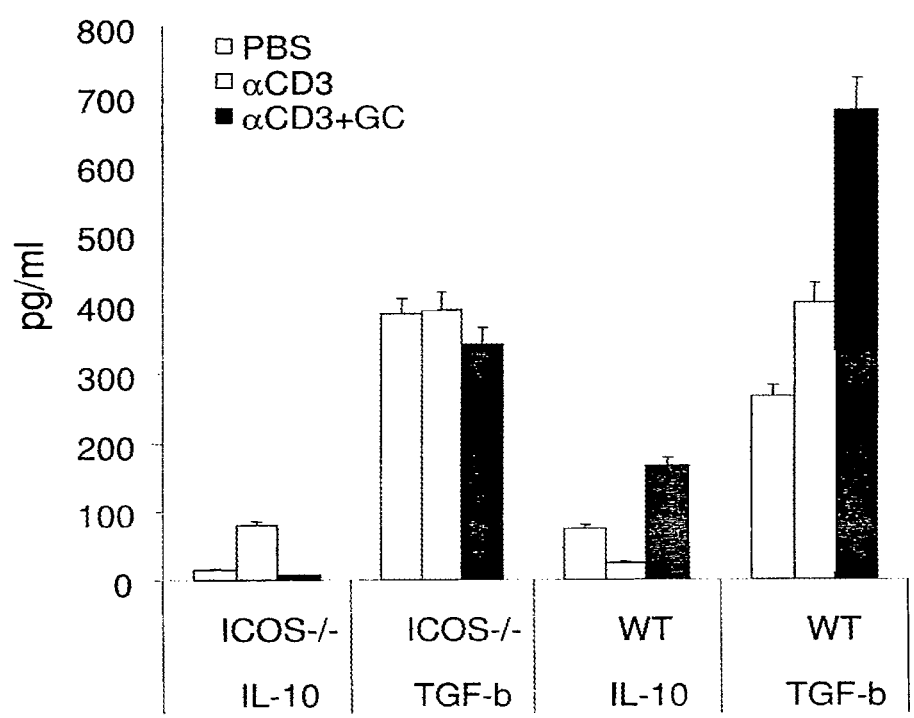

FIG. 8. Increased secretion of TGF-β and IL-10 by T cells following oral combination of anti-CD3 plus GC is ICOS dependent IL-10 and TGF-β secretion profile of lymphocytes from C57BL/6 (B6) ICOS−/− or wild type (WT) mice fed with anti-CD3 plus GC and stimulated in vitro with 1 μg/ml anti-CD3. Lymphocytes from mice fed with anti-CD3 plus GC, PBS or anti-CD3 were stimulated in vitro with anti CD3 (1 ug/ml) and secretion of TGF-β and IL-10 measured.

Figure 9:
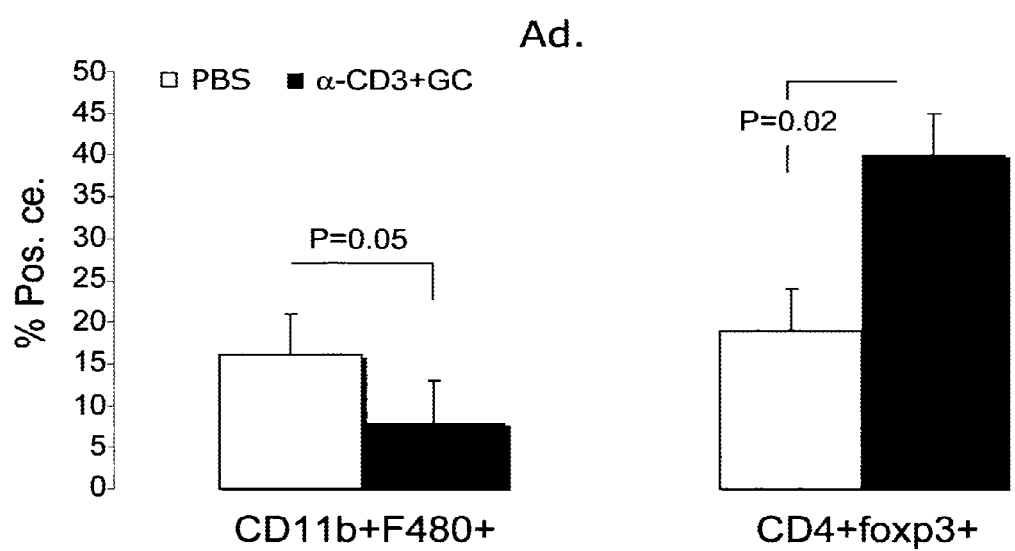

FIG. 9. Oral anti-CD3 and GC down-regulates macrophages and elevates foxp3+ regulatory T cells in fat of ob/ob mice Figure shows the percentage of macrophages (CD11b+ F4/80+ double positive cells) and regulatory T cells (CD4+ foxp3, double positive cells), in adipocytes isolated from white fat near or surrounding mesenteric lymph nodes collected from ob/ob mice treated either with PBS (clear bar) or with the oral combination of anti-CD3 (5 μg) plus. GC (100 μg) solution for 5 consecutive days. Abbreviations: Ad. (adipocyte), pos. (positive), ce. (cell).

Figure 10A:
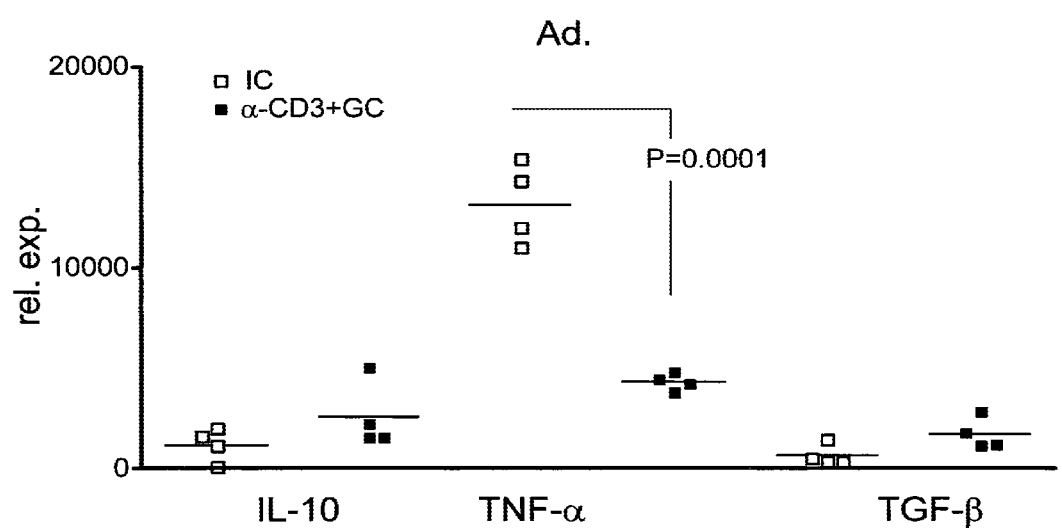

FIG. 10. Suppression of inflammatory cytokine production by adipocytes following oral combination of anti-CD3 and GC FIG. 10A. shows relative expression by real time RTPCR, of anti-inflammatory cytokines (IL-10 and TGF-β) and a pro-inflammatory cytokine (TNF-α), in adipocytes isolated from perigonadal white fat obtained from ob/ob mice treated either with PBS (clear bar) or with the oral combination of anti-CD3 (5 μg) plus GC (100 μg) solution for 5 consecutive days.

Figure 10B:
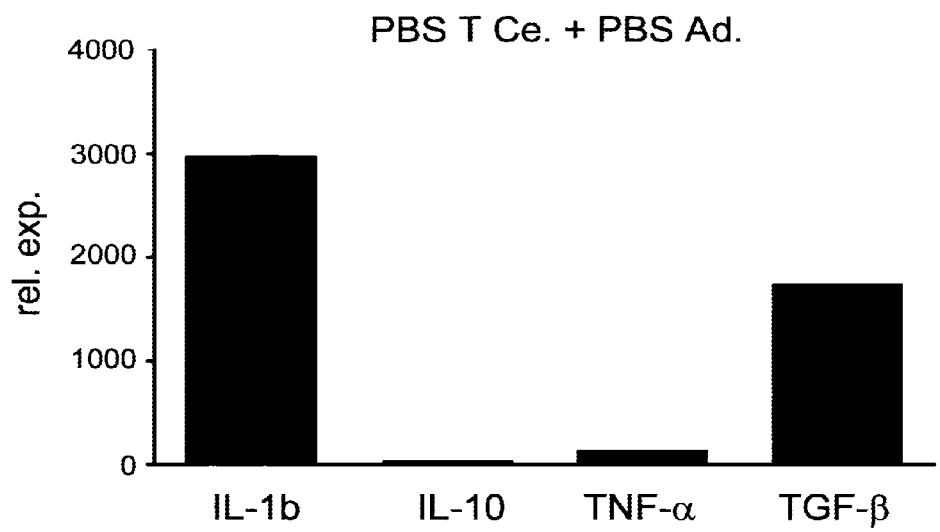
Figure 10C:
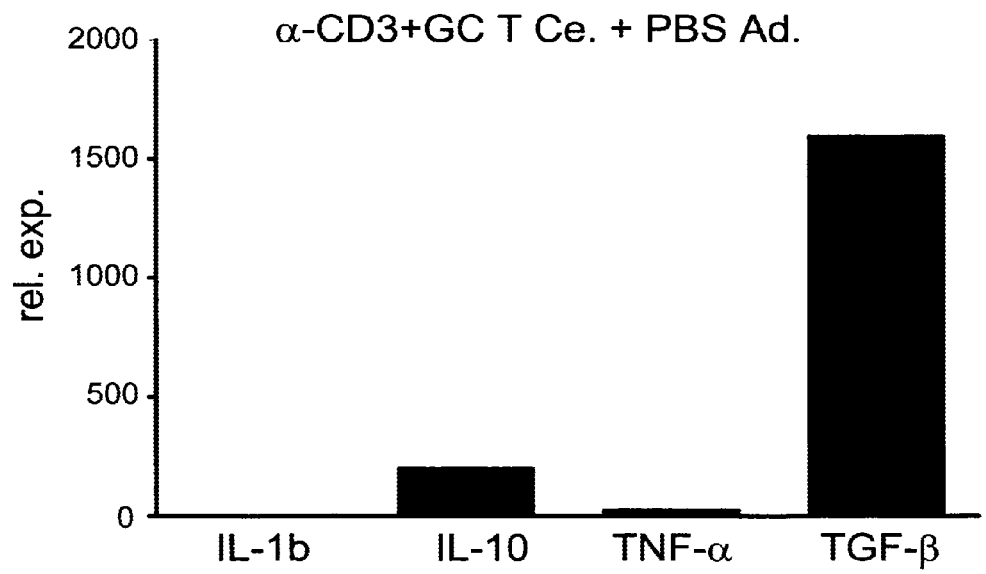

FIGS. 10B and 10C, show relative expression by real time RTPCR, of anti-inflammatory cytokines (IL-10 and TGF-β) and a pro-inflammatory cytokines (TNF-α and IL-1), in adipocytes from control mice that were co-cultured with CD4+ T cells that were negatively selected from spleens of PBS (10B) or oral combination of anti-CD3 and GC (10C) fed mice. Abbreviations: rel. (elative), exp. (expression), Ad. (adipocyte), ce. (cell).

Figure 11A:
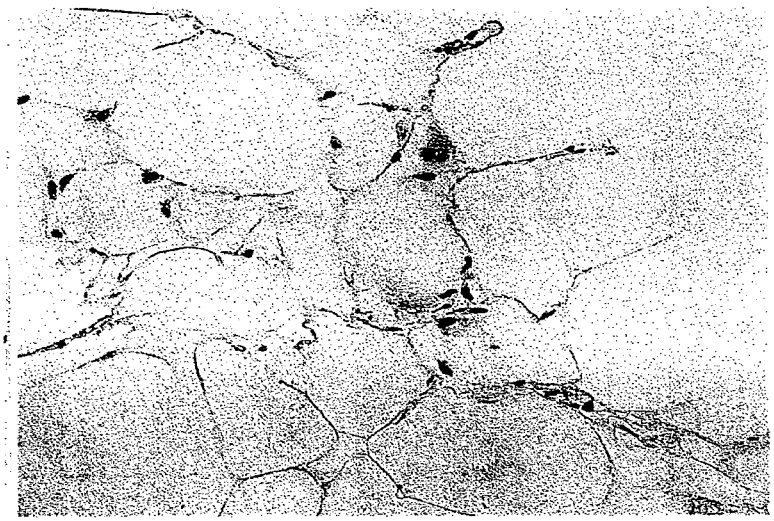
Figure 11B:
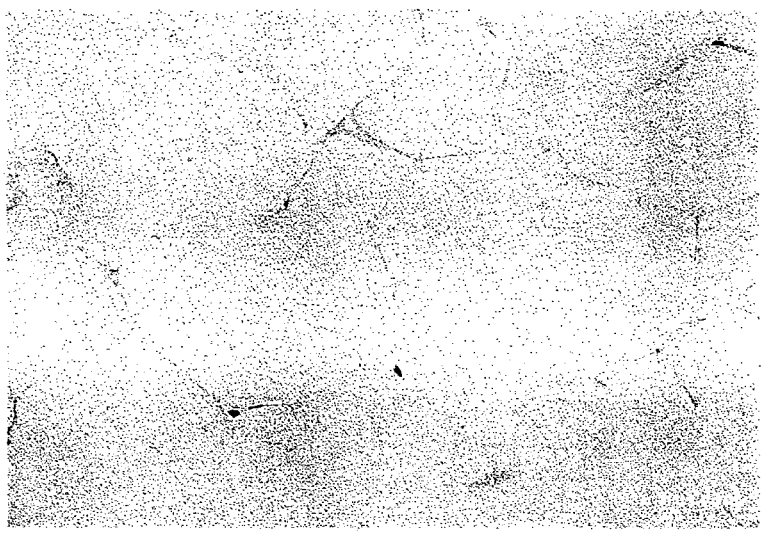

FIG. 11A-11B. Decreased inflammatory cell infiltration following oral anti-CD3 and GC Figure shows paraffin sections of perigonadal white fats obtained from mice fed with 200 μl PBS (11A) or the oral combination of anti-CD3 (5 μg) plus GC (100 μg) solution for five consecutive days (11B). Fat paraffin sections were stained with H&E. Pictures were taken at ×40 magnification.

FIG. 12A-12D. Oral OKT3 increase T cell proliferation

Figure 12A:
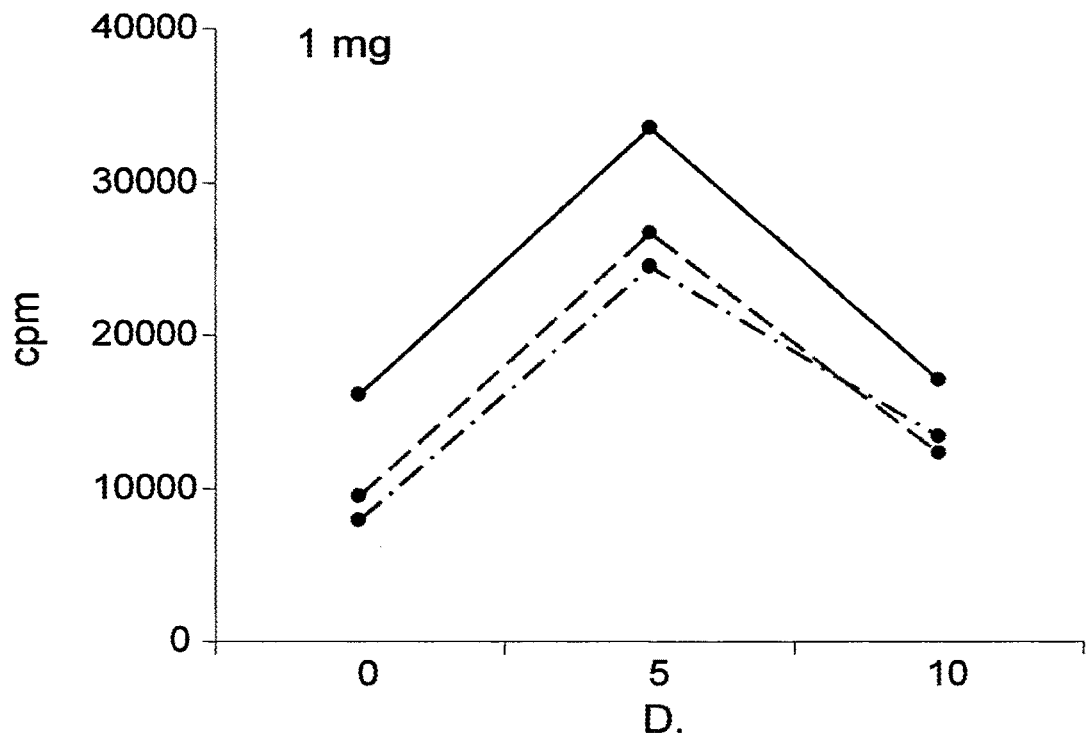
Figure 12B:
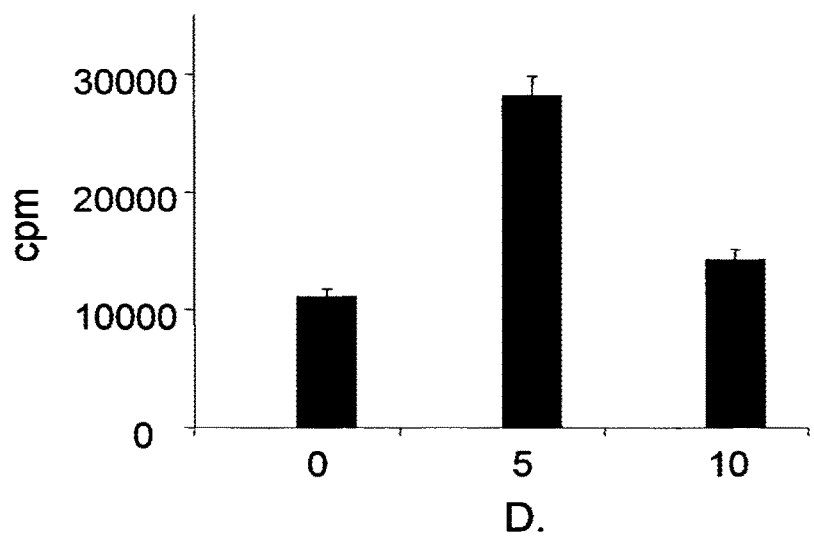
Figure 12C:
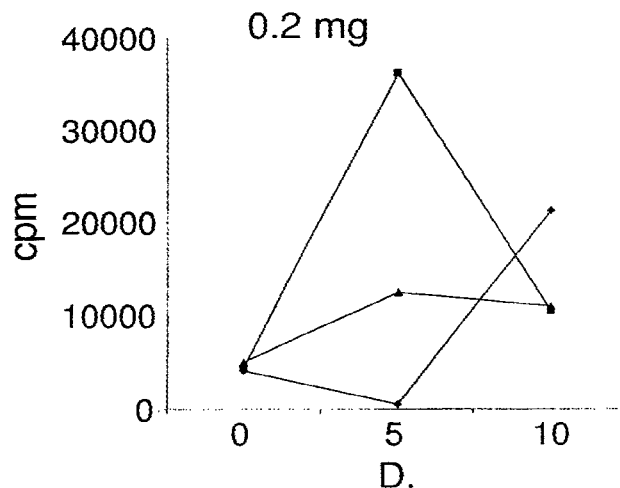
Figure 12D:
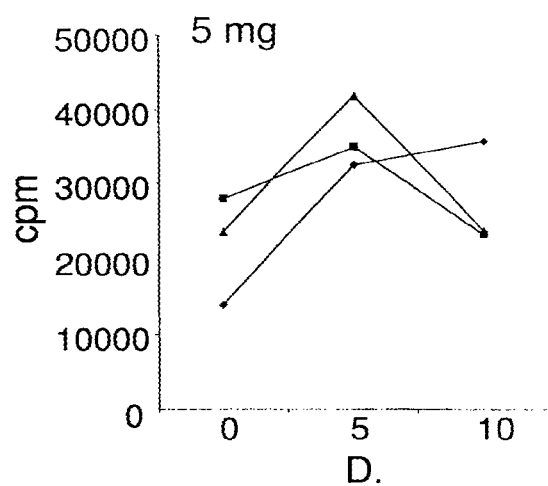

T cell proliferation was tested on days 0, 5 and 10 of the study, for subjects dosed with 0.2, 1.0, and 5.0 mg of OKT3 (FIGS. 12C, 12A and 12D, respectively). FIG. 12B shows mean of three subjects dosed with 1.0 mg. Abbreviations: CPM (counts per minute), D. (days), mg (milligram).

Figure 13A:
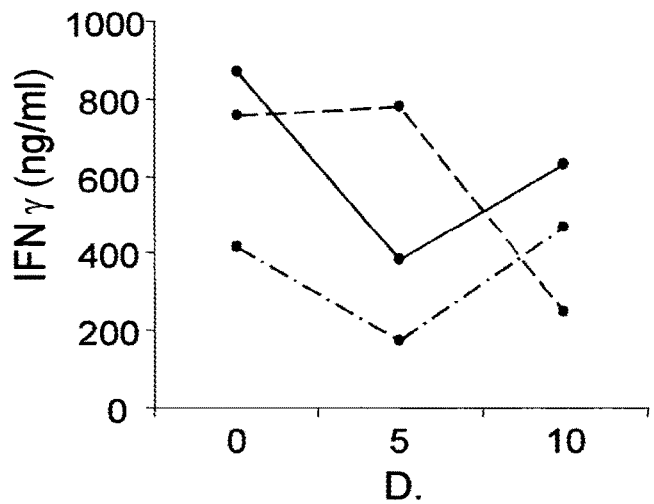
Figure 13B:
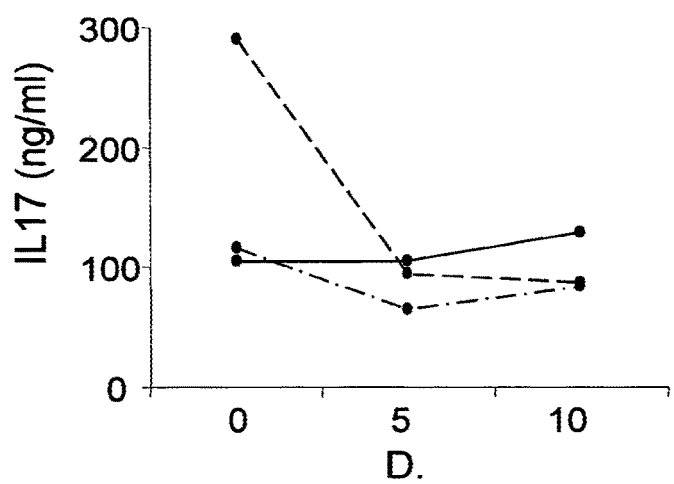
Figure 13C:
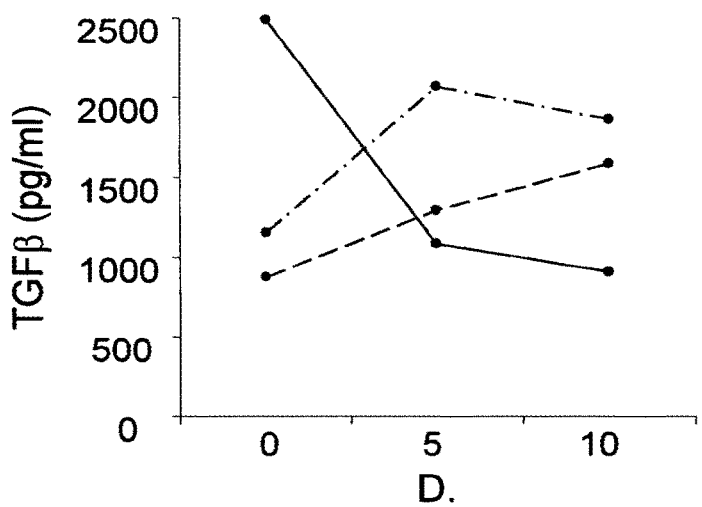

FIG. 13A-13C. Oral OKT3 decreases IFN-γ/IL-17 and increases TGF-β secretion

IFN-γ IL-17, and TGF-β (FIGS. 13A, 13B, 13C, respectively) levels were measured in MLN cells following in-vitro anti-CD3 stimulation (1 ug/ml) on days 0, 5 and 10. Abbreviations: D. (days), ng (nano-gram), pg (pico-gram).

Figure 14A:
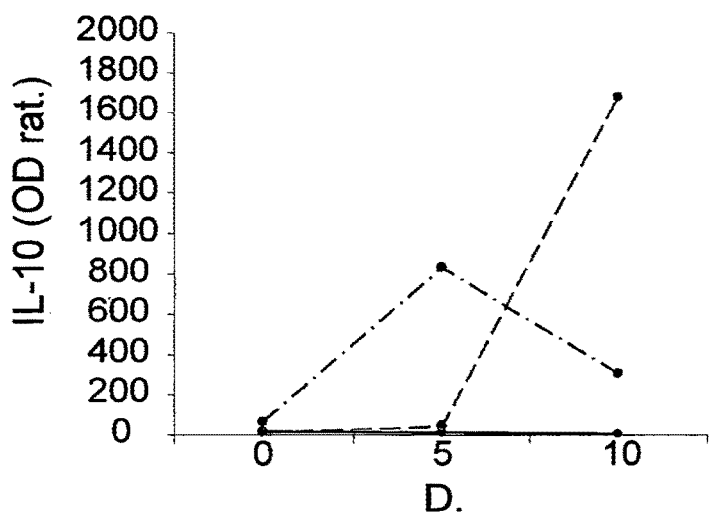
Figure 14B:
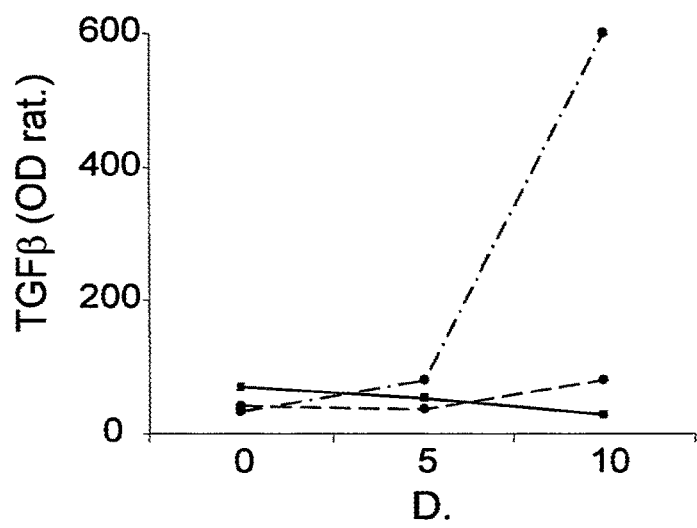
Figure 14C:
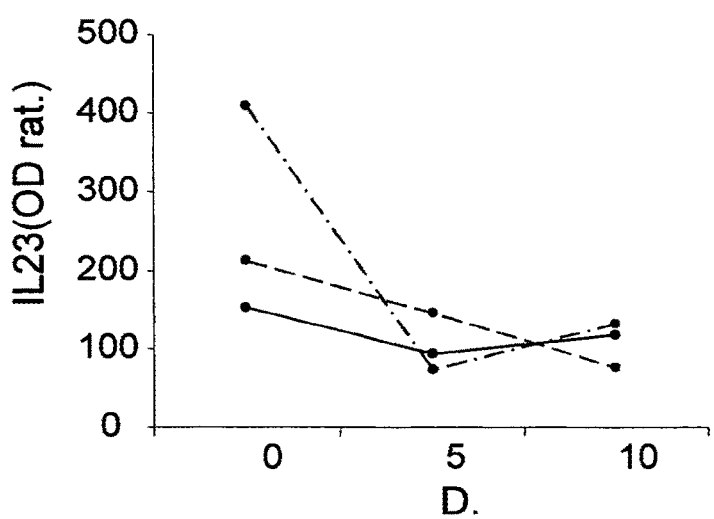

FIG. 14A-14C. Oral OKT3 increases IL-10/TGF-β and decreases IL-23 expression in dendritic cells CD11C+ DCs were isolated from peripheral blood on days 0, 5 and 10 using anti-CD11c magnetic microbeads and IL-10, TGF-β and IL-23 (FIGS. 14A, 14B, 14C, respectively) expression measured by RT PCR. Values are expressed as fold increase or decrease relative to the expression of GAPDH. Abbreviations: D. (days), rat. (ratio).

Figure 15A:
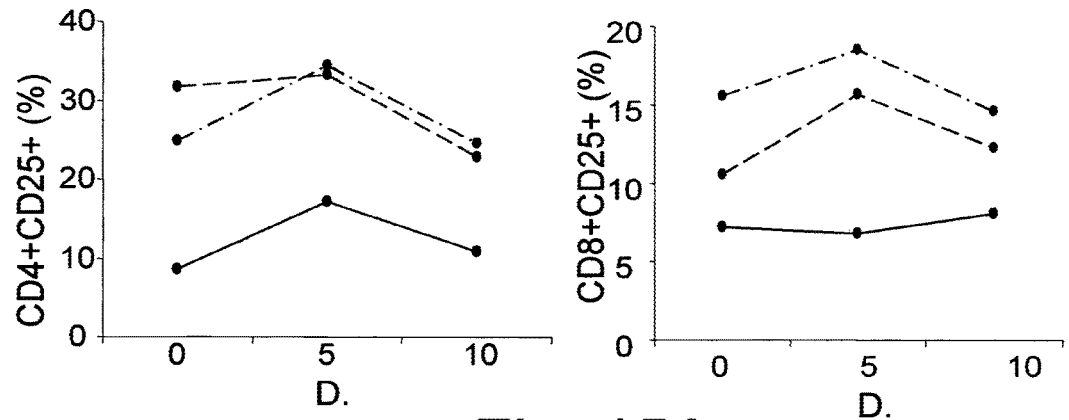
Figure 15B:
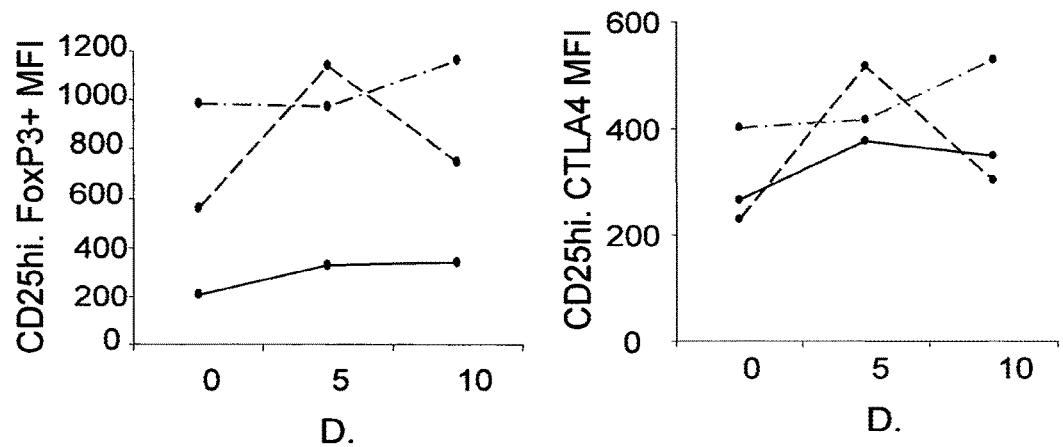
Figure 15C:
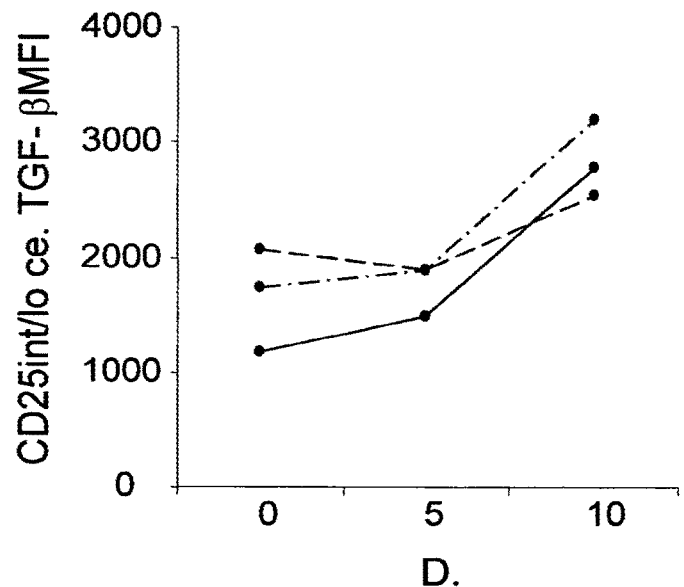

FIG. 15A-15C. Oral OKT3 increases CD4+CD25+ and CD8+CD25+ lymphocytes, and increase Foxp3 and CTLA4Ig expression on CD25(high) regulatory T cells, and TGF-β, and CD127 expression on effector T cells Expression of surface markers on peripheral lymphocytes (CD4+CD25+ and CD8+CD25+), on CD25(high) (Foxp3 and CTLA4Ig), and on effector cells (TGF-β, and CD127) was measured on days 0, 5 and 10 in patients dosed with 1.0 mg OKT3. Abbreviations: D. (days), hi. (high), lo. (low), ce. (cells).

Figure 16A:
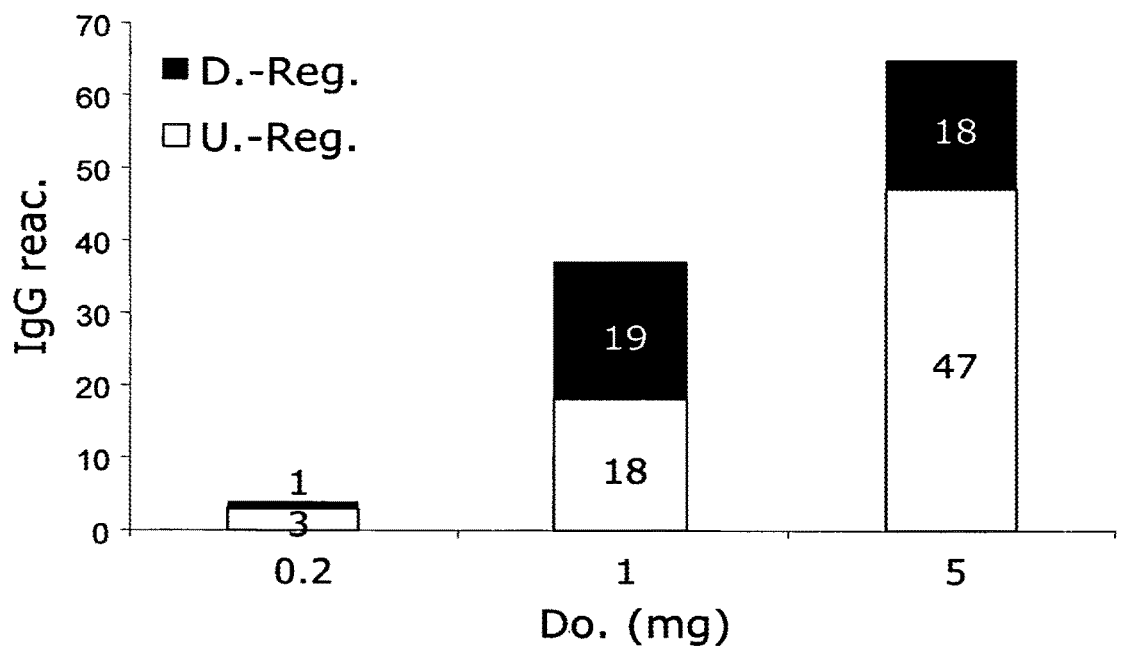
Figure 16B:
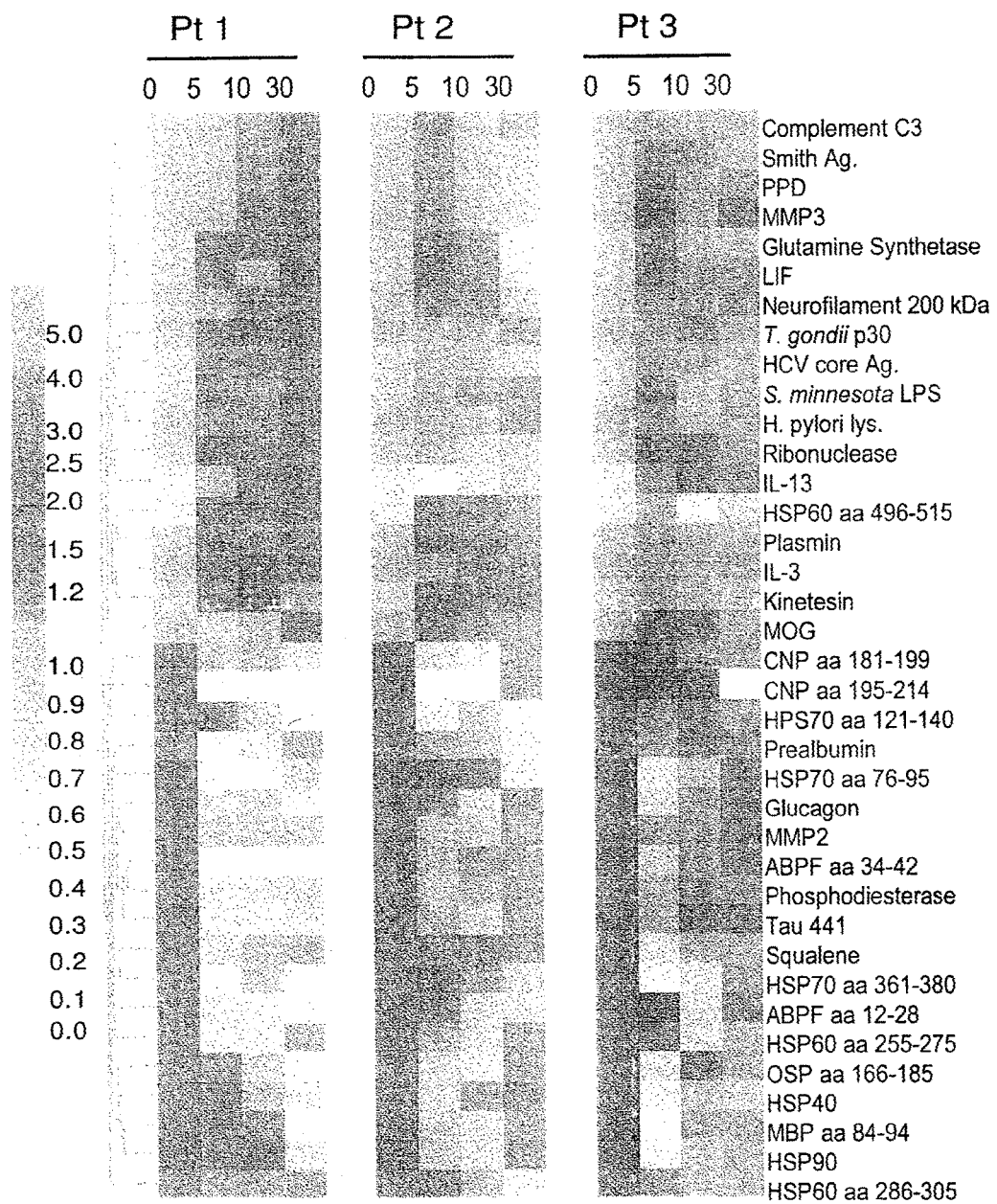

FIG. 16A-16B. Effect of oral OKT3 on antigen arrays

Sera from OKT3-treated subjects were assayed at a 1/10 dilution and the IgG or IgM reactivities were measured.

FIG. 16A. shows a dose-dependent changes in the T-cell dependent IgG repertoire: number of IgG reactivities following treatment with 0.2, 1 and 5 mg/kg of OKT3 respectively.

FIG. 16B. shows a heatmap for three subjects dosed with 1.0 mg OKT3 on days 0, 5 and 10, showing the changes in IgG repertoire detected in subjects treated with a 1 mg/kg dose of OKT3. Abbreviations: D-Reg. (down-regulation), U-Reg. (up-regulation), Do. (dose), reac. (reactivity), Ag. (antigen), Lys. (lysates).

Figure 17A:
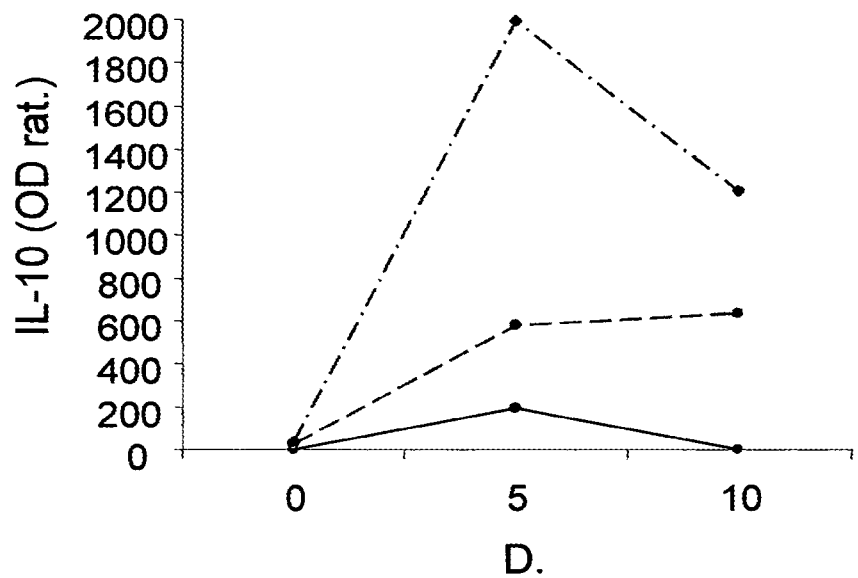
Figure 17B:
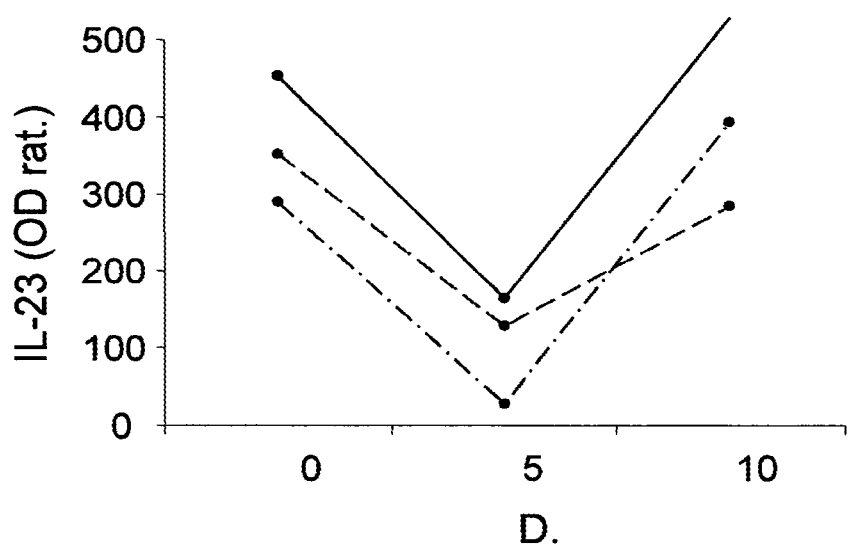

FIG. 17A-17B. Synergistic effect of combination, of GC and OKT3

Three subjects received 7.5 mg of β-glucosylceramide in combination with 1.0 mg of OKT3. CD11C+ DCs were isolated from peripheral blood on days 0, 5 and 10 using anti-CD11c magnetic microbeads and IL-10 and IL-23 (FIGS. 17A, 17B, respectively) expression measured by RT PCR. Values are expressed as fold increase or decrease relative to the expression of GAPDH. Abbreviations: D. (days), rat. (ratio).

DETAILED DESCRIPTION OF THE INVENTION

As indicated herein before, regulatory T cells (Tregs) have been implicated as playing a key role in classic autoimmune diseases in which deficiencies have been identified and strategies to induce Tregs for treatment of these diseases are being actively pursued [Baecher-Allan (2006) ibid.; Belkaid (2007) ibid.; Tang (2006) ibid.]. Although Tregs have been extensively investigated in animal models and human subjects with type 1 diabetes their potential role in Type 2 diabetes has not been well explored and is not well understood. The present invention demonstrates that the induction of regulatory T cells by oral administration of a combined synergistic composition of anti-CD3 plus β-glycosphingolipid alleviates the metabolic syndrome in ob/ob mice in a TGF-β dependent manner.

The mucosal immune system was used by the invention as a means to investigate the effect of Tregs. on metabolic and pathologic abnormalities that are characteristic of the ob/ob mouse. A profound effect both on metabolic parameters including glucose, liver enzymes, cholesterol and triglycerides serum levels followed by elevation of serum levels of insulin and on pathologic abnormalities was observed in the pancreas, liver and muscle. These effects were mediated by the induction of a CD4+LAP+ T cell that acted in a TGF-β dependent manner.

The present invention shows that a combination of both anti-CD3 and GC had the most profound synergistic effect on the metabolic and pathologic abnormalities in the ob/ob mouse although each compound by itself had positive effects. The positive effects were related to the induction of CD4+LAP+ T cells as the inventors were able to transfer protection with these cells and increased numbers of these cells were induced in the MLN (Mesenteric Lymph Nodes) by oral combination of anti-CD3 plus GC. In addition, the invention shows that the effect of the oral combination of anti-CD3 plus GC related as well to effects on NKT cells and dendritic cells. The inventors therefore examined what are the properties of these three cell types and how were they affected by the oral combined administration of anti-CD3 plus GC in a way that alleviated the metabolic and pathologic abnormalities in ob/ob mice.

Latency-associated peptide (LAP) identifies a class of regulatory T cells that function in a TGF-β dependent fashion [Hyytiainen, M. et al. J. Critical reviews in clinical laboratory sciences 41:233-264 (2004); Lawrence, D. A. Molecular and cellular biochemistry 219:163-170]. LAP is the amino-terminal domain of the TGF-β precursor peptide and remains non-covalently associated with the TGF-β peptide after cleavage, forming the latent TGF-β complex [Hyytiainen. (2004) ibid. Lawrence (2001) ibid; Khalil, N. Microbes and infection/Institut. Pasteur 1: 1255-1263 (1999); Faria, A. M. and Weiner, H. L. Inflammation & allergy drug targets 5:179-190 (2006); Saharinen, J. et al Cytokine and growth factor reviews 10:99-117 (1999); Verma, S. C. et al. Current topics in microbiology and immunology 312:101-136 (2007)]. CD4+LAP+ T cells appear to be distinct from naturally occurring CD25+ regulatory T cells, though it has been reported that CD4+CD25+ T cells may express TGF-β on their surface and mediate their suppressive function by presenting TGF-β to a receptor on target cells via cell-to-cell contact [Faria (2006) ibid.; Gandhi, R. et al. J. Immunol. 178:4017-4021 (2007)]. LAP+ cells are thrombospondin positive, and therefore capable of converting latent TGF-β to its active form [Ali, N. A. et al. PLoS ONE 3:e1914 (2008); Oida, T. et al. J. Immunol; 170:2516-2522 (2003); Yang, Z. et al. The Journal of cell biology 176:787-793 (2007); Young, G. D. at al The Journal of biological chemistry 279:47633-47642 (2004)]. LAP+ cells may be involved in the induction of Tregs by producing active TGF-β which is a key cytokine in the induction and maintenance of Tregs [Faria, A. M. and Weiner, H. L. Inflammation & allergy drug targets 5:179-190 (2006)]. In vivo, TGF-β regulates the expression of Foxp3 and expands Foxp3-expressing CD4+CD25+ T cells [Fantini, M. C. et al. J. Immunol. 172:5149-5153 (2004); Hong, J. et al. Proceedings of the National Academy of Sciences of the United States of America 102:6449-6454 (2005); Marie, J. C. et al. The Journal of experimental medicine 201:1061-1067 (2005); Peng, Y. et al. Proceedings of the National Academy of Sciences of the United States of America 101:4572-4577 (2004); Wahl, S. M. et al. Immunological reviews 213:213-227 (2006); Walther, M. et al. Immunity 23:287-296 (2005)]. The results of the present invention, particularly Example 4, indicate that the effect of the oral combination of anti-CD3 plus GC does not appear related to the induction of Foxp3 Tregs, since the results did not indicate any increase in these cells and the effect of oral anti-CD3 plus GC was directly dependent on TGF-β. A clear synergistic effect of oral combination of anti-CD3 plus GC was observed in the induction of CD4+LAP+ T cells. The exact relationship between CD4+LAP+ T cells induced by oral combination of anti-CD3 plus GC, CD4+CD25-LAP+, promoted by oral anti-CD3, and Th3 regulatory T cells known to be enhanced by oral antigens remains to be determined [Faria, A. M. and Weiner, H. L. Clin Dev Immunol 13:143-157 (2006); Faria, A. M. and Weiner, H. L. Immunological reviews 206:232-259 (2005);. Chen, Y. e al. Science 265: 1237-1240 (1994)].

NKT cells are a class of regulatory T cells that express invariant □ chain and have been shown to be involved in oral tolerance [Kim, H. J. et al Immunology 118:101-111 (2006); Levy, L. and Ilan, Y. Recent patents on anti-infective drug discovery 2:217-221 (2007); Trop, S. et al. Inflammatory bowel diseases 9:75-86 (2003); Zeissig, S. et al. American journal of physiology 293:G1101-1105 (2007)]. IL-10 and TGF-β production are reduced in splenocytes and peyer's patches (PPs) from OVA fed CD1d−/− mice compared to WT controls [Kim, H. J. et al Immunology 118:101-111 (2006)]. Beta-glycosphingolipids interact with CD1d, a non-polymorphic MHC class I-like molecule expressed by antigen presenting cells and NKT lymphocytes [Lalazar, G. et al. Mini reviews in medicinal chemistry 6:1249-1253 (2006); Levy, L. and Ilan, Y. Recent patents on anti-infective drug discovery 2:217-221 (2007)]. As previously shown by part of the inventors, administration of GC exerts an immunomodulatory effect in NKT dependent models [Margalit, M. et al. American journal of physiology 289:G917-925 (2005); Safadi, R. et al. International immunology 19:1021-1029 (2007); Zigmond, E. et al. Gut 56:82-89 (2007); Ilan, Y. et al. Transplantation 83:458-467 (2007)]. The inventors thus chose to test the immuno-modulatory effect of a combination of GC with oral anti-CD3.

Intestinal DCs have emerged as key regulators of oral tolerance and intestinal inflammation [Niess, J. H. and Reinecker, H. C. Curr. Opin. Gastroenterol. 22:354-360 (2006)]. Oral tolerance cannot be induced in CCR7-deficient mice that display an impaired migration of DCs from the intestine to MLNs [Macpherson, A. J. and Smith, K. The Journal of experimental medicine 203:497-500 (2006); Milling, S. W. et al. European journal of immunology 37:87-99 (2007); Worbs, T. et al. The Journal of experimental medicine 203:519-527 (2006)]. The conversion of vitamin A into retinoic acid in gut-associated DCs enhances the TGF-β-dependent conversion of naive T cells into Tregs as well as directs Tregs homing to the gut [von Boehmer, H. The Journal of experimental medicine 20.4:1737-1739 (2007]. The expression of TGF-β on the surface of DCs in association with LAP is a mechanism by which immature DCs limit T cell activation to prevent autoimmune responses [Hong, J. et al. Proceedings of the National Academy of Sciences of the United States of America 102:6449-6454 (2005)]. Maturation of DCs upon stimulation with LPS results in the loss of membrane-bound LAP and the up-regulation of HLA class II and co-stimulatory molecules [Gandhi, R. et al. J. Immunol. 178:4017-4021 (2007)]. The presence of LAP on immature DCs inhibits Th1 cell differentiation and is required for the differentiation of Foxp3+ Tregs [Hong, J. et al. Proceedings of the National Academy of Sciences of the United States of America 102:6449-6454 (2005)]. DCs from ob/ob mice are less potent in stimulation of allogeneic T cells associated with TGF-13 secretion [Macia, L. et al. J. Immunol. 177:5997-6006 (2006)]. Since both DCs and NKT cells are defective in ob/ob mice, the inventors hypothesized that alteration of the crosstalk between these cells by the oral combination of anti-CD3 plus GC may be beneficial in this model.

The data of the present invention suggest that the synergistic effect of oral anti-CD3 plus GC altered the function of MLN-derived DCs in a way that enhanced production of TGF-β and IL-10 by T cells in the mesenteric lymph nodes. Without being bound by ay theory, the inventors speculate that oral anti-CD3 binds directly to T cells in the gut and delivers a weak signal that induces LAP+ Treg cells [Ochi, H., et al. Nat Med 12:627-635 (2006)] whereas GC binds DCs in the gut which then affect NKT cells [Margalit, M. et al. American journal of physiology 289:G917-925 (2005)]. The induction of CD4+LAP+ T cells in the MLN then affects target organs as a clear increased levels of TGF-β were found in the pancreas and liver, suggesting that CD4+LAP+ T cells migrate from the gut to exert their effect. Classic studies of oral tolerance have used a specific antigen for the treatment of organ specific autoimmune diseases. There is no "autoantigen" in type 2 diabetes. Because both oral anti-CD3 and GC act in an antigen-nonspecific manner, this provides a unique opportunity to treat a disease such as type 2 diabetes by immunotherapy. Overall, the present invention demonstrates that CD4+LAP+ Tregs from ob/ob mice fed with the combination of anti-CD3 plus GC, alleviate the metabolic syndrome in ob/ob mice in a TGF-β dependent fashion. These results now identify type 2 diabetes, a presumed metabolic disorder, as a disease amenable to therapy based on induction of Treg cells. Furthermore, they suggest that immune dysfunction may underlie the pathogenesis of the disease.

In addition to the results in animal models described above, the inventors further addressed the question of whether oral anti-CD3 given to humans would affect the immune response and whether any toxicity would occur. To test this, OKT3, a murine monoclonal anti-CD3 antibody was used alone or in combination with GC. Based on the invention's animal studies, the inventors checked if although though IV OKT3 given to humans is associated with systemic side effects and development of human anti-mouse responses (HAMA) that this would not occur when OKT3 was given orally. This element is essential in view of the fact that one of the major avenues being pursued for the treatment of autoimmune diseases such as multiple sclerosis is the induction of regulatory T cells and the development of therapy to decrease production of inflammatory cytokines such as IL-17 and IFN-γ. Such desired effects were indeed observed by the present invention. More specifically, using oral treatment of OKT3 alone or in combination with GC, a significant decreased production of IL-17 and IFN-γ and increased production of TGF-β was observed, as shown by FIG. 13. An increase in cells expressing markers for Tregs (Foxp3, CTLA4, TGF-β) following oral OKT3, was also observed.

The invention further shows an increase in the dendritic cell expression of IL-10 and TGF-β and a decrease in dendritic cell expression of IL-23 following oral administration of 1 mg OKT3. Treatment with a combination of GC and OKT3 showed similar and enhanced results.

Induction of T regulatory cells is one of the major goals in immunotherapy of autoimmune diseases and transplantation and the combined compositions of the invention provide a novel, efficient and feasible approach for modulating and using Tregs for treating such disorders.

Thus, in a first aspect, the invention relates to a composition comprising a combination of at least one natural or synthetic beta-glycolipid and at least one immunoglobulin molecule specific for an epitope derived from a component of the immune system or any functional fragments thereof. The combined composition of the invention may optionally further comprises at least one pharmaceutically acceptable carrier, diluent, excipient and/or additive.

According to one embodiment, the beta-glycolipid used by the combined composition of the invention may be any glycolipid selected from the group consisting of a monosaccharide ceramide, a glucosylceramide, a galatosylceremide, a lactosyl-ceramide, a gal-gal-glucosyl-ceramide, GM2 ganglioside, GM3 ganglioside, globoside or any synthetic or natural β-glycolipid or any derivative or combination thereof.

According to one specific embodiment, the combined composition of the invention may comprise beta-glucosylceramide (GC).

In yet another embodiment, the immunoglobulin molecule used for the combined immunomodulatory composition of the invention may be an antibody molecule or any functional fragments thereof, directed against different components of the immune system. Such antibody specifically recognizes an epitope derived from a component of the immune system. Non limiting examples for such components may include co-stimulatory receptors and their ligands, molecules associated with T cell receptors or any other immune-related receptor or markers. For example, antibodies against co-stimulatory molecules known to be involved in immune regulation such as CD3, CD46, CD2, ICOS, CD28, CTLA-4, and PD-1 or their ligands.

According to another embodiment, the antibodies used by the combined composition of the invention may be antibodies against molecules associated with NK-T cells such as CD94, NK G2, antibodies against MHC molecules or their recognition structures such as CD4 and CD8, or antibodies directed against T cell differentiation molecules as TIM molecules. It should be appreciated that antibodies directed against any possible marker for T or B lymphocytes or any other cell of the immune system may also be used in the combined composition of the invention.

According to a particular embodiment, a specific anti-CD-3 antibody may be used for the combined composition of the invention. The CD3 antigen (CD stands for cluster of differentiation) is a protein complex composed of four distinct chains (CD3γ, CD3δ and two times CD3ε) in mammals, that associate with T cell receptor (TCR) and the ζ-chain to generate an activation signal in T lymphocytes. The TCR, ζ-chain and CD3 molecules together comprise the TCR complex.

The CD3γ, CD3δ and CD3ε chains are highly related cell surface proteins of the immunoglobulin superfamily containing a single extracellular immunoglobulin domain. The transmembrane region of the CD3 chains is negatively charged, a characteristic that allows these chains to associate with the positively charged TCR chains (TCRα and TCRβ).

The intracellular tails of the CD3 molecules contain a single conserved motif known as an immunoreceptor tyrosine-based activation motif or ITAM for short, which is essential for the signaling capacity of the TCR. Phosphorylation of the ITAM on CD3 renders the CD3 chain capable of binding an enzyme called ZAP70 (zeta associated protein), a kinase that is important in the signaling cascade of the T cell.

It should be noted that the anti-CD3 antibodies used by the combined composition of the invention can be any antibodies specific for CD3. A number of anti-CD3 antibodies are known, including but not limited to OKT3 (muromonab/Orthoclone OKT3™, Ortho Biotech, Raritan, N.J.; U.S. Pat. No. 4,361,549); hOKTγ1 (Herold et al. N.E.J.M. 346(22):1692-1698 (2002); HuM291 (Nuvion™, Protein Design Labs, Fremont, Calif.); OKT3-5 (Alegre et al. J. Immunol. 148(11):3461-8 (1992); 1F4 (Tanaka et al. J. Immunol. 142:2791-2795 (1989)); G4.18 (Nicolls et al. Transplantation 55:459-468 (1993)); 145-2C11 (Davignon et al. J. Immunol. 141(6):1848-54 (1988)); and as described in Frenken et al. Transplantation 51(4):881-7 (1991); U.S. Pat. Nos. 6,406,696, and 6,143,297).

Methods for making such antibodies are also known. A full-length CD3 protein or antigenic peptide fragment of CD3 can be used as an immunogen, or can be used to identify anti-CD3 antibodies made with other immunogens, e.g., cells, membrane preparations, and the like, e.g., E rosette positive purified normal human peripheral T cells, as described in U.S. Pat. Nos. 4,361,549 and 4,654,210. The anti-CD3 antibody can bind an epitope on any domain or region on CD3.

According to another specific embodiment, the antibody used by the composition of the invention may be an anti-CD46 antibody. Human CD46 is a cell surface glycoprotein expressed on almost all human cells except erythrocytes. The CD46 protein is a type. I membrane protein and is a regulatory part of the complement system. The encoded protein has cofactor activity for inactivation of complement components C3b and C4b by serum factor I, which protects the host cell from damage by complement. In addition, the encoded protein can act as a receptor for different viruses.

The term "antibody" as used herein refers to an immunoglobulin molecule or immunologically active portion thereof, i.e., an antigen-binding portion. Examples of immunologically active portions of immunoglobulin molecules include F(ab) and F(ab')2 fragments, which retain the ability to bind their specific epitope. Such fragments can be obtained commercially or using methods known in the art. For example F(ab)$_2$ fragments can be generated by treating the antibody with an enzyme such as pepsin, a non-specific endopeptidase that normally produces one F(ab)$_2$ fragment and numerous small peptides of the Fc portion. The resulting F(ab)$_2$ fragment is composed of two disulfide-connected Fab units. The Fc fragment is extensively degraded and can be separated from the F(ab)$_2$ by dialysis, gel filtration or ion exchange chromatography. F(ab) fragments can be generated using papain, a non-specific thiol endopeptidase that digests IgG molecules, in the presence of a reducing agent, into three fragments of similar size: two Fab fragments and one Fc fragment. When Fc fragments are of interest, papain is the enzyme of choice because it yields a 50.00 Dalton Fc fragment. To isolate the F(ab) fragments, the Fc fragments can be removed, e.g., by affinity purification using protein A/G. A number of kits are available commercially for generating F(ab) fragments, including the ImmunoPure IgG1 Fab and F(ab')2 Preparation Kit (Pierce Biotechnology, Rockford, Ill.). In addition, commercially available services for generating antigen-binding fragments can be used It should be noted that any antibody used by the combined compositions of the invention may be a polyclonal, monoclonal, recombinant, e.g., a chimeric, deimmunized or humanized, fully human, non-human, e.g., murine, or single chain antibody.

According to another embodiment, chimeric, humanized, de-immunized, or completely human antibodies may be used for applications which include repeated administration, e.g., therapeutic treatment of human subjects.

Chimeric antibodies contain portions of two different antibodies, typically of two different species. Generally, such antibodies contain human constant regions and variable regions from another species, e.g., murine variable regions. For example, mouse/human, chimeric antibodies have been reported which exhibit binding characteristics of the parental mouse antibody, and effecter functions associated with the human constant region. See, e.g., Cabilly et al. U.S. Pat. No. 4,816,567; Shoemaker et al. U.S. Pat. No. 4,978,745; Beavers et al. U.S. Pat. No. 4,975,369; and Boss et al. U.S. Pat. No. 4,816,397, all of which are incorporated by reference herein. Generally, these chimeric antibodies are constructed by so preparing a genomic gene library from DNA extracted from pre-existing murine hybridomas. The library is then screened for variable region genes from both heavy and light chains exhibiting the correct antibody fragment rearrangement patterns. Alternatively, cDNA libraries may be prepared from RNA extracted from the hybridomas and screened, or the variable regions are obtained by polymerase chain reaction. The cloned variable region genes are then ligated into an expression vector containing cloned cassettes of the appropriate heavy or light chain human constant region gene. The chimeric genes can then be expressed in a cell line of choice, e.g., a murine myeloma line.

Humanized antibodies are known in the art and are also antibodies that may be used for the combined composition of the invention. Typically, "humanization" results in an antibody that is less immunogenic, with complete retention of the antigen-binding properties of the original molecule. In order to retain all the antigen-binding properties of the original antibody, the structure of its combining-site has to be faithfully reproduced in the "humanized" version. This can potentially be achieved by transplanting the combining site of the nonhuman antibody onto a human framework, either (a) by grafting the entire nonhuman variable domains onto human constant regions to generate a chimeric antibody (which preserves the ligand-binding properties, but which also retains the immunogenicity of the nonhuman variable domains), (b) by grafting only the nonhuman CDRs (complementarity determining regions) onto human framework and constant regions with or without retention of critical framework residues or (c) by transplanting the entire nonhuman variable domains (to preserve ligand-binding properties) but also "cloaking" them with a human-like surface through judicious replacement of exposed residues (to reduce antigenicity).

Humanization by CDR grafting typically involves transplanting only the CDRs onto human fragment onto human framework and constant regions. Theoretically, this should substantially eliminate immunogenicity (except if allotypic or idiotypic differences exist).

However, it has been reported that some framework residues of the original antibody also is need to be preserved [Riechmann et al. Nature 332:323 (1988); Queen et al. Proc. Natl. Acad. Sci. USA 86: 10,029 (1989)]. The framework residues which need to be preserved can be identified by computer modeling. Alternatively, critical framework residues may potentially be identified by comparing known antibody combining site structures. The invention also includes partially humanized antibodies, in which the CDRs of the heavy and light chains and a limited number of structural amino acids of the murine monoclonal antibody are grafted by recombinant technology to the CDR-depleted human IgG scaffold.

Deimmunized antibodies are made by replacing immunogenic epitopes in the murine variable domains with benign amino acid sequences, resulting in a deimmunized variable domain. The deimmunized variable domains are linked genetically to human IgG constant domains to yield a deimmunized antibody.

The antibodies used by the composition of the invention can also be a single chain antibody. A single-chain antibody (scFV) can be engineered, dimerized or multimerized to generate multivalent antibodies having specificities for different epitopes of the same target protein.

According to another specific embodiment, the combined composition of the invention may further comprise at least one additional therapeutic agent.

According to one embodiment, the combined composition of the invention may comprises at least one beta-glycolipid combined with at least one immunoglobulin molecule (preferably, antibody) at any quantitative ratio of between about 1:1 to 1000:1. It should be appreciated that any quantitative ratio of the combined compounds may be used. As a non-limiting example, a quantitative ratio used between any of the compounds may be: 1:1, 1:2, 1:3, 1:4, 1:5, 1:6, 1:7, 1:8, 1:9, 1:10, 1:20, 1:30, 1:40, 1:50, 1:60, 1:70, 1:80, 1:90, 1:100, 1:200, 1:300, 1:400, 1500, 1:750, 1:1000. It should be further noted that where the combination of the invention comprises more than two compounds, the quantitative ratio used may be for example, 1:1:1, 1:2:3, 1:10:100, 1:10:100:1000 etc.

According to a particular embodiment, the composition of the invention comprises a combination of glucosylceramide (GC) and as immunoglobulin molecule, an anti-CD3 antibody.

According to a specific embodiment, a combination of a particular β-glycolipid and particular antibody used by the combined compositions and methods of the invention comprises β-glucosylceramide (GC) and anti-CD3 antibody at a quantitative ratio between about 100:1 to 1:1. In another embodiment, the combinations used by the invention may comprise β-glucosylceramide (GC) and anti-CD3 antibody at a quantitative ratio of any one of 100:1 and 5:1, preferably, 20:1.

As shown by Example 1, daily oral administration of the composition of the invention comprises a combination of 100 μg GC+5 μg anti-CD3 antibody (20:1), showed significant synergistic anti-inflammatory effects, using the ob/ob model. Based on these results, a daily amount of such particular combination may contain between about 0.1 to 100, specifically, 0.5 to 50, and more specifically, 5 mg per kg of body weight of β-glucosylceramide and between about 0.01 to 50, specifically, 0.1 to 1, and more specifically, 0.25 mg per kg of body weight of anti-CD3 antibody at a quantitative ratio of 100:1 of 10:1, specifically of 20:1.

According to another particular and specific embodiment, the combination used by the compositions, methods and kits of the invention may comprise 5 mg per kg of body weight β-glucosylceramide and 0.25 mg per kg of body weight anti-CD3 antibody.

As shown by Examples 9-14, in human subjects, the specific effective amount of OKT3 used may be between about 0.05 to 10 mg, specifically, 0.1 to 5 mg, more specifically, 0.2, 1 and 5 mg. A specific embodiment presented by Example 13 show an effective particular combination of 0.2, 1 and 5 mg OKT3 and about 0.5 to 20 mg GC, specifically, 7.5 mg.

It should be appreciated that these preferred amounts of active ingredients are specific for a certain immune-related disorder, the Metabolic Syndrom. Appropriate concentrations for any other immune-related disorders should be determined by the treating physician.

It should be appreciated that a therapeutically effective amount of the combined beta-glycolipid and antibody (i.e., an effective dosage) depends on the antibody selected, the mode of delivery, and the condition to be treated.

According to one embodiment, the composition of the invention may be an immunomodulatory composition modulating the Th1/Th2, Th3 cell balance in a subject suffering from an immune-related disorder. Thereby, such composition may activate or inhibit an immune response specifically directed toward said disorder in the treated subject.

According to another specific embodiment the composition of the invention modulates the Th1/Th2, Th3 cell balance toward an anti-inflammatory Th2, Tr1/Th3 immune response in a subject suffering from an immune-related disorder.

More specifically, as also shown by the following Examples, according to one specific embodiment, the immunomodulatory combined composition of the invention leads to a decrease or reduction in the amount or expression of pro-inflammatory cytokines such as IL-2, IL-17, IL-23, IFN-γ, IL-6. Such decrease or reduction according to the invention may be a reduction of about 5% to 99%, specifically, a reduction of about 5%, 10%, 15%, 20%, 25%, 30%, 35%, 40%, 45%, 50%, 55%, 60%, 65%, 70%, 75%, 80%, 85%, 90%, 95% or 99% as compared to untreated control. In yet another specific embodiment, the composition of the invention elevates and increases the amount or expression of anti-inflammatory cytokines such as TGF-β, and IL-10 IL-4, IL-5, IL-9 and IL-13. More specifically, the increase, induction or elevation of the anti-inflammatory cytokines may be an increase of about 5%, 10%, 15%, 20%, 25%, 30%, 35%, 40%, 45%, 50%, 55%, 60%, 65%, 70%, 75%, 80%, 85%, 90%, 95% or 99% as compared to untreated control.

As shown by Examples, the combined composition of the invention exhibits a clear immuno-modulatory effect on immune-related cell. An immune-related cell may be an APC (such as DC), Treg cell or any other cell associated directly on indirectly with the immune system including but not limited to platelets, macrophages, any type of B cell, T cell (including double negative cells), and any type of non-professional antigen presenting cell, adipocytes, endothelial cell, any type of cell that is part of an organ, specifically, an organ connected to the treated immune-related disorder and any type of cell having regulatory enhancing or suppressing properties. More particularly, the combined composition of the invention demonstrate immuno-modulation, specifically, anti-inflammatory effect on immune-related cells such as specific T regulatory cells for example, CD4+LAP+, adipocytes and Antigen Presenting Cells (APC), such as DC. Therefore, according to one embodiment, the composition of the invention may be used for inducing at least one of T regulatory (Treg) cells, or any cell having regulatory properties, either suppressive or inductive, adipocyte and Antigen Presenting Cells (APC) in a subject suffering from an immune-related disorder. More specifically, immune-related cells induced by the composition of the invention may be any T regulatory cell, for example any one of CD4+LAP+ T-reg cells, CD4+CD25 T-reg cells, CD8+CD25 T-reg cells, FoxP3+CD4 T-reg cells, CD25 High T-reg cells, CD127 MFI T-reg cells, CD28 MFI T-reg cells, CTLA4– T-reg cells and HLA-DR T-reg cells. According to one specific embodiment, the combined composition of the invention induces CD4+LAP+ T-reg cells. As shown by the Examples, the composition of the invention leads to increase in the amount of these cells in MLN, spleen and blood.

As shown by the Examples, the combined composition of the invention also induces DC expressing TGF-β and LAP, as well as DC expressing any one of IL23, IL-1 and IL-6, therefore, according to another embodiment the combined composition of the invention may be used for inducing any APC, particularly, Dendritic Cell (DC). Several cell types appear to be capable of serving as APC, including dendritic cells (DC), activated B cells, T2 cells (TAP-deficient lymphoblastoid cells line) and activated macrophages. In accordance with the invention the APCs may be a dendritic cell (DC). It is understood that one of skill in the art will recognize that other antigen presenting cells, either professional or non-professional may be useful in the invention, such as B cells, whole spleen cells, peripheral blood macrophages, fibroblasts, platelets, adipocytes, endothelial cell or non-fractionated peripheral blood mononuclear cells (PBMC). Therefore, the invention is not limited to the exemplary cell types which are specifically mentioned and exemplified herein.

As shown by Example 8, the combined composition of the invention demonstrates a marked anti-inflammatory effect on edipocyte cells as well on the fat tissue of the treated subject. Therefore, according to one embodiment, the composition of the invention leads to induction of anti-inflammatory cytokine such as TGF-β and IL-10 and reduction in the expression of pro-inflammatory cytokines such as TNF-α and IL-1.

Adipocytes are the cells that primarily compose adipose tissue, specialized in storing energy as fat. There are two types of adipose tissue, white adipose tissue (WAT) and brown adipose tissue (BAT), which are also known as white fat and brown fat, respectively, and comprise the two types of fat cells. White fat cells or monovacuolar cells contain a large lipid droplet surrounded by a layer of cytoplasm. The nucleus is flattened and located on the periphery. A typical fat cell is 0.1 mm in diameter with some being twice that size and others half that size. The fat stored is in a semi-liquid state, and is composed primarily of triglycerides and cholesteryl ester. White fat cells secrete resistin, adiponectin, and leptin. Brown fat cells or plurivacuolar cells are polygonal in shape. Unlike white fat cells, these cells have considerable cytoplasm, with lipid droplets scattered throughout. The nucleus is round, and, although eccentrically located, it is not in the periphery of the cell. The brown color comes from the large quantity of mitochondria.

According to another embodiment, the immuno-modulatory composition of the invention leads to reduction in NK T cells.

As demonstrated by Example 5, the clear inducing effect of the combined composition of the invention on a specific population of Treg. cells enabled the isolation and use of these cell for adoptive transfer. Thus, according to another embodiment, the invention further provides a composition comprising immune-cells, specifically, Tregs, DC or any other cell associated directly on indirectly with the immune system including but not limited to platelets, macrophages, any type of B cell, T cell (including double negative cells), and any type of non-professional antigen presenting cell, adipocytes, endothelial cell, any type of cell that is part of an organ, specifically, an organ connected to the treated immune-related disorder and any type of cell having regulatory enhancing or suppressing properties, treated with the combined composition or obtained from a subject treated with the combined composition of the invention.

The immuno-modulatory effect of the combined composition of the invention may be specifically applicable in the treatment of immune-related disorders. Therefore, the invention further provides a pharmaceutical composition for treating, preventing, ameliorating or delaying the onset of an immune-related disorder in a subject in need thereof comprising as an active ingredient a therapeutically effective amount of a combination of at least one natural or synthetic beta-glycolipid and at least one immunoglobulin molecule specific for an epitope derived from a component of the immune system or any functional fragments thereof, and optionally at least one additional therapeutic agent, with a pharmaceutically acceptable carrier. It should be noted that the pharmaceutical composition provided by the invention is as described herein before.

Modulation of the Th1/Th2, Th3 balance towards an anti-inflammatory Th2, Tr1/Th3 response may be particularly applicable in immune related disorders having an undesired unbalanced pro-inflammatory Th1 reaction.

For example, such immune-related disorders may be Metabolic Syndrome or any of the conditions comprising the same, an autoimmune disease, graft rejection pathology, inflammatory disease, non alcoholic fatty liver disease, hyperlipidemia and atherosclerosis.

As shown by the Examples, the composition of the invention significantly decreased the serum levels of cholesterol, triglycerides, ALT, AST and Glucose. Example 1 further shows that the combined composition of the invention leads to a significant increase in serum levels of insulin. Therefore, according to one embodiment, the pharmaceutical composition of the invention leads to at least one of a decrease in the serum levels of cholesterol, triglycerides, ALT, AST and Glucose and an increase in the serum levels of insulin in a subject suffering of an immune-related disorder. Wherein indicated decease, reduction, inhibition, it is meant that the composition of the invention leads to a reduction of about 0.5% to 99% of the serum level of any one of cholesterol, triglycerides, ALT, AST and Glucose, of a subject suffering of an-immune-related disorder. More specifically, such reduction may be a reduction of about, 5%, 10%, 15%, 20%, 25%, 30%, 35%, 40%, 45%, 50%, 55%, 60%, 65%, 70%, 75%, 80%, 85%, 90%, 95% and over 99%, as compared to the levels prior to the treatment, or the levels of untreated control. Wherein indicated increase, elevation, enhancement, induction, it is meant that the composition of the invention leads to induction, or increase of about 5% to 99% of the serum level of insulin in a subject suffering of an-immune-related disorder. More specifically, such increase may be an increase of about, 5%, 10%, 15%, 20%, 25%, 30%, 35%, 40%, 45%, 50%, 55%, 60%, 65%, 70%, 75%, 80%, 85%, 90%, 95% and over 99%, as compared to the levels prior to the treatment, or the levels of untreated control.

According to another embodiment, the composition of the invention may further lead to a significant reduction in pancreatic hyperplasia and hepatic fat accumulation.

Still further, according to another embodiment, the combined composition of the invention down-regulates macrophages while increasing foxp3+ regulatory T cells in fat tissue, suppresses inflammatory cytokine production by adipocytes and clearly leads to a marked decrease of inflammatory cell infiltration to fat tissue of a treated subject, specifically, a subject suffering from an immune-related disorder.

Accordingly, the composition of the invention may be applicable for treating a subject suffering of a metabolic syndrome or any of the conditions comprising the same.

The Metabolic Syndrome is characterized by a group of metabolic risk factors in one person including:

*Abdominal obesity (excessive fat tissue in and around the abdomen);

*Atherogenic dyslipidemia (blood fat disorders—high triglycerides, low HDL cholesterol and high LDL cholesterol—that foster plaque buildups in artery walls); *Elevated blood pressure; *Insulin resistance or glucose intolerance; *Prothrombotic state (e.g., high fibrinogen or plasminogen activator inhibitor-1 in the blood); and *Proinflammatory state (e.g., elevated C-reactive protein in the blood). People with the metabolic syndrome are at increased risk of coronary heart disease and other diseases related to plaque buildups in artery walls (e.g., stroke and peripheral vascular disease) and type 2 diabetes.

More particularly, the combined composition of the invention is intended for the treatment of dyslipoproteinemia, which may include hypertriglyceridemia, hypercholesterolemia and low HDL-cholesterol, obesity, NIDDM (non-insulin dependent diabetes mellitus), IGT (impaired glucose tolerance), blood coagulability, blood fibronolysis defects and hypertension.

According to another embodiment, the immunomodulatory combined composition of the invention may be used for treating diabetes, particularly, Type 1 diabetes. Diabetes mellitus, often simply diabetes, is a syndrome characterized by disordered metabolism and inappropriately high blood sugar (hyperglycaemia) resulting from either low levels of the hormone insulin or from abnormal resistance to insulin's effects coupled with inadequate levels of insulin secretion to compensate. The characteristic symptoms are excessive urine production (polyuria), excessive thirst and increased fluid intake (polydipsia), and blurred vision. These symptoms are likely absent if the blood sugar is only mildly elevated.

The World Health Organization recognizes three main forms of diabetes mellitus: Type 1, Type 2, and gestational diabetes (occurring during pregnancy), which have different causes and population distributions. While, ultimately, all forms are due to the beta cells of the pancreas being unable to produce sufficient insulin to prevent hyperglycemia, the causes are different. Type 1 diabetes is usually due to autoimmune destruction of the pancreatic beta cells. Type 2 diabetes is characterized by insulin resistance in target tissues, this causes a need for abnormally high amounts of insulin and diabetes develops when the beta cells cannot meet this demand. Gestational diabetes is similar to type 2 diabetes in that it involves insulin resistance, hormones in pregnancy may cause insulin resistance in women genetically predisposed to developing this condition.

Acute complication of diabetes (hypoglycemia, ketoacidosis or nonketotic hyperosmolar coma) may occur if the disease is not adequately controlled. Serious long-term complications include cardiovascular disease (doubled risk), chronic renal failure, retinal damage (which can lead to blindness), nerve damage (of several kinds), and microvascular damage, which may cause impotence and poor healing. Poor healing of wounds, particularly of the feet, can lead to gangrene, which may require amputation.

According to one embodiment, the immunomodulatory combined composition of the invention may be used for the treatment of Type 1 diabetes. Type 1 diabetes mellitus is characterized by loss of the insulin-producing beta cells of the islets of Langerhans in the pancreas, leading to a deficiency of insulin. The main cause of this beta cell loss is a T-cell mediated autoimmune attack. According to another embodiment, the combined composition of the invention is intended for treating type 2 diabetes.

In yet another embodiment, the pharmaceutical composition of the invention may be used for the treatment of an autoimmune disorder. Examples of autoimmune disorders include, but are not limited to, Alopecia Areata, Lupus, Anlcylosing Spondylitis, Meniere's Disease, Antiphospholipid Syndrome, Mixed Connective Tissue Disease, Autoimmune Addison's Disease, Multiple Sclerosis, Autoimmune Hemolytic Anemia, Myasthenia Gravis, Autoimmune Hepatitis, *Pemphigus* Vulgaris, Behcet's Disease, Pernicious Anemia, Bullous Pemphigoid, Polyarthritis Nodosa, Cardiomyopathy, Polychondritis, Celiac Sprue-Dermatitis, Polyglandular Syndromes, Chronic Fatigue Syndrome (CFIDS), Polymyalgia Rheumatica, Chronic Inflammatory Demyelinating, Polymyositis and Dermatomyositis, Chronic Inflammatory Polyneuropathy, Primary Agammaglobulinemia, Churg-Strauss Syndrome, Primary Biliary Cirrhosis, Cicatricial Pemphigoid, Psoriasis, CREST Syndrome, Raynaud's Phenomenon, Cold Agglutinin Disease, Reiter's Syndrome, Crohn's Disease, Rheumatic Fever, Discoid Lupus, Rheumatoid Arthritis, Essential Mixed, Cryoglobulinemia Sarcoidosis, Fibromyalgia, *Scleroderma*, Grave's Disease, Sjogren's Syndrome, Guillain-Barre, Stiff-Man Syndrome, Hashimoto's Thyroiditis, Takayasu Arteritis, Idiopathic Pulmonary Fibrosis, Temporal Arteritis/Giant Cell Arthritis, Idiopathic Thrombocytopenia Purpura (ITP), Ulcerative Colitis, IgA Nephropathy, Uveitis, Insulin Dependent Diabetes (Type I), Vasculitis, Lichen Planus, and Vitiligo. The oral combined beta-glycolipid and antibody compositions described herein can be administered to a subject to treat or prevent disorders associated with an abnormal or unwanted immune response associated with cell, tissue or organ transplantation, e.g., renal, hepatic, and cardiac transplantation, e.g., graft versus host disease (GVHD), or to prevent allograft rejection.

According to a specifically preferred embodiment, an autoimmune disease treated by the composition of the invention may be any one of rheumatoid arthritis, type 1 diabetes, type 2 diabetes, artherosclerosis, asthma, acute and chronic graft versus host disease, systemic lupus erythematosus, scleroderma, multiple sclerosis, inflammatory bowel disease, psoriasis, uvietis, thyroiditis and immune mediated hepatitis.

According to another embodiment, the combined composition of the invention may be used for the treatment of MS. Multiple Sclerosis (MS) is typically characterized clinically by recurrent or chronically progressive necrologic dysfunction, caused by lesions in the CNS. Pathologically, the lesions include multiple areas of demyelination affecting the brain, optic nerves, and spinal cord. The underlying etiology is uncertain, but MS is widely believed to be at least partly an autoimmune or immune-mediated disease.

Thus, the invention includes compositions and methods of treating, delaying or preventing the onset of MS, by orally or mucosally administering the combined beta-glycolipid and antibody. Included are methods wherein a subject who has or is at risk of having MS is orally administered combined beta-glycolipid and antibody.

According to another preferred embodiment, the combined composition of the invention may be used for the treatment of RA. Rheumatoid arthritis (RA) is the most common chronic inflammatory arthritis and affects about 1% of adults, it is two to three times more prevalent in women than in men. RA may begin as early as infancy, but onset typically occurs in the fifth or sixth decade.

Diagnosis may be made according to the American Rheumatism Association Criteria for the so Classification of Rheumatoid Arthritis. A therapeutically effective amount will cause an improvement in one or more of the following: the number of inflamed joints, the extent of swelling, and the range of joint motion. Laboratory measurements (e.g., ESR and hematocrit value) and assessments of subjective features (e.g., pain and morning stiffness) can also be made. The invention also includes methods of treating autoimmune arthritis, e.g., RA, in a subject by administering to the subject a therapeutically effective amount of combined composition of the invention comprising beta-glycolipid and antibody.

The combined compositions of the invention described herein can also be used to treat or prevent graft rejection in a transplant recipient. For example, the compositions can be used in a wide variety of tissue and organ transplant procedures, e.g., the compositions can be used to induce central tolerance in a recipient of a graft of cells, e.g., stem cells such as bone marrow and/or of a tissue or organ such as pancreatic islets, liver, kidney, heart, lung, skin, muscle, neuronal tissue, stomach, and intestines. Thus, the new methods can be applied in treatments of diseases or conditions that entail cell, tissue or organ transplantation (e.g., liver transplantation to treat hypercholesterolemia, transplantation of muscle cells to treat muscular dystrophy, or transplantation of neuronal tissue to treat Huntington's disease or Parkinson's disease).

According to another embodiment, the combined composition of the invention may modulate the Th1/Th2, Th3 balance towards an anti-Th2, Tr1/Th3 response in a subject suffering from IBD. Therefore, according to one embodiment, the composition of the invention is intended for treating IBD. Inflammatory bowel diseases (IBD) are common gastrointestinal disorders, that can be perceived as being the result of a dysbalance between Th1-pro-inflammatory, and Th2-anti-inflammatory subtypes of immune responses [Strober, W., et al. Immunol Today 18:61-64 (1997); Neurath, M., et al. J. Exp. Med. 183:2605-2616 (1996)].

Patients with IBD have antibodies against components of colon cells and several different bacterial antigens. These antigens gain access to the immune system as a consequence of epithelial damage [Hibi, S., et al. Clin. Exp. Immunol. 54:163-168 (1983); Das, K. M., et al. Gastroenterology 98:464-69 (1990)]. Abnormalities of T cell-mediated immunity, including coetaneous anergy and diminished responsiveness to T cell stimuli, have also been described in these patients [Chiba, M., et al. Gut, 22:177-182 (1981); Raedler, A., et al. Clin. Exp. Immunol. 60:518-526 (1985)]. In addition, changes in mucosal cell mediated immunity were identified, including increased concentrations of mucosal IgG cells and changes in T cells subsets, suggesting antigen stimulation [Dasgupta, A., et al. Gut 35:1712-17 (1994); Takahashi, F., et al. J. Clin. Invest. 76:311-318 (1985)]. Exposure of target antigens after infectious, immune, or toxic damage, leads to activation of mucosal immune cells resulting in cytokines that lead to mucosal inflammatory response [Neurath, M., et al. J. Exp. Med., 183:2605-2616 (1996)]. Secretion of pro-inflammatory cytokines such as IFNγ, contributes to an increase in mucosal permeability, and has been described in animal models of IBD [Strober, W., et al. Immunol. Today 18:61-64. (1997)].

In yet another preferred embodiment, the combined composition of the invention may be used for the treatment of atherosclerosis. Atherosclerosis is a slowly progressive disease characterized by the accumulation of cholesterol within the arterial wall. The atherosclerotic process begins when LDL-C becomes trapped within the vascular wall. Oxidation of the LDL-C results in the bonding of monocytes to the endothelial cells lining the vessel wall. These monocytes are activated and migrate into the endothelial space where they are transformed into macrophages, leading to further oxidation of LDL-C. The oxidized LDL-C is taken up through the scavenger receptor on the macrophage leading the formation of foam cells. A fibrous cap is generated through the proliferation and migration of arterial smooth muscle cells, thus creating an atherosclerotic plaque. Lipids depositing in atherosclerotic legions are derived primarily from plasma apo B containing lipoproteins. These include chylomicrons, LDL-C, IDL, and VLDL. This accumulation forms bulky plaques that inhibit the flow of blood until a clot eventually forms, obstructing an artery and causing a heart attack or stroke.

In another alternative and specific embodiment, the combined composition of the invention may modulate the Th1/Th2, Th3 cell balance toward a pro-inflammatory Th1 immune response in a subject suffering from an immune-related disorder.

Modulation of the Th1/Th2, Th3 balance towards a pro-inflammatory Th1 response may be particularly applicable in immune related disorders having an undesired unbalanced anti-inflammatory Th2 response, for example, a malignant and non-malignant proliferative disorder, infectious disease, genetic disease and neurodegenerative disorders.

Thus, in another specific embodiment, the combined composition of the invention is intended for the treatment of a malignancy. In cancerous situations, modulation of the Th1/Th2, Th3 cell balance may be in the direction of inducing a pro-inflammatory response or in augmenting the anti-tumor associated antigens immunity. As used herein to describe the present invention, "cancer", "tumor" and "malignancy" all relate equivalently to a hyperplasia of a tissue or organ. If the tissue is a part of the lymphatic or immune systems, malignant cells may include non-solid tumors of circulating cells. Malignancies of other tissues or organs may produce solid tumors. In general, the compositions of the present invention may be used in the treatment of non-solid and solid tumors.

Malignancy, as contemplated in the present invention may be selected from the group consisting of carcinomas, melanomas, lymphomas, myeloma, leukemia and sarcomas. Malignancies that may find utility in the present invention can comprise but are not limited to hematological malignancies (including leukemia, lymphoma and myeloproliferative disorders), hypoplastic and aplastic anemia (both virally induced and idiopathic), myelodysplastic syndromes all types of paraneoplastic syndromes (both immune mediated and idiopathic) and solid tumors (including lung, liver, breast, colon, prostate GI tract, pancreas and Karposi). More particularly, the malignant disorder may be hepatocellular carcinoma, colon cancer, melanoma, myeloma, acute or chronic leukemia.

It should be noted that the immuno-modulatory composition of the invention may be applicable for treating infectious diseases caused by bacterial infections, viral infections, fungal infections, or parasitic infections. More specifically, the viral infection may be caused by any one of HBV, HCV or HIV.

According to a specific embodiment, the composition of the invention is particularly suitable for oral or mucosal administration.

The usefulness of an oral formulation requires that the active agent or combinations of the invention be bio-available.

Bioavailability of orally administered drugs can be affected by a number of factors, such as drug absorption throughout the gastrointestinal tract, stability of the drug in the gastrointestinal tract, and the first pass effect. Thus, effective oral delivery of an active agent or combination requires that the active agent have sufficient stability in the stomach and intestinal lumen to pass through the intestinal wall. Many drugs, however, tend to degrade quickly in the intestinal tract or have poor absorption in the intestinal tract so that oral administration is not an effective method for administering the drug.

More specifically, the composition of the invention may be suitable for mucosal administration, for example, pulmonary, buccal, nasal, intranasal, sublingual, rectal, vaginal administration and any combination thereof.

Although preferred administration is oral or mucosal, it should be appreciated that the composition of the invention may be also suitable for intravenous, intramuscular, subcutaneous, intraperitoneal, parenteral, transdermal, sublingual, topical, administration, or any combination thereof.

In another aspect, the invention further relates to an oral or mucosal pharmaceutical composition made by combining a therapeutically effective amount of at least one natural or synthetic beta-glycolipid and at least one immunoglobulin molecule specific for an epitope derived from a component of the immune system or any functional fragments thereof, and optionally at least one additional therapeutic agent, with a pharmaceutically acceptable carrier.

According to a specifically preferred embodiment, such composition is as described by the invention.

Pharmaceutical compositions suitable for oral administration are typically solid dosage forms (e.g., tablets) or liquid preparations (e.g., solutions, suspensions, or elixirs).

Solid dosage forms are desirable for ease of determining and administering dosage of active ingredient, and ease of administration, particularly administration by the subject at home.

Liquid dosage forms also allow subjects to easily take the required dose of active ingredient. Liquid preparations can be prepared as a drink, or to be administered, for example, by a nasal-gastric tube (NG tube). Liquid oral pharmaceutical compositions generally require a suitable solvent or carrier system in which to dissolve or disperse the active agent, thus enabling the composition to be administered to a subject. A suitable solvent system is compatible with the active agent and non-toxic to the subject. Typically, liquid oral formulations use a water-based solvent.

The oral compositions of the invention can also optionally be formulated to reduce or avoid the degradation, decomposition, or deactivation of the active agents by the gastrointestinal system, e.g., by gastric fluid in the stomach. For example, the compositions can optionally be formulated to pass through the stomach unaltered and to dissolve in the intestines, i.e., enteric coated compositions.

As indicated above, the combined beta-glycolipids and antibodies described herein can be incorporated into a pharmaceutical composition suitable for oral or mucosal administration, e.g., by ingestion, inhalation, or absorption, e.g., via nasal, intranasal, pulmonary, buccal, sublingual, rectal, or vaginal administration. Such compositions can include an inert diluent or an edible carrier. For the purpose of oral therapeutic administration, the active compound (e.g., combination of an anti-CD3 antibody and a beta-glucosylceramide (GC) can be incorporated with recipients and used in solid or liquid (including gel) form. Oral compositions can also be prepared using an excipient. Pharmaceutically compatible binding agents, and/or adjuvant materials can be included as part of the composition. Oral dosage forms comprising combined beta-glycolipid and antibody are provided, wherein the dosage forms, upon oral administration, provide a therapeutically effective blood level of the combined beta-glycolipid and antibody to a subject. Also provided are mucosal dosage forms comprising said combination wherein the dosage forms, upon mucosal administration, provide a therapeutically effective blood level of the combined beta-glycolipid and antibody to a subject. For the purpose of mucosal therapeutic administration, the active combined compounds (e.g., beta-glucosylceramide with an anti-CD3 antibody) can be incorporated with excipients or carriers suitable for administration by inhalation or absorption, e.g., via nasal sprays or drops, or rectal or vaginal suppositories.

Solid oral dosage forms include, but are not limited to, tablets (e.g., chewable tablets), capsules, caplets, powders, pellets, granules, powder in a sachet, enteric coated tablets, enteric coated beads, and enteric coated soft gel capsules. Also included are multi-layered tablets, wherein different layers can contain different drugs. Solid dosage forms also include powders, pellets and granules that are encapsulated. The powders, pellets, and granules can be coated, e.g., with a suitable polymer or a conventional coating material to achieve, for example, greater stability in the gastrointestinal tract, or to achieve a desired rate of release.

In addition, a capsule comprising the powder, pellets or granules can be further coated. A tablet or caplet can be scored to facilitate division for ease in adjusting dosage as needed.

The dosage forms of the present invention can be unit dosage forms wherein the dosage form is intended to deliver one therapeutic dose per administration, e.g., one tablet is equal to one dose. Such dosage forms can be prepared by methods of pharmacy well known to those skilled in the art. Typical oral dosage forms can be prepared by combining the active ingredients in an intimate admixture with at least one excipient according to conventional pharmaceutical compounding techniques. Excipients can take a wide variety of forms depending on the form of preparation desired for administration. For example, excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents. Examples of excipients suitable for use in oral liquid dosage forms include, but are not limited to, water, glycols, oils, alcohols, flavoring agents, preservatives, and coloring agents. Tablets and capsules represent convenient pharmaceutical compositions and oral dosage forms, in which case solid excipients are employed. If desired, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

As one example, a tablet can be prepared by compression or by molding. Compressed tablets can be prepared, e.g., by compressing, in a suitable machine, the active ingredients (e.g., combined beta-glycolipid and antibody) in a free-flowing form such as powder or granules, optionally mixed with an excipient. Molded tablets can be made, e.g., by molding, in a suitable machine, a mixture of the powdered combined beta-glycolipid and antibody compound moistened, e.g., with no inert liquid diluent.

Excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gum tragacanth or gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidinones, methyl cellulose, pre-gelatinized starch, hydroxypropyl methyl cellulose, microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions and dosage forms of the invention is typically present in from about 50 to about 99 weight percent of the pharmaceutical composition or dosage form.

Disintegrants can be used in the pharmaceutical compositions and oral or mucosal dosage forms of the invention to provide tablets that disintegrate when exposed to an aqueous environment. Tablets containing too much disintegrant might disintegrate in storage, while those containing too little might not disintegrate at a desired rate or under desired conditions.

Thus, a sufficient amount of disintegrant that is neither too much nor too little to detrimentally alter the release of the active ingredients should be used to form the pharmaceutical compositions and solid oral dosage forms described herein. The amount of disintegrant used varies based upon the type of formulation, and is readily discernible to those of ordinary skill in the art. Typically, pharmaceutical compositions and dosage forms comprise from about 0.5 to about 15 weight percent of disintegrant, preferably from about 1 to about 5 weight percent of disintegrant.

Disintegrants that can be used in pharmaceutical compositions and oral or mucosal dosage forms of the invention include, but are not limited to, agar-agar, alginic acid, calcium carbonate, Primogel, microcrystalline cellulose, croscarmellose sodium, crospovidone, polacrilin potassium, sodium starch glycolate, corn, potato or tapioca starch, other starches, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate or Sterotes, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W. R. Grace Co. of Baltimore, Md.), a coagulated aerosol of synthetic silica (marketed by Degussa Co. of Plano, Tex.), CAB-O-SIL03 (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated. A glidant such as colloidal silicon dioxide can also be used.

The pharmaceutical compositions and oral or mucosal dosage forms can further comprise one or more compounds that reduce the rate by which an active ingredient will decompose. Thus the oral dosage forms described herein can be processed into an immediate release or a sustained release dosage form. Immediate release dosage forms may release the combined beta-glycolipid and antibody in a fairly short time, for example, within a few minutes to within a few hours. Sustained release dosage forms may release the combined beta-glycolipid and antibody over a period of several hours, for example, up to 24 hours or longer, if desired. In either case, the delivery can be controlled to be substantially at a certain predetermined rate over the period of delivery. In some embodiments, the solid oral dosage forms can be coated with a polymeric or other known coating material(s) to achieve, for example, greater stability on the shelf or in the gastrointestinal tract, or to achieve control over drug release. Such coating techniques and materials used therein are well-known in the art. Such compounds, which are referred to herein as "stabilizers," include, but are not limited to, antioxidants such as ascorbic acid and salt buffers. For example, cellulose acetate phthalate, polyvinyl acetate phthalate, hydroxypropylmethyl cellulose phthalate, methacrylic acid-methacrylic acid ester copolymers, cellulose acetate trimellitate, carboxymethylethyl cellulose, and so hydroxypropylmethyl cellulose acetate succinate, among others, can be used to achieve enteric. coating. Mixtures of waxes, shellac, rein, ethyl cellulose, acrylic resins, cellulose acetate, silicone elastomers can be used to achieve sustained release coating.

Liquids for oral or mucosal administration represent another convenient dosage form, in which case a solvent can be employed. In some embodiments, the solvent is a buffered liquid such as phosphate buffered saline (PBS). Liquid oral dosage forms can be prepared by combining the active ingredient in a suitable solvent to form a solution, suspension, syrup, or elixir of the active ingredient in the liquid. The solutions, suspensions, syrups, and elixirs may optionally comprise other additives including, but not limited to, glycerin, sorbitol, propylene glycol, sugars or other sweeteners, flavoring agents, and stabilizers. Flavoring agents can include, but are not limited to peppermint, methyl salicylate, or orange flavoring. Sweeteners can include sugars, aspartame, saccharin, sodium cyclamate and xylitol.

In order to reduce the degree of inactivation of orally administered the combined beta-glycolipid and antibody in the stomach of the treated subject, an antiacid can be administered simultaneously with the immunoglobulin, which neutralizes the otherwise acidic character of the gut.

For administration by inhalation, the mucosal combined beta-glycolipid and antibody compounds can be delivered in the form of an aerosol spray from pressured container or dispenser which contains a suitable propellant, e.g., a gas such as carbon dioxide, or a nebulizer.

Systemic administration can also be by transmucosal means. For transmucosal administration, penetrants appropriate to the barrier to be permeated are used in the formulation. Such penetrants are generally known in the art, and include, for example, for transmucosal administration, detergents, bile salts, and fusidic acid derivatives.

Transmucosal administration can be accomplished through the use of nasal drops or sprays, or rectal or vaginal suppositories.

The combined beta-glycolipid and antibody, specifically, GC and anti-CD3, compounds of the invention can also be prepared in the form of suppositories (e.g., with conventional suppository bases such as cocoa butter and other glycerides) or retention enemas for rectal delivery.

In one embodiment, the oral or mucosal combined beta-glycolipid and antibody compositions are prepared with carriers that will protect the combined beta-glycolipid and antibody against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or may be obtained commercially.

Dosage, toxicity and therapeutic efficacy of such combined beta-glycolipid and antibody compositions can be determined by standard pharmaceutical procedures in cell cultures or experimental animals, e.g., for determining the LD50 (the dose lethal to 50% of the population) and the ED50 (the dose therapeutically effective in 50% of the population). The dose ratio between so toxic and therapeutic effects is the therapeutic index and it can be expressed as the ratio LD50/ED50. Compositions which exhibit high therapeutic indices are preferred.

Data obtained from the cell cultures (e.g., of cells taken from an animal after mucosal administration of the combined beta-glycolipid and antibody) and animal studies can be used in formulating a range of dosage for use in humans. The dosage may vary within this range depending upon the dosage form employed and the route of administration utilized. For any oral or mucosal combined beta-glycolipid and antibody compositions described herein, the therapeutically effective dose can be estimated initially from assays of cell cultures (e.g., of cells taken from an animal after mucosal administration of the combined beta-glycolipid and antibody). A dose may be formulated in animal models to achieve a desired circulating plasma concentration of TGF-β, IL-10, IL-4 or IL-2 and IFN-γ, or of regulatory cells, in the range that includes the $IC_{50}$ (i.e., the concentration of the test compound which achieves a half-maximal inhibition of symptoms) as determined in cell culture. Such information can be used to more accurately determine useful doses in humans.

The combined beta-glycolipid and antibody compositions can be administered from one or more times per day to one or more times per week, including once every other day. The oral or mucosal combined beta-glycolipid and antibody compositions can be administered, e.g., for about 1 to 30, 5 to 14 days or longer. The skilled artisan will appreciate that certain factors may influence the dosage and timing required to effectively treat a subject, including but not limited to the severity of the disease or disorder, previous treatments, the general health and/or age of the subject, and other diseases present.

Moreover, treatment of a subject with a therapeutically effective amount of the combined compounds can include a single treatment or, can include a series of treatments.

As indicated herein, the oral or mucosal combined beta-glycolipid and antibody compositions can also include one or more therapeutic agents useful for treating an immune-related disorder. Such therapeutic agents can include, e.g., NSAIDs (including COX-2 inhibitors); other antibodies, e.g., anti-cytokine antibodies, gold-containing compounds; immunosuppressive drugs (such as corticosteroids, e.g., prednisolone and methyl prednisolone; cyclophosphamide; azathioprine; mycophenolate mofetil (MIVIF); cyclosporin and tacrolimus; methotrexate; or cotrimoxazole) and heat shock proteins.

The pharmaceutical compositions can be included in a container, pack, or dispenser together with instructions for administration.

One of ordinary skill in the art would readily appreciate that the pharmaceutical compositions described herein can be prepared by applying known pharmaceutical manufacturing procedures. Such formulations can be administered to the subject with methods well-known in the pharmaceutical arts. Thus, the practice of the present methods will employ, unless otherwise indicated, conventional techniques of pharmaceutical sciences including pharmaceutical dosage form design, drug development, and pharmacology, as well as of organic chemistry, including polymer chemistry. Accordingly, these techniques are within the capabilities of one of ordinary skill in the art and are explained fully in the literature.

According to a further aspect, the invention relates to a method of treating, preventing, ameliorating or delaying the onset of an immune-related disorder in a subject in need thereof. The method of the invention comprises the step of administering to a treated subject a therapeutically effective amount of at least one of:

(a) a combination of at least one natural or synthetic beta-glycolipid and at least one immunoglobulin molecule specific for an epitope derived from a component of the immune system or any functional fragments thereof;

(b) an immune-cell treated with (a) or with a composition comprising the same;

(c) an immune-cell obtained from a subject treated with any one of (a), (b) or with any combinations thereof or with a composition comprising the same; and (d) a composition comprising any one of (a), (b), (c), or any combination thereof, said composition optionally further comprises at least one pharmaceutically acceptable carrier, diluent, excipient and/or additive.

According to a specifically preferred embodiment, the method of the invention may uses any of the compositions described herein.

According to one embodiment, the beta-glycolipid used by the method of the invention may be selected from the group consisting of a glucosylceramide, a monosaccharide ceramide, a galatosylceremide, a lactosyl-ceramide, a gal-gal-glucosyl-ceramide, GM2 ganglioside, GM3 ganglioside, globoside or any synthetic or natural β-glycolipid or any derivative or combination thereof.

In another embodiment, the immunoglobulin molecule used by the method of the invention may be an antibody specifically recognizing any one of CD3, CD46, CD2, ICOS, CTLA-4, CD28, PD1 and CD94 and anti CD20 or any combination thereof.

According to one specific embodiment, the beta-glycolipid used by the method of the invention may be glucosylceramide (GC) and the immunoglobulin molecule used may be an anti-CD3 antibody.

In yet another embodiment, the immune-cell used by the method of the invention may be any one of APC (antigen presenting cell), T regulatory cell, any other cell associated directly on indirectly with the immune system including but not limited to platelets, macrophages, any type of B cell, T cell (including double negative cells), and any type of non-professional antigen presenting cell, adipocytes, endothelial cell, any type of cell that is part of an organ, specifically, an organ connected to the treated immune-related disorder and any type of cell having regulatory enhancing or suppressing properties. Specifically, these immune-cells are cells treated by a combination of GC and anti-CD3, or obtained from a subject treated with a combination of GC and anti-CD3.

Thus, according to one embodiment, the method of the invention comprises the step of administering a therapeutically effective amount of a combination of GC and an anti-CD3 antibody or of a composition comprising the same to the treated subject.

According to another embodiment, the method of the invention involves the step of administering to a treated subject, a therapeutically effective amount of immune-cells treated or contacted in vitro with a combination of GC and anti-CD3. In yet another embodiment, the method of the invention comprises the step of administering to a treated subject, a therapeutically effective amount of immune-cells obtained from a subject treated with a combination of GC and anti-CD3. Such immune-related cells may be at least one of T regulatory cells, APC and any other cell associated directly on indirectly with the immune system including but not limited to platelets, macrophages, any type of B cell, T cell (including double negative cells), and any type of non-professional antigen presenting cell, adipocytes, endothelial cell, any type of cell that is part of an organ, specifically, an organ connected to the treated immune-related disorder and any type of cell having regulatory enhancing or suppressing properties. More specifically, immune-related cells applicable for the method of the invention may be any T regulatory cell, for example any one of CD4±LAP+ T-reg cells, CD4+CD25 T-reg cells, CD8+ CD25 T-reg cells, FoxP3+CD4 T-reg cells, CD25 High T-reg cells, CD127 MFI T-reg cells, CD28 MFI T-reg cells, CTLA4− T-reg cells and HLA-DR T-reg cells.

According to one specific embodiment, the method of the invention may use CD4+LAP+ T-reg cells.

According to another embodiment, the immune-cells used by the method of the invention may be any APC, particularly, Dendritic Cell (DC). A particular example may be DC expressing TGF-β and LAP, as well as DC expressing one of IL-10, IL-23, IL-1 and IL-6.

In order to obtain APCs, T reg cell or any other immune-cell from a subject, particularly human patients, and blood is drawn from the patient by cytopheresis, a procedure by which a large number of white cells is obtained, while other blood components are being simultaneously returned back to the patient. The APC or any other immune-cells used by the method of the invention may be prepared from these cells and frozen in small aliquots.

Examples 5 and 6 demonstrate the feasibility of using T-regulatory cells and DC, respectively, obtained from a subject treated with the combined composition of the invention, for treating immune-related disorders. In another embodiment, theses cells may be ex vivo educated or contacted with the combined synergistic composition of the invention. The immune-cells, either treated ex vivo or obtained from a treated subject, may be re-introduced to a treated subject. This can be carried out by a process that has been termed adoptive transfer. The particular DC or T reg. cells used for the transfer may preferably originate from the subject (autologous transfer). A syngeneic or non-syngeneic donor (non-autologous transfer) is not excluded. The storage, growth or expansion of the transferred cells may have taken place in vivo, ex vivo or in vitro.

Methods for in vitro storage, growth or expansion of cells prior to transfer are well known to practitioners of the art. When the immune-related cells intended for use in a transfer are derived from a donor, these cells may also undergo storage, growth or expansion in vivo or in vitro as described above.

Cell therapy may be by injection, e.g., intravenously, or by any of the means described herein above. Neither the time nor the mode of administration is a limitation on the present invention. Cell therapy regimens may be readily adjusted taking into account such factors as the possible cytotoxicity of the educated cells, the stage of the disease and the condition of the patient, among other considerations known to those of skill in the art.

More particularly, the immunomodulatory methods of treatment, amelioration or prevention described by the invention typically include administering to a subject an oral or mucosal combined beta-glycolipid and antibody composition sufficient to stimulate the mucosal immune system. In some embodiments, the methods include administering an oral or mucosal combined beta-glycolipid and antibody composition sufficient to increase TGF-β, IL-10 IL-4, IL-5, IL-9 and/or IL-13 (anti-inflammatory) or alternatively, were pro-inflammatory response is required, IL-2 or IFN-γ, IL-17, IL-23 and IL-6 (pro-inflammatory) production by T cells in the peripheral blood, e.g., regulatory T cells, e.g., by about 5%, 10%, 15%, 20%, 25%, 30%, 35%, 40%, 45%, 50%, 55%, 60%, 65%, 70%, 75%, 80%, 85%, 90%, 95%, 100%, 200%, 300%, 500% or more. In some embodiments, the methods include administering an oral combination of GC and anti-CD3 antibody composition sufficient to decrease T cell proliferation in the peripheral blood, e.g., by about 5% to 90%; e.g., in some embodiments, by at least about 5%, 10%, 20%, 30%, 40%, 50%, 60%, 70%, 80%, 90%, or more.

According to one specific embodiment, the composition used by the method of the invention may modulate the Th1/Th2, Th3 cell balance toward an anti-inflammatory Th2 immune response in a subject suffering from an immune-related disorder. Modulation of the Th1/Th2, Th3 balance towards an anti-inflammatory Th2, Tr1/Th3 response may be particularly applicable in immune related disorders having an undesired unbalanced pro-inflammatory Th1 reaction, for example, such immune-related disorders may be an autoimmune disease, graft rejection pathology, inflammatory disease, non alcoholic fatty liver disease, hyperlipidemia, atherosclerosis, Metabolic Syndrome or any of the conditions comprising the same.

Thus, according to one embodiment, the method of the invention leads to a decrease or reduction in the amount or expression of pro-inflammatory cytokines such as IL-2, IL-17, IL-23, IFN-γ, IL-6. In yet another specific embodiment, the composition of the invention elevates, enhances and increases the amount or expression of anti-inflammatory cytokines such as TGF-β, and IL-10, IL-4, IL-5, IL-9 and IL-13.

According to another embodiment, the combined composition used by the method of the invention induces at least one of T regulatory cells or any other type of cell that has regulatory properties where these are suppressive or not in a subject suffering from an immune-related disorder.

Therefore, according to one embodiment, the method of the invention may be applicable for treating an autoimmune disease, for example, Metabolic Syndrome or any of the conditions comprising the same, an autoimmune disease, graft rejection pathology, inflammatory disease, non alcoholic fatty liver disease, hyperlipidemia, rheumatoid arthritis, type I diabetes, artherosclerosis, asthma, acute and chronic graft versus host disease, systemic lupus erythmatosus, scleroderma, multiple sclerosis, inflammatory bowel disease, psoriasis, uvietis, thyroiditis and immune mediated hepatitis.

As shown by the invention, the combined GC+anti-CD3 composition used by the method of the invention leads to at least one of a decrease in the serum levels of cholesterol, triglycerides, ALT, AST and Glucose in a subject suffering of an immune-related disorder. Moreover, the combined composition used by the method of the invention increases serum levels of insulin. Such method may be particularly useful in treating a subject suffering of a metabolic syndrome or any of the conditions comprising the same.

According to another embodiment, the method of the invention further leads to a significant reduction in pancreatic hyperplasia and hepatic fat accumulation.

In yet another embodiment, the method of the invention leads to down-regulation of macrophages and alters foxp3+ regulatory T cells in fat tissue, suppress inflammatory cytokine production by adipocytes and decrease inflammatory cell infiltration to a fat tissue, specifically of a subject suffering of an immune-related disorder.

Therefore, according to another embodiment, the method of the invention is intended for the treatment of Metabolic Syndrome or any of the conditions comprising the same, for example, at least one of dyslipoproteinemia (hypertriglyceridemia, hypercholesterolemia, low HDL-cholesterol), obesity, NIDDM (non-insulin dependent diabetes mellitus), IGT (impaired glucose tolerance), blood coagulability, blood fibrinolysis defects and hypertension.

According to another embodiment, the method of the invention may be used for treating an autoimmune disease such as rheumatoid arthritis, type I diabetes, artherosclerosis, asthma, acute and chronic graft versus host disease, systemic lupus erythmatosus, scleroderma, multiple sclerosis, inflammatory bowel disease, psoriasis, uvietis, thyroiditis and immune mediated hepatitis.

According to an alternative embodiment, the composition used by the method of the invention may modulate the Th1/Th2, Th3 cell balance toward a pro-inflammatory Th1 immune response in a subject suffering from an immune-related disorder. Accordingly, such method may be applicable in immune-related disorder such as a malignant and non-malignant proliferative disorder, infectious disease, genetic disease and neurodegenerative disorders.

According to another specifically preferred embodiment, all compositions used by any of the method of the invention may be suitable for oral or mucosal administration.

By "patient" or "subject in need" it is meant any mammal who may be affected by the above-mentioned conditions, and to whom the treatment and diagnosis methods herein described is desired, including human, bovine, equine, canine, murine and feline subjects. Preferably said patient is a human. Administering of the drug combination to the patient includes both self-administration and administration to the patient by another person.

It should be appreciated that Examples 9 to 14 clearly demonstrate the feasibility of using the methods and compositions of the invention for treating human subjects. Moreover, the methods of the invention provide long-term treatment, for example, treatment that may be effective for at least between about two weeks to three months. Specifically, more than 14, 21, 28, 30, 35, 42, 49, 56, 64, 70, 80, or 90 days.

The term "therapeutically effective amount" is intended to mean that amount of a drug or pharmaceutical agent that will elicit the biological or medical response of a tissue, a system, animal or human that is being sought by a researcher, veterinarian, medical doctor or other clinician.

In another aspect the invention provides the use of a therapeutically effective amount of a combination of at least one natural or synthetic beta-glycolipid and at least one immunoglobulin molecule specific for an epitope derived from a component of the immune system or any functional fragments thereof, in the preparation of a medicament for the treatment of an immune-related disorder.

In yet another embodiment, the invention provides the use of a combination of GC and anti-CD3 for inducing at least one of T regulatory cells and APC in a subject in need thereof.

In a specifically preferred embodiment, the compositions prepared by the use according to the invention are any of the compositions described herein.

Examples 1 to 8 show a clear synergistic effect of combining both GC and anti-CD3 antibody in ameliorating a pathologic disorder and inducing T regulatory cells, adipocytes and APC. The present invention therefore particularly relates to additive and synergistic combinations of at least one beta-glycolipid and at least one immunoglobulin molecule, specifically, antibody, preferably, the specific combination of GC and anti-CD3 antibody, whereby those additive and synergistic combinations are useful in treating subjects suffering from an immune-related disorder, for example, Metabolic Syndrom. The synergistic and additive compositions of the invention may also be used for the treatment of subjects presenting with symptoms or signs of such disorders.

By synergic combination is meant that the effect of both beta-glycolipid and antibody is greater than the sum of the therapeutic effects of administration of any of these compounds separately, as a sole treatment.

The invention further provides a pharmaceutical unit dosage form comprising at least one natural or synthetic beta-glycolipid and at least one immunoglobulin molecule specific for an epitope derived from a component of the immune system or any functional fragments thereof, and a pharmaceutically acceptable carrier or diluent.

The combined compounds of the present invention are generally administered in the form of a pharmaceutical composition comprising both compounds of this invention together with a pharmaceutically acceptable carrier or diluent. Thus, the compounds used by this invention can be administered either individually in a kit or together in any conventional oral or mucosal dosage form.

More particularly, since the present invention relates to the treatment of diseases and conditions with a combination of active ingredients which may be administered separately, the invention also relates as a further aspect, to combining separate pharmaceutical compositions in kit form. The kit includes at least two separate pharmaceutical compositions: beta-glycolipid and antibody.

The kit of the invention comprises (a) at least one natural or synthetic beta-glycolipid or a pharmaceutically acceptable derivative thereof and a pharmaceutically acceptable carrier or diluent in a first unit dosage form; (b) at least one immunoglobulin molecule specific for an epitope derived from a component of the immune system or any functional fragments thereof, and a pharmaceutically acceptable carrier or diluent in a second unit dosage form; and (c) container means for containing said first and second dosage forms.

More specifically, the kit includes container means for containing both separate compositions; such as a divided bottle or a divided foil packet however, the separate compositions may also be contained within a single, undivided container. Typically the kit includes directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

According to one embodiment the kit of the invention is intended for achieving a therapeutic effect in a subject suffering from an immune-related disorder.

Achieving a therapeutic effect is meant for example, where the kit is intended for the treatment of a specific disorder, the therapeutic effect may be for example slowing the progression of the treated condition.

The invention further provides a method of treating, ameliorating, preventing or delaying the onset of an immune-related disorder in a subject in need thereof comprising the step of administering to said subject a therapeutically effective amount of a first and a second unit dosage forms comprised in a kit according to the invention.

It should be appreciated that both components of the kit, the beta-glycolipid in the first dosage form and the antibody in the second dosage form may be administered simultaneously.

Alternatively, said first compound or dosage form and said second compound or dosage form are administered sequentially in either order.

More specifically, the kits described herein can include an oral combined beta-glycolipid and antibody composition or in separate first and second dosage unit forms, as an already prepared liquid oral dosage form ready for administration or, alternatively, can include the combined beta: glycolipid and antibody composition as a solid pharmaceutical composition that can be reconstituted with a solvent to provide a liquid oral dosage form. When the kit includes the combined beta-glycolipid and antibody composition as a solid pharmaceutical composition that can be reconstituted with a solvent to provide a liquid dosage form (e.g., for oral or nasal administration), the kit may optionally include a reconstituting solvent. In this case, the constituting or reconstituting solvent is combined with the active ingredient to provide liquid oral dosage forms of each of the active ingredients or of a combination thereof. Typically, the active ingredients are soluble in so the solvent and forms a solution. The solvent can be, e.g., water, a non-aqueous liquid, or a combination of a non-aqueous component and an aqueous component. Suitable non-aqueous components include, but are not limited to oils, alcohols, such as ethanol, glycerin, and glycols, such as polyethylene glycol and propylene glycol. In some embodiments, the solvent is phosphate buffered saline (PBS).

The invention further provides a method of inducing at least one immune-cell in a subject in need thereof. The method of the invention comprises the step of administering to the treated subject a therapeutically effective amount of at least one of:
(a) a combination of at least one natural or synthetic beta-glycolipid and at least one immunoglobulin molecule specific for an epitope derived from a component of the immune system or any functional fragments thereof;
(b) an immune-cell treated with (a) or with a composition comprising the same;
(c) an immune-cell obtained from a subject treated with any one of (a), (b) or any combination or mixture thereof or with a composition comprising the same; and
(d) a composition comprising any one of (a), (b), (c), or any combination or mixture thereof, said composition optionally further comprises at least one pharmaceutically acceptable carrier, diluent, excipient and/or additive.

According to another embodiment, an immune-related cell may be an APC (such as DC), Treg cell or any other cell associated directly on indirectly with the immune system including but not limited to platelets, macrophages, any type of B cell, T cell (including double negative cells), and any type of non-professional antigen presenting cell, adipocytes, endothelial cell, any type of cell that is part of an organ, specifically, an organ connected to the treated immune-related disorder and any type of cell having regulatory enhancing or suppressing properties.

Unless otherwise defined, all technical and scientific terms used herein have the same meaning as commonly understood by one of ordinary skill in the art to which this invention belongs. Although methods and materials similar or equivalent to those described herein can no be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Disclosed and described, it is to be understood that this invention is not limited to the particular examples, methods steps, and compositions disclosed herein as such methods steps and compositions may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the Examples and claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Experimental Procedures
β-glycolipids
*β-glucosylceramide (also indicated as GluC or GC), [Avanti Polar Lipids (Alabaster, Ala.)].
Antibodies and Reagents
*Anti CD3 antibody: Mice hamster CD3-specific antibody (clone 145-2C11, Bio Express).
*Anti CD3 (clone 145-2C11) for in vitro stimulation was purchased from BD PharMingen.
Anti-CD3 antibodies Hybridoma cells producing the hamster 145-2C11 mAb (IgG anti-mouse CD3 £ chain) were purchased from ATCC. The hybridoma cells were grown in an Integra flask in DMEM medium containing 10% Low Ig FCS; 10% NCTC-109; 1% non-essential amino acids; 1% sodium pyruvate; 1% L-glutamine; 1% antibiotic/antimycotic; 0.2% gentamycin. Flasks were split twice a week and supernatants were collected and sent to Strategic Biosolutions (Newark, Del.) to concentration and purification.
* OKT3 (Orthoclone OKT-3) was purchased from Ortho Biotech Inc. (New Jersey, USA). Antibodies to OKT3 were evaluated on day 30 using the Human Anti-Mouse Antibodies (HAMA)-ELISA kit (MEDAC, Hamburg, Germany).
*Rat anti TGF-β was purchased from BIO X CELL (West Lebanon, N.H.).
*The reagents for FACS staining CD16/CD32 (FcBlock), FITC, PE, or APC-conjugated anti CD4 (L3T4) and PE-conjugated anti CD25 (PC61) were purchased from BD PharMingen.
*Affinity-purified biotinylated goat anti-LAP polyclonal antibody and Strep-Avidin APC was purchased from R&D Systems.
*7-AAD for staining dead cells was purchased from Sigma-Aldrich.
*Purified Hamster IgG (Jackson ImmunoResearch Laboratories) was used as an isotype control (IC).
*The FOXP3-labeling kit was from eBioscience (San Diego, Calif. USA).
For FACS analysis on freshly isolated PBMCs, Alexa Fluor-647 FOXP3 kit was purchased from BioLegend (San Diego, Calif., USA). Affinity-purified biotinylated goat anti-LAP specific polyclonal antibody and compensating control was from R&D Systems (Minneapolis, Minn., USA) and strepavidin—APC was used as secondary reagent for detecting the biotinylated primary antibody (R&D). FITC-conjugated CD4 or CD8, PE-conjugated CD25 and their compensation controls, were from eBioscince (San Diego, Calif., USA). Other markers as APC conjugated CD11 and PE-conjugated CD40, CD80, CD83, CD86 and HLA-DR were also from eBioscience. FITC conjugated Lin1 was purchased from BD BD PharMingen (San Jose, Calif., USA).

Animals

*C57BL/6 (B6) ob/ob male mice, age 8-10 weeks, were purchased from Jackson Laboratory (Bar Harbor, Me., USA).

*B6/ICOS−/− or B6/WT mice were bred and housed in the pathogen-free animal facility at The Harvard Institutes of Medicine according to the animal protocol guidelines of Harvard University.

Mice were administered standard laboratory chow and water ad libitum, and kept in 12-hour light/dark cycles. Animal experiments were carried out according to the guidelines of the Harvard University-Institutional Committee for Care and Use of Laboratory Animals, and with the committee's approval.

Oral Administration and Injections

Mice were fed a total volume of 0.2 ml by gastric intubation with an 18-gauge stainless steel feeding needle (Thomas Scientific). Mice were fed once a day for five consecutive days with either phosphate-buffered saline (PBS), hamster isotype control (IC 5 µg/feeding), anti CD3 antibody (5 ug/feeding), or β-glucosylceramide (GC), 100 µg/feeding (dissolved in ethanol and emulsified in PBS). Mice fed with the combination of anti-CD3 and GC received 5 ug anti-CD3 and 100 ug GC in 0.2 ml PBS. Mice were injected IP with 100 µg anti TGF-β one day before the feeding and than on alternative days another 4 injections, a total of 500 µg.

Flow Cytometry Analysis

Lymphocytes derived from blood, MLN, or spleens were resuspended in FACS buffer (PBS containing 2% BSA). Cells were first incubated with Fc block to exclude the possibility of nonspecific interaction. For CD4 staining cells were incubated with FITC or PE-conjugated antibodies for 30 min on ice. For LAP staining, cells were first stained with biotinylated LAP-specific antibody and then the cells were stained with SAv-APC. Cells were also stained with 7-AAD+ to exclude dead cells in the FL3 channel. NKT cells were identified by alpha-Galceramide loaded tetramers (NIH tetramer core) according to their protocol, and results were compared with the use of PE CD3+ APC NK1.1+ antibodies. Analysis was performed on a FACScan flow cytometer (Becton Dickinson) and calculated with FlowJo software. Cells sorted for adoptive transfer experiments were stained in a similar manner and sorted for CD4+LAP− or CD4+LAP+ using a FACSVantage SE (BD Biosciences). The purity of each population was determined to be 98% by flow cytometric analysis.

Proliferation Assay

Spleen or MLN cells were cultured in triplicate wells ($5 \times 10^5$ cells per well) in serum-free medium X-VIVO 20 (BioWhittaker) with 1 ug/ml soluble anti-CD3 antibody. Proliferation was measured by scintillation counting after pulsing with 1 uCi [$^3$H]thymidine per well (NEN, Boston, Mass., USA) for the last 16 h of a 72 h incubation period. When purified. T-cells ($10 \times 10^4$ cells per well) were checked for proliferation, they were stimulated with 1 ug/ml anti-CD3 in the presence of DCs ($10 \times 10^3$ cells per well) for 72 h and the proliferative response measured as outlined above.

Cytokine Assay by ELISA

For cytokine assays, splenocytes or MLN cells were grown ($10^6$ cells per well) in serum-free medium X-VIVO 20 (BioWhittaker) with 1 ug/ml soluble anti-CD3 antibody. Supernatants were collected after 40 h for IL-2, IL-4, IL6, IL-10, IFN-γ, and IL-17, or after 72 h for TGF-β and quantitative ELISA was performed using paired antibodies and recombinant cytokines obtained from PharMingen according to their recommendations. When purified T-cells ($0.10 \times 10^4$ cells per well) were checked for cytokine secretion, they were stimulated with 1 ug/ml anti-CD3 in the presence of DCs ($10 \times 10^3$ cells per well) for 40 or 72 h and the cytokine content in the supernatant was measured as outlined above. The tissue cytokine profile was determined for gut, liver, and pancreas. Part of the organ was weighed and homogenized on ice with TISSUEMISER (Fisher Scientific) in buffer containing PBS/BSA/TWEEN and protein inhibitor tablets (Roche). For each 100 mg of tissue, 1 ml of buffer was used. The homogenized material was centrifuged at 4° C. for 10-15 minutes at 10,000 RPM. Supernatants were checked by ELISA for IL2, IL-6, IL-10, IL-17, IFN-γ, and TGF-β.

Purification of DCs from MLN and their Cytokine Expression Measured by RT PCR

MLN CD11C+ DCs were isolated by magnetic separation using anti CD11C microbeads (Miltenyi Biotec). Total RNA was isolated from cell pellets using the RNA easy Mini Kit (QIAGEN) and stored at −80° C. First strand cDNA synthesis was performed on 0.5-1 µg of total RNA for each RNA sample using Taqman reverse transcription reagents. The cDNA was amplified using sequence specific primers for IL-10, and TGF-β and real-time PCR mix (Applied Biosystems) in an ABI7500 cycler. The GAPDH gene was used as an endogenous control to normalize for differences in the amount of total RNA in each sample. All values were expressed as a fold increase or decrease relative to the expression of GAPDH.

Histology

The liver, pancreas, and muscle were removed from control or treated mice and placed in 4% formalin followed by paraffin embedding. Five sections were prepared from each organ. The tissues were stained for heamtoxylin eosin and liver sections were additionally stained with oil-red-o. All sections were blindly scored by a pathologist.

Glucose Tolerance Test (GTT)

Glucose tolerance was assessed by oral administration of glucose (1 gram per kilogram body weight). Blood drawn from the tail was measured for glucose at 0', 15', 30', 60', 90', 120' and 180'. Glucose levels were measured with Elite glucose test strips and a glucometer.

Assessment of AST and ALT and Serum Cholesterol

Sera from individual mice were obtained. Serum AST and ALT levels were measured by an automatic analyzer.

Patient Population

Healthy males (≥18 years) not on therapy for medical or other illnesses were enrolled in accordance with the guidelines of the Hebrew University-Hadassah Institutional Committee for Human Clinical Trials, and the approval of the Israel Ministry of Health Committee for Human Trials. Of 35 potential study subjects screened 18 met inclusion and exclusion criteria and were randomized to one of the treatment groups.

Drug Administration

Nine subjects (3/group) were orally administered 0.2 mg, 1.0 mg or 5.0 mg of OKT3 daily for 5 days and immune parameters measured on days 5, 10 and 30 days (FIG. 12). Six subjects (3/group) received 7.5 mg of beta glucosylceramide in combination with 0.2 mg or 1.0 mg of OKT3 and 3 subjects received GC alone. All subjects were treated with 20 mg of Omeprazole (a proton pump inhibitor) during the 5 days of dosing. Dosing occurred in the morning before breakfast at the study site following a 8 hours fast.

Clinical and Laboratory Follow-Up

All patients underwent a full medical history and physical examination, including review of adverse effects on days 1, 5, 10, and 30, along with complete blood counts, differential, electrolytes, liver and kidney function tests, and lipid profile. C-reactive protein and sedimentation rates were also evaluated.

FACS Analysis on Frozen Lymphocytes

Frozen PBMCs were used for sorting different cell populations, surface staining, and proliferation assays, and cytokine measurements. Cell sorting was performed by thawing $20 \times 10 \times 10^6$ PBMCs at room temperature (RT) and washing themed twice in medium at RT in 50-ml tubes in a 10-ml volume at 1,400 rpm. Cells were suspended to $20 \times 10^6$/ml and stained with seven colors staining of cells using Fc block, Lin-FITC, CD11c-APC, CD123-PE, CD3-Amcyan, CD4-Alexa700, CD25-PB, and 7-AAD was performed. Compensation controls, including an unstained control, were prepared. All samples were washed with medium and filtered into 15-ml tubes with 2 ml volume each to a total volume of 2 ml. CD4+ effector T cells, CD4+ regulatory T cells, myeloid DCs, and plasmacytoid DCs were sorted. Tubes were washed to get retrieve all sticky cells and spin them at 1,400 rpm. All cell populations were put in 350 μl of RLT 350 ul (lysis buffer), and transferred to eppendorff microtubes, and froze at −70° C. RNA was prepared using Qiagen micro kits (Valencia, Calif., USA) and cDNA was prepared using Applied Biosystems kits (Foster City, Calif., USA). We performed real-time PCR (RT-PCR) for different genes on in regulatory T cells, effector T cells, and DCs was performed.

For surface staining, one tube of frozen PBMCs was thawed at room temperature (RT) and washed twice in medium at RT in 50-ml tubes (10-ml volume) at 1,400 rpm. Cells were re-suspended cells at $8\text{-}10 \times 10^6$ cells/ml and 100 μl was aliquoted into each of 100 ul in 11 wells. For LAP+ cells (two wells), controls wells were preincubated with rLAP for 20 mins, and seven-colors staining of cells using CD3-Amcyan, CD4-Alexa700, CD8-APC, CD25-PB, and LAP-PE for 40 mins was preformed for 40 minutes. Cells were washed and stained with Annexin FITC and 7-AAD in Annexing binding buffer for 15 minutes. Cells were washed and analyzed immediately in Annexin Binding Buffer.

For Foxp3 surface staining (two wells), surface six-colors staining of cells using CD3-Amcyan, CD4-Alexa700, CD8-APC, and CD25-PB were performed for 30 minutes. Intracellular staining for IC/Foxp3-PE from eBiosciences was followed. For all other surface markers (7wellsseven wells), seven—color staining of cells was performed, using CD3-Amcyan, CD4-Alexa700, CD8-APC, CD25-PB, and Annexin FITC, 7-AAD, and IC/CD62L/CD69/CD45RO/CD127/CD28/HLA-DR-PE was performed. Cells were then washed Wash twice and Fix fixed the cells with 0.1% paraformaldehyde. Compensation controls, including an unstained control, were prepared. (Lin-FITC, CD11c-APC, CD123-PE, and CD3-Amcyan were tested in 1 μl/100 μl; CD4-Alexa700, CD25-PB, and 7-AAD were tested in 0.5 ul/100 μl; and LAP-PE, and Annexin-FITC were tested in 3 ul/100 μl).

For surface staining, freshly isolated PBMCs were suspended at $8\text{-}10 \times 10^6$ cells/ml. Surface two to three colors staining of cells were done with the following surface antibodies: CD4-FITC/CD25-PE, CD8– FITC/CD25-PE, CD3-APC/CD69-PE, CD11c-APC/Lin-FITC/CD86-PE, CD11c-APC/Lin-FITC/CD83-PE, CD11c-APC/Lin-FITC/HLAdr-PE. For LAP staining cells were preincubated with rLAP/control antibody for 20 mins, and stained with CD4-FITC and CD25-PE or CD8-FITC. For Foxp3 surface staining, surface two-colors staining of cells using CD4-FITC and CD25-PE was performed, followed by intracellular staining with IC/Foxp3-Alexa 647-APC.

Proliferation and Cytokine Assays

PBMCs were isolated from blood samples using Ficol Hypaque solution. To measure proliferation, $2 \times 10^5$ cells per well were cultured in triplicate in RPMI 1640 medium with 5% FBS (Biological Industries, Israel), 100 units/ml penicillin, 100 □g/ml streptomycin, 1% Glutamine, 1% non essential fatty acids, 1% sodium pyruvate and β-mercaptoethanol (Biological Industries, Israel). Cells were stimulated with pre-coated antibodies (in 200 μl PBS/well):μg/well of anti OKT-3 mAb (Ortho Biotech Inc, New Jersey, USA) or 5 μg/ml soluble anti-CD3 mAb (eBioscience, CA, USA) or 2.5 μg/ml anti-CD28 mAb (R&D systems, MN, USA). One set of the above wells were added nothing while 10 μg of GC was added to a similar set for 72 h in culture at 37° C. with 5% CO2. Supernatants were collected for IL-13, IL-17 and IFN-γ. Enzyme-linked immunosorbent assays for these cytokines were performed according to the manufacturer's protocol (R&D Systems, Minneapolis, Minn.). For TGF-β, $2 \times 10^5$ cells per well were cultured in serum free media (Biotarget, Biological Industries, Israel). After collecting the supernatants, 1 □Ci [$^3$H]thymidine (Amersham Biosciences, UK) was added to each well, and cells were harvested 18 h later. Proliferation was measured by scintillation counting.

Expression of Cytokines by Dendritic Cells

RT RT-PCR was performed on DC from all patients in all groups. Sorting of DC was performed as described above. Total RNA was isolated from cell pellets using the RNA easy Mini Kit (QIAGENQiagen). RNA was stored at −80° C. First, strand cDNA synthesis was performed for each RNA sample from 0.5-1 μgm of total RNA using Taqman reverse transcription reagents (Applied Biosystems). cDNA was amplified using sequence-specific primers (for IL-23, IL-10, IL-1, IL-6, and TGF-β) and real-time PCR mix (Applied Biosystems) on an ABI7500 cycler. The GAPDH gene was used as an endogenous control to normalize for differences in the amount of total. RNA in each sample. All values were expressed as fold fold-increase or -decrease relative to the expression of GAPDH.

Antigen Arrays

A panel of self and non-self proteins, peptides and lipids were spotted onto Epoxi slides (TeleChem, CA, USA) as described [Quintana, F. J. et al. Proc. Natl. Acad. Sci. USA 101 Suppl 2:14615-14621 (2004)]. Since several of the self-antigens included in the antigen microarrays used by the invention, are targeted by natural antibodies [Coutinho, A. et al. Curr. Opin. Immunol. 7:812-818 (1995); Quintana, F. J. and Cohen, I. R. Biomed Pharmacother 58:276-281 (2004)], the inventors could detect both the up and the down-regulation of preexisting IgG and IgM reactivities. Sera from OKT3-treated subjects were assayed at a 1/10 dilution and the IgG or IgM reactivities displaying significant changes upon treatment were identified. Briefly, antigens were spotted in replicates of 6, the microarrays were blocked for 1 h at 37° C. with 1% bovine serum albumin, and incubated for 2 hr at 37° C. with a 1:200 dilution of the test serum in blocking buffer. The arrays were then washed and incubated for 45 minutes at 37° C. with a 1:500 dilution of detection antibodies: a goat anti-mouse IgG Cy3-conjugated antibody or a goat anti-mouse IgM Cy5-conjugated antibody (Jackson ImmunoResearch, West Grove, Pa.). The arrays were scanned with a ScanArray 4000x scanner (GSI Luminomics, Billerica, Mass., USA) and the IgM and IgG results were recorded separately.

Raw data were normalized and analyzed using the GeneSpring software (Silicon Genetics, Redwood City, Calif.). Antigen reactivity was defined by the mean intensity of binding to the replicates of that antigen on the microarray. The data were analyzed with the Wilcoxon rank-sum test, a non-parametric test robust to outliers, using the Benjamini and Hochberg false discovery method with a p-value of 0.2 to determine significance [Stekel, D. Microarray Bioinformatics. Cambridge University Press, Cambridge (2003)]. To perform the hierarchical clustering of the antibody reactivities a pair wise average linkage algorithm based on Pearson's correlation was used as a distance measure [Stekel (2003) ibid.]

Statistical Analysis

Statistical significance was assessed by the two-tailed Student's t-test. When there were more than two groups compared, differences were analyzed using one-way ANOVA. P-values <0.05 were considered significant.

Example 1

Significant Synergistic Effect of Orally Administered Combination of Anti-CD3 Antibody and β-Glucosylceramide (GC) on Metabolic Syndrome Model In order to investigate the potential effect of combining two different immune-modulatory compounds on an immune-related disorder such as the metabolic syndrome, the ob/ob leptin deficient mice that manifest insulin resistance, hypelipidemia, fatty liver, and diabetes, were used as an animal model.

Four groups of ob/ob mice were tested, groups 1 and 2 served as control groups (group of untreated mice and group of mice treated with GC and Isotype Control, respectively), group 3 were treated with anti CD3 (5 microgram) antibody and group 4 were orally administered with a combination of anti-CD3 (5 μg) antibody and β-glucosylceramide (GC, 100 μg) per dose for five consecutive days. Animals were assessed on days 10 and 28. The doses studied were based on previous studies of anti-CD3 and GC in animal models [Ochi, H., et al. Nat. Med. 12:627-635 (2006); Zigmond, E. et al. Gut 56:82-89 (2007); Ilan, Y. et al. Transplantation 83:458-467 (2007)]. Determination of hepatic fat content and inflammation was performed by measurement of serum Alanine aminotransferase (ALT) and Aspartate aminotransferase (AST) levels. Serum glucose and cholesterol levels were also assessed.

Figure 1A:
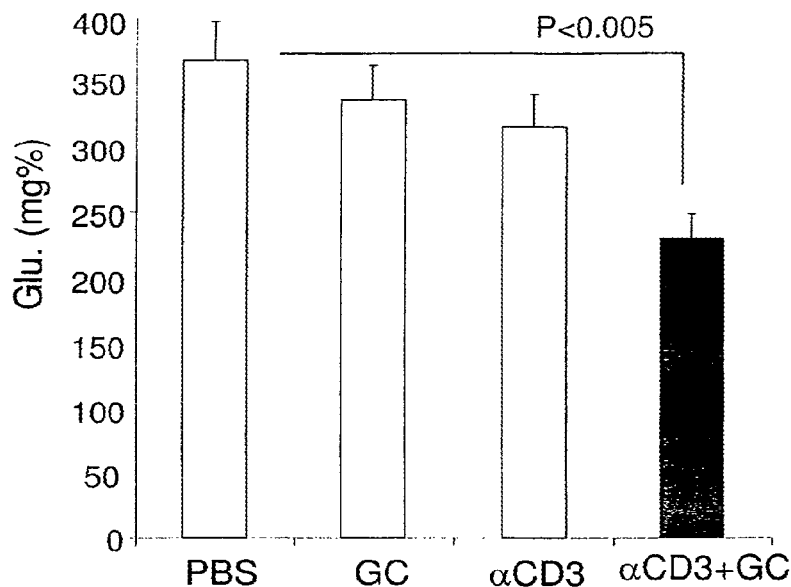
FIG. 1A-1B. Oral combination of anti-CD3 plus GC decreases glucose and liver enzymes in ob/ob mice Ob/ob mice were fed daily for 5 days with either 0.2 ml PBS or 100 ug GC in 0.2 ml PBS or 5 ug anti-CD3 in 0.2 ml PBS or a combination of 5 μg anti-CD3 plus 100 μg GC in 0.2 ml PBS. Mice were tested 10 days after the last feeding for serum glucose (FIG. 1A) and AST (FIG. 1B) levels. n=8/group; representative of 3 individual experiments. Abbreviations: Glu. (glucose).
Figure 1B:
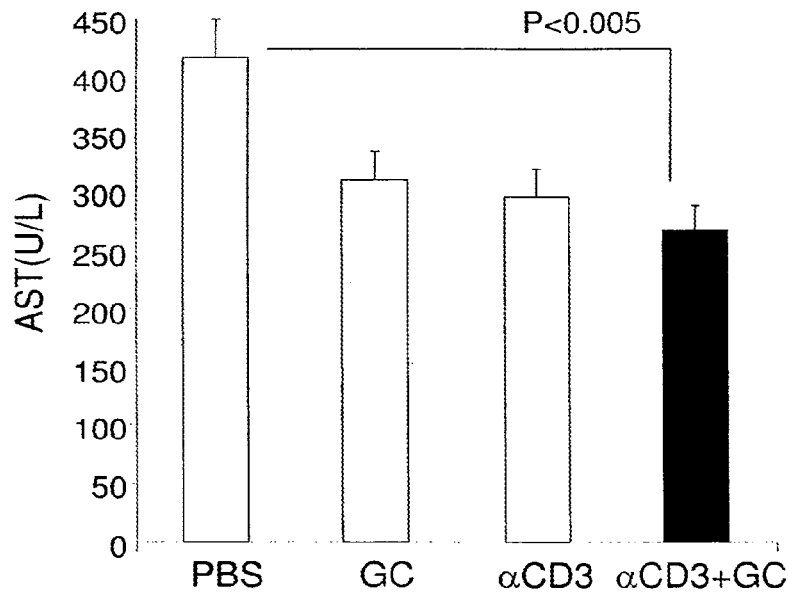

As shown in FIG. 1A, a significant decrease in blood glucose was observed in animals treated with the combined composition of anti-CD3 plus GC (230 mg %) compared to animals fed PBS (367 mg %), GC (337 mg %) or anti-CD3 (316 mg %). In addition, serum AST levels were decreased in animals treated with anti-CD3 plus GC (267 U/l) compared to PBS fed animals (416 U/l), p<0.005 (FIG. 1B). Anti-CD3 (296 U/l) or GC alone (310 U/l) also reduced serum AST vs. PBS (p<0.005) and were not significantly different from anti-CD3 plus GC. Similar effects were observed with serum ALT (not shown). Serum cholesterol levels measured were lower in mice fed anti-CD3 plus GC (208 mg %) vs. PBS (218 mg %), GC (225 mg %), or anti-CD3 (219 mg %), p<0.005. These effects were also observed 28 days post treatment (not shown). No change in the weight of animals was observed in the anti-CD3 plus GC, anti-CD3 or GC groups compared to control.

Figure 2A:
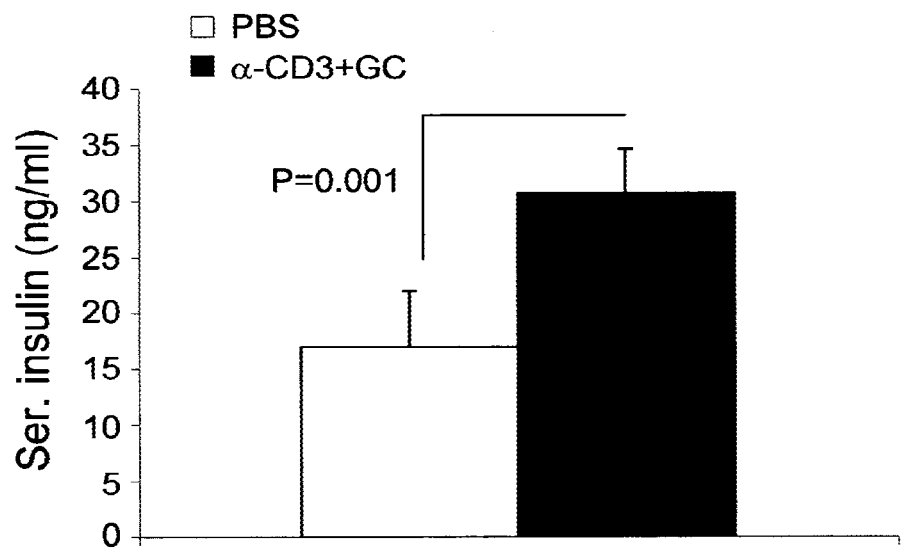
FIG. 2A-2B. Oral anti-CD3 and GC increases insulin production and glucose metabolism in OB/OB mice FIG. 2A. shows serum insulin levels of mice treated with PBS (clear bar) or the combination of anti-CD3 (5 μg) plus GC (100 μg).
Figure 2B:
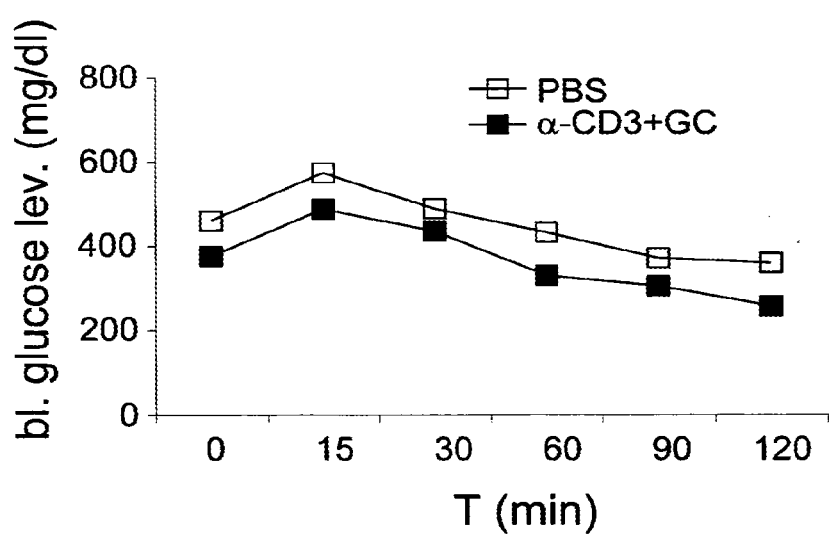

In a further experiment the effect of the combined composition of the invention on insulin serum levels was examined. Therefore, mice (six per group) were fed with 200 μl PBS or with the oral combination of anti-CD3 (5 μg) plus GC (100 μg) solution for 5 consecutive days. Seventy two hours after the last feeding, mouse serum was obtained and diluted 1/50 before used in capture ELISA for insulin. In a parallel experiment, mice (six per group) were deprived of food for 12 hrs prior to GTT. Mice were injected with 2.5 μl/g body weight dextrose solution IP and blood glucose levels were measured at different times using a glucometer. These experiments were repeated 3 times with similar results. As shown by FIG. 2A, treatment with oral combination of anti-CD3 and GC clearly increases insulin production and glucose metabolism (FIG. 2B) in ob/ob mice.

These results clearly indicate that the oral administration of a combination of anti-CD3 antibody with beta glyucosylceramide had a synergistic effect on the alleviation of metabolic syndrome, specifically compared to the effect of each of the compounds alone. This beneficial effect was manifested by reduction of glucose levels, alleviation of accumulation of fat in the liver, reduction in liver enzymes, and on reduction of cholesterol levels. The use of this model illustrates that oral administration of β glycolipid combined with antibodies holds promise as a therapeutic modality for NAFLD and the metabolic syndrome.

Example 2

Figure 3A:
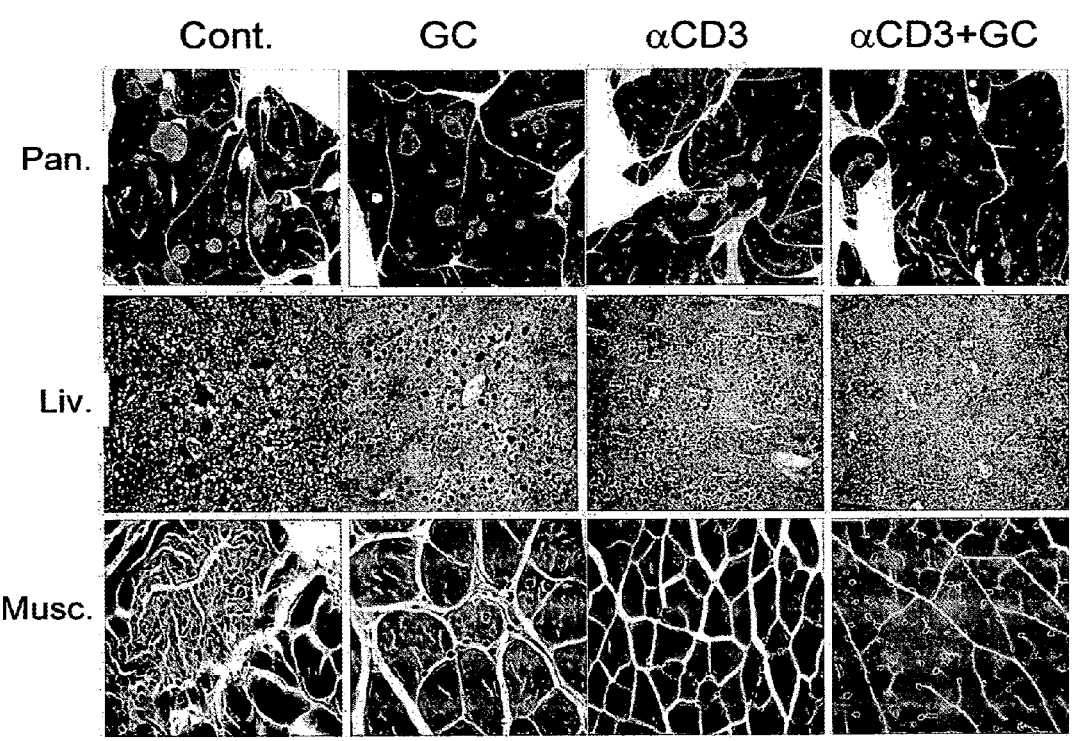
FIG. 3A-3C. Oral combination of anti-CD3 plus GC reduces hepatic fat accumulation and pancreatic hyperplasia FIG. 3A. shows H&E stain of pancreas and muscle and oil red 0 stain of liver from ob/ob mice treated as described in FIG. 1 (10× magnification).
Figure 3B:
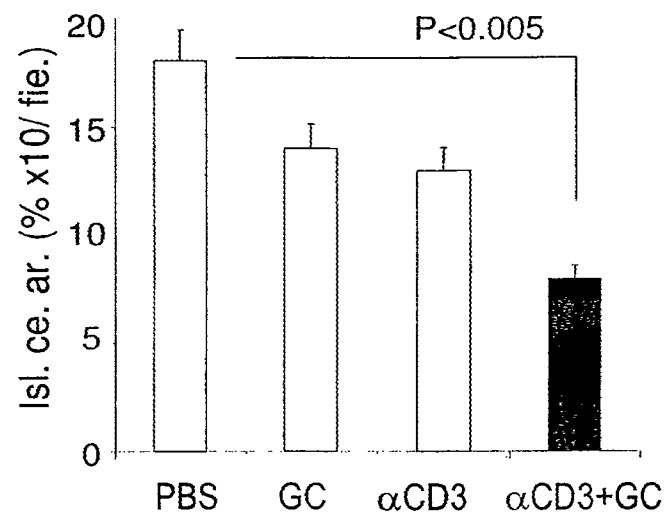
Figure 3C:
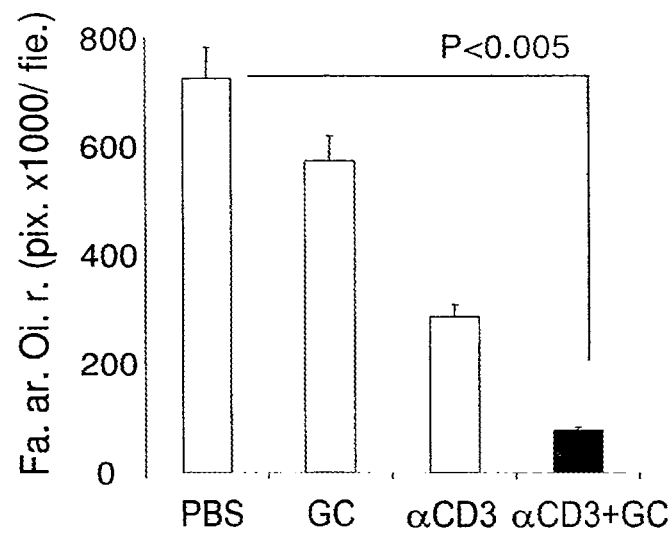

Oral Combined Composition of Anti-CD3 Plus GC Reduces Hepatic Fat Accumulation and Pancreatic Hyperplasia The inventors next investigated the beneficial effect of the combined oral composition of anti-CD3 plus GC treatment of ob/ob mice by pathologic analysis of pancreas, liver and muscle. As shown in FIG. 3, animals fed with the anti-CD3 plus GC combination demonstrated a significant reduction in pancreatic hyperplasia (p<0.005 vs. PBS) and hepatic fat accumulation (p<0.005 vs. PBS). The anti-CD3 plus GC combination was significantly much more effective than anti-CD3 or GC alone, although some effect was observed when the compounds given individually. In addition, a reversal of muscle fiber thinning and increased nuclei was clearly observed in animals treated with the oral combination of anti-CD3 plus GC.

Example 3

Oral Combination of Anti-CD3 Plus GC Enhances Production of TGF-β and IL-10 in the Mesenteric Lymph Node (MLN)

To investigate the potential mechanisms by which oral combination of anti-CD3 plus GC affected the metabolic abnormalities describe above, the inventors next measured cytokine production by MLN cells obtained from the different experimental groups, that were then stimulated in vitro with 1 μg/ml anti-CD3 for five days. As shown in FIGS. 4A and 4B, a marked increase in the production of both TGF-β and IL-10, respectively, was found in MLN cells obtained from animals treated with the anti-CD3 plus GC combination (P<0.005 vs. PBS). No effects were observed with anti-CD3 or GC given alone. Oral combination of anti-CD3 plus GC also decreased IL-2 (P<0.005) and IFN-γ secretion (P<0.005) vs. PBS fed animals (FIGS. 4C and 4D, respectively). A similar increase of TGF-β and IL-10 was also observed in splenocytes (not shown). The inventors next measured cytokine levels in supernatants from homogenized tissues from ob/ob treated mice. As shown by FIGS. 4E and 4F, a significant increase of TGF-β was found in the pancreas and of IL-10 in the gut of the combination of anti-CD3 plus GC treated mice (p<0.005 vs. PBS), respectively. An increase in TGF-β in response to treatment with a combination of anti-CD3 plus GC (890 pg/ml) vs. PBS (720 pg/ml), p<0.005, was also found in the liver. It should be noted that the inventors did not observe an increase of in IL-10 in the pancreas or of TGF-β in the gut.

Example 4

Oral Anti-CD3 Plus GC Increases CD4+LAP-F Cells and Decreases NKT Cells

As previously reported by part of the inventors, oral anti-CD3 increases the number of latency-associated peptide (LAP+) T cells [Ishikawa, H., et at Diabetes 56:2103-2109 (2007); Ochi, H., et al. Nat Med 12:627-635 (2006)]. Latency-associated peptide is the amino-terminal domain of the TGF-β precursor peptide and remains non-covalently associated with the TGF-β peptide after cleavage, forming the latent TGF-β complex [Hyytiainen, M. et al. J. Critical reviews in clinical laboratory sciences 41:233-264 (2004); Lawrence, D. A. Molecular and cellular biochemistry 219: 163-170 (2001); Oklu, R. and Hesketh, R. The Biochemical journal 352 Pt 3:601-610 (2000); Khalil, N. Microbes and infection/Institut. Pasteur 1: 1255-1263 (1999)].

The inventors thus examined whether oral combination of anti-CD3 plus GC may also be associated with an increased CD4+LAP+ cells in lymphoid tissue. As shown in FIG. 5, the percentage of CD4+LAP+ lymphocytes increased in MLN, spleen and blood (FIGS. 5A, 5B and 5C, respectively) measured five days after the last feeding of the combination of anti-CD3 plus GC (P<0.005 vs. PBS). The inventors then measured NKT cells and found a decrease of NKT cells in MLN, spleen and blood of anti-CD3 plus GC fed animals (P<0.005 vs. PBS). No increase of Foxp3 expression was found in T cells following oral anti-CD3 plus GC (not shown).

Example 5

Figures 6A, 6B:
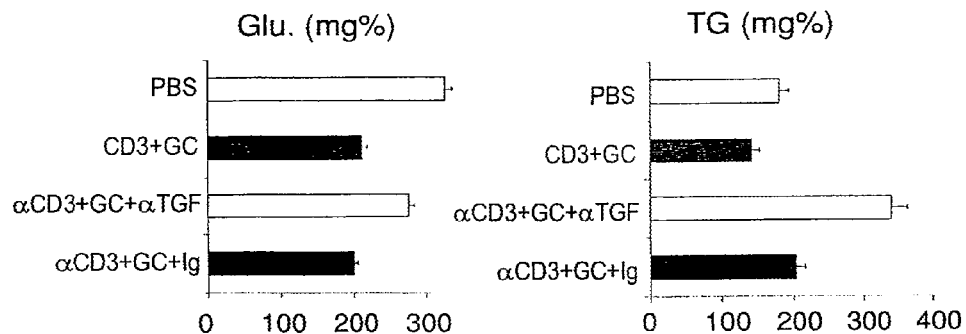
Figures 6C, 6D:
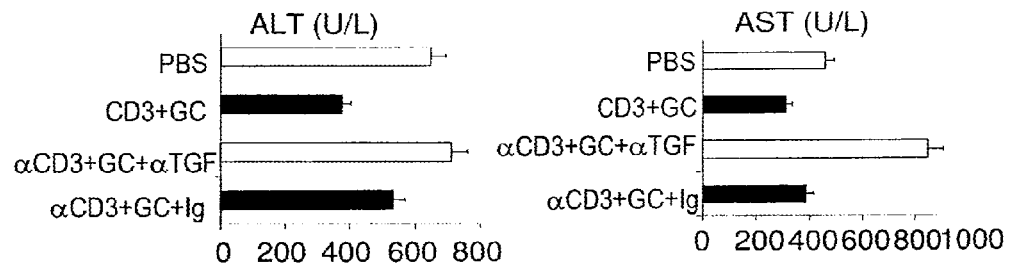
Figures 6E, 6F:
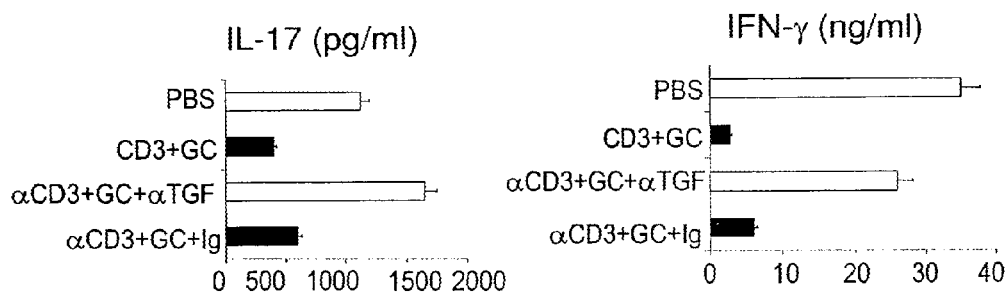
Figure 6G:
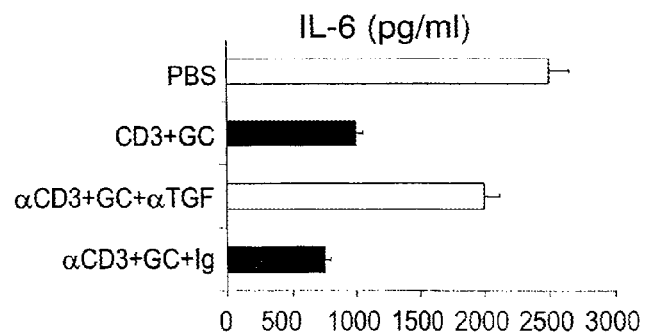

Adoptive Transfer of CD4+LAP+ T Cells Ameliorates Metabolic Abnormalities and Decreases IL-17, IFN-γ and IL-6 in Ob/Ob Mice in a TGF-β Dependent Fashion To investigate the role of LAP+ cells following oral combination of anti-CD3 plus GC, the inventors next adoptively transferred sorted CD4+LAP+ and CD4+LAP− cells harvested from ob/ob donors fed with the oral combination anti-CD3 plus GC to naive ob/ob recipients. As shown in FIG. 6A, adoptive transfer of 4×10$^5$ LAP+ cells obtained from C57/Bl donors fed with the combination of anti-CD3 plus GC, resulted in a 49% decrease of serum glucose levels in ob/ob recipients (from 412 mg % to 212 mg % P<0.005). This effect was reversed in animals treated with anti-TFG-β antibody (p<0.005), but not in animals fed with the control Ig. In addition to measuring blood glucose, other metabolic indicators measured, including triglycerides, ALT, and AST, showed identical results (FIGS. 6A, 6B, 6C and 6D, respectively). The inventors then measured the effect of adoptive transfer on the inflammatory cytokines IL-17, IFN-γ and IL-6. As clearly shown in FIGS. 6E, 6F and 6G, as with the metabolic parameters measured, adoptive transfer of CD4+ LAP+ cells significantly decreased the levels of these inflammatory cytokines in a TGF-β dependent fashion (p<0.005). No effect was observed following adoptive transfer of LAP-cells.

Example 6

Figure 7A:
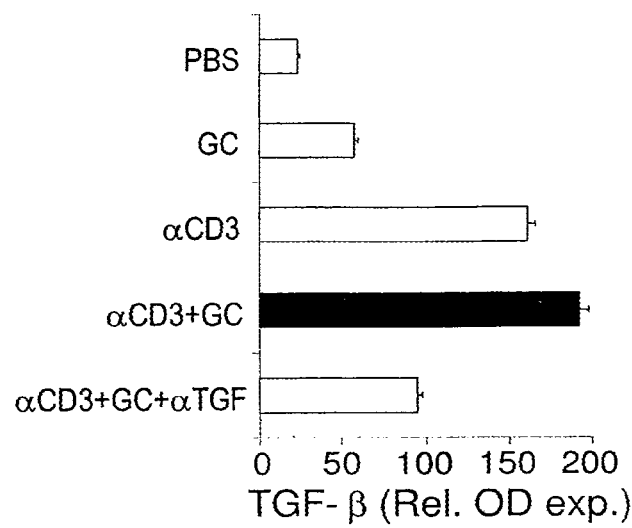
Figure 7B:
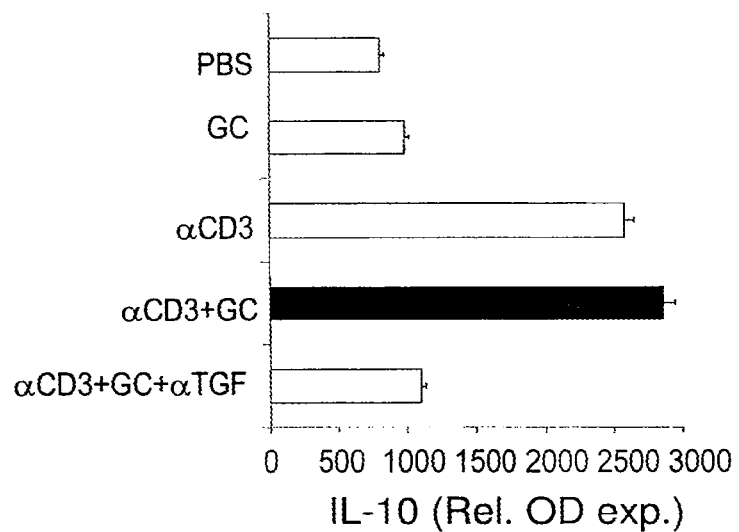
Figure 7C:
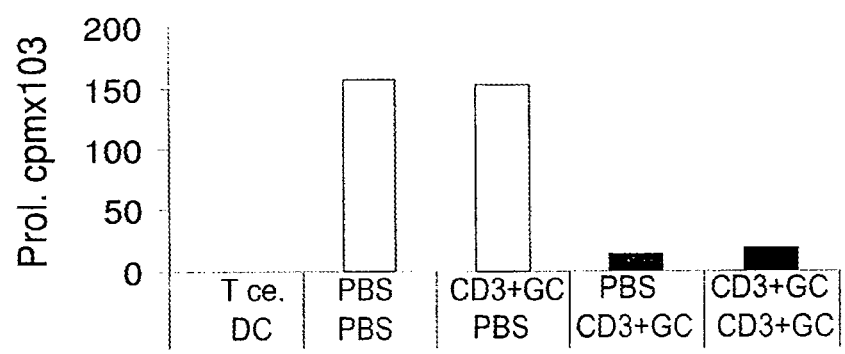
Figure 7D:
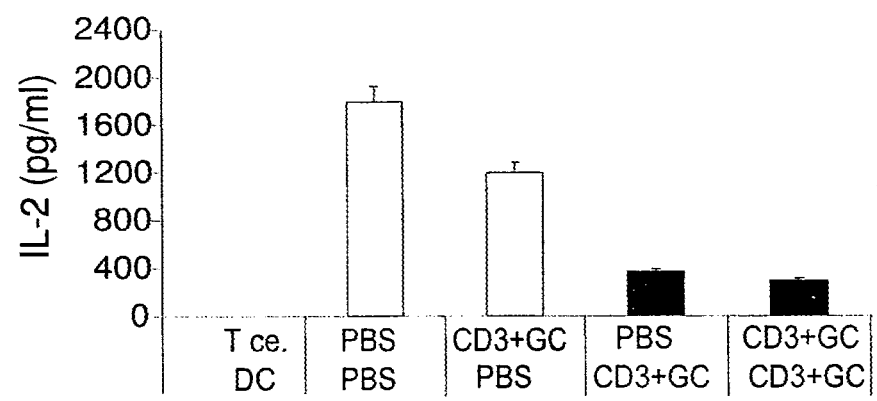
Figure 7E:
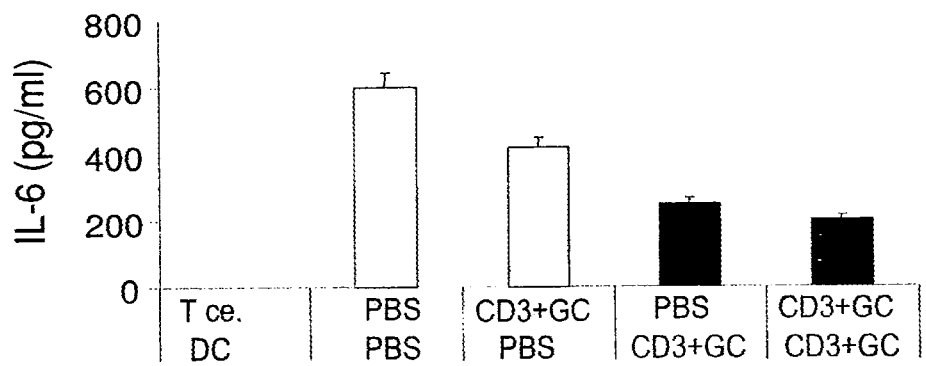
Figure 7F:
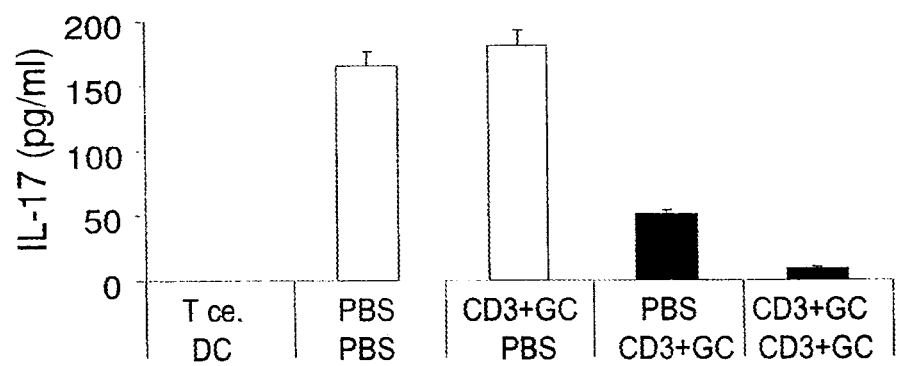

Dendritic Cells from MLN of Ob/Ob Mice Fed with the Combination of Anti-CD3 Plus GC Increased Expression of TGF-β and IL-10 and Suppress IL-2, IL-6, and IL-17 Secretion To investigate the effect of feeding the anti-CD3 plus GC combination on DCs, the inventors first measured the expression of TGF-β and IL-10 in DCs from MLN. As shown in FIGS. 7A and 7B, there was a significant increase of both TGF-β and IL-10 as measured by RT PCR (P<0.005) in animals fed with the anti-CD3 plus GC combination. Analogous effects were seen with oral anti-CD3 alone, but not with GC alone. Injection of anti-TGF-β reversed the effect. The inventors then investigated the effect of DCs obtained from animals treated with the oral combination of anti-CD3 plus GC, or from the control PBS treated animals, on T-cells harvested from mice fed either with PBS or with the combination of anti-CD3 plus GC. T cells were stimulated with anti-CD3 in vitro. As shown in FIGS. 7C-7F, DCs from mice fed with anti-CD3 plus GC decreased the proliferative response as well as IL-2, IL-6 and IL-17 secretion of CD4 T cells irrespective of whether the T cells were obtained from animals fed with PBS or with the anti-CD3 plus GC combination.

Example 7

Increased Secretion of TGF-β and IL-10 by T Cells Following Oral Combination of Anti-CD3 Plus GC is ICOS Dependent It has recently been shown that ICOSL is expressed on DCs taken from bronchial lymph nodes, following nasal administration of ovalbumin (OVA), and that induction of T cell tolerance by DCs is ICOS-dependent [Akbari, O. et al. Nat. Med. 8:1024-1032 (2002); Miyamoto, K. et al. J. Immunol. 175:7341-7347 (2005)]. Given the observation that there is an increased expression of ICOS on T cells following oral antigen administration [Akbari (2002) ibid.; Miyamoto (2005) ibid.], the inventors hypothesized that ICOSL expression on gut DCs may be important in the induction of Tregs that are TGF-β dependent such as LAP+ cells. ICOS−/− mice and wild-type (WT) littermates were fed with the oral combination of anti-CD3 plus GC, and the TGF-β and IL-10 secretion by splenocytes has been measured. As shown in FIG. 8, there was no increase of TGF-β or IL-10 in ICOS −/− animals whereas an increase was observed in wt animals.

Example 8

Oral Combination of CG and Anti-CD3 Down-Regulates Macrophages and Induce Foxp3+Regulatory T Cells, Suppress Inflammatory Cytokine Production by Adipocytes and Decrease Inflammatory Cell Infiltration to a Fat Tissue The inventors further investigated the effect of the combined composition of the invention on immune-cells of a fat tissue of the ob/ob model mice. Therefore, mice (6/group) were fed 200 µl PBS or the combined anti-CD3 (5 µg) plus GC (100 µg) solution for 5 consecutive days. Seventy two hours after the last feeding white fat near or surrounding mesenteric lymph nodes were collected and centrifuged to separate adipocytes from stromal vascular cells. To identify macrophages in adipocytes, cells were immediately stained with fluorescent antibodies to CD11b and F4/80. Percentage of CD11b+F4/80+ double positive cells in individual mice was analyzed by flow cytometry and averages are presented by FIG. 9. The percentage of regulatory T cells in fat following oral combination of anti-CD3 and GC was also examined. Adipocytes were stained with fluorescent antibodies to CD4 before fixed and permeabilized and stained with antibody to foxp3. These experiments were repeated 3 times with similar results. As clearly shown by FIG. 9, the oral combination of GC and anti-CD3 led to decrease in CD11b+F480+ cells and alters CD4+foxp3 T cells, indicating an inhibitory effect on macrophages and modulation of foxp3+ regulatory T cells.

To examine the effect of the combined composition of the invention on fat tissue of treated subjects, the inventors next examined cytokine production of adipocytes. Mice (4/group) were fed 200 µl PBS or anti-CD3 (5 µg) plus GC (100 µg) combined solution for five consecutive days. Seventy two hours after the last feeding perigonadal white fats were collected and centrifuged to separate adipocytes from stromal vascular cells. RNA was extracted from adipocytes and used in real time RTPCR for relative expressions of cytokines. As shown by FIG. 10A, the combined composition of the invention led to reduction of the production pro-inflammatory cytokines (TNF-α) and a moderate elevation in the production of anti-inflammatory cytokines (TGF-β and IL-10). To examine the effect of immune-related cells treated with the combined composition of the invention on the cytokine production of adipocytes, the inventors used T regulatory cells. Therefore, CD4+ T cells were negatively selected from spleens of PBS (FIG. 10B) or combination of anti-CD3 and GC fed mice seventy two hours after the last feeding. The isolated T cells were then co-cultured with adipocytes from control mice at 1:1 ratio for five days. CD4+ T cells were eliminated from co-culture by positive selection leaving adipocytes for RNA extraction and measurement of cytokine expression by real time RTPCR. As shown by FIGS. 10B and 10C, incubation of adipocytes with T regulatory cells obtained from a subject treated with the combined composition of the invention clearly led to suppression of pro-inflammatory cytokine (TNF-α, IL-1) production and elevation in the production of anti-inflammatory cytokines (TGF-β and IL-10), by the co-cultured adypocytes.

The inventors next examined the effect of the combined composition of the invention in the fat tissue level. Therefore, mice (4/group) were fed 200 µl PBS or the oral combination of anti-CD3 (5 µg) plus GC (100 µg) solution for five consecutive days. Seventy two hours after the last feeding perigonadal white fats were collected and fixed in Bouin's fixative before being embedded in paraffin. Fat paraffin sections were stained with H&E. As shown by FIG. 11, the combined composition of the invention remarkably decreased inflammatory cell infiltration to the fat tissue.

Example 9

Systemic Effects of Oral OKT3 and Effect of Oral OKT3 on Cell Surface CD3, Lymphocyte Count and Proliferation As shown by the previous Examples, β-glucosylceramide given orally enhances the effect of oral anti-CD3 in the ob/ob animal model. Based on these findings, the inventors next investigated the effect of oral anti-CD3 or a combination thereof with β-glucosylceramide in healthy human volunteers to determine whether oral anti-CD3 induced immunologic effects in human subjects and whether it was well tolerated. The treatment was well tolerated by all subjects and no systemic effects were observed at any doses including changes in vital signs (temperature, pulse, blood pressure), and liver, kidney or hematologic measures (complete blood counts including differential), during treatment or follow-up (30 days post treatment).

Unlike what has been reported for treatment with IV anti-CD3 (which is also given at a dose of 5 mg per day for five days), no decrease in the CD3+ lymphocyte counts or modulation of CD3 from the T cell surface was observed. In addition, no subject developed anti-OKT3 (HAMA) antibodies. Therefore, the effect of oral OKT3 on proliferative responses was next examined. Peripheral blood lymphocytes were stimulated in vitro with 5 µg/ml of anti-CD3 antibody prior to treatment and at 5 and 10 days post treatment. FIG. 12 shows proliferative responses in three subjects orally administered with 1.0 mg OKT3 (FIGS. 12A and 12B). An increase in proliferation that peaked at day five was observed in all three subjects. This pattern was also observed in one subject dosed with 0.2 mg (FIG. 12C) and in two subjects dosed with 5 mg (FIG. 12D). An identical pattern was observed when results were calculated as stimulation indices.

Example 10

Oral OKT3 Decreases IFN-γ/IL-17 and Increases TGF-β/IL-13 Secretion

To investigate the effect of oral OKT3 on the cytokine secretion profile of T cells, PBL cells were stimulated with 5 µg anti-CD3 and the secretion of IFN-γ, IL-17, TGF-β and IL-13 was measured. As shown in FIG. 13 for the subjects dosed with 1.0 mg OKT3, a decrease in IFN-γ was observed in three subjects and a decrease of IL-17 in two out of three subjects (FIGS. 13A and 13B, respectively). An opposite pattern was observed for IL-13 and TGF-β (FIG. 13C). More specifically, the inventors observed an increase of IL-13 in three out of three subjects (not shown) and an increase of TGF-β in two out of three subjects. Analogous to what was observed in proliferation, similar, though not as consistent findings were observed in subjects dosed with 0.2 mg and 5.0 mg (not shown). These results demonstrate that oral OKT3 decreases the pro-inflammatory profile and increases the anti-inflammatory profile of T cells in the peripheral blood.

Example 11

Oral OKT3 Increases IL-10/TGF-β and Decreases IL-23 Expression in Dendritic Cells To further investigate the effect of oral OKT3 on the innate immune system, the expression of IL-23, IL-10 and TGF-β in dendritic cells was next measured by rtPCR. As shown in FIG. 14 subjects dosed with 1.0 mg OKT3, demonstrated an increase in IL-10 (two out of three subjects, FIG. 14A), and in TGF-β in one out of three subjects (FIG. 14B). Similar findings were observed in two out of three subjects dosed with 0.2 mg and no effect on dendritic cells was observed in subjects dosed with 5.0 mg (not shown). An opposite pattern was observed for IL-23 in which a decrease in IL-23 in all three subjects dosed with 1.0 mg, was observed (FIG. 14C). These results demonstrate that oral OKT3 affects the anti-inflammatory profile of DCs.

Example 12

Effect of Oral OKT3 on Markers of T Cell Regulatory Markers

The inventors next investigated activation of markers and markers associated with regulation on T cells following oral OKT3 treatment. Regulatory T cells were measured by CD25hi, and effector cells were measured by CD25int/lo markers. As shown by FIG. 15A, an increase in CD4+CD25+ and CD8+CD25+ T cells was demonstrated for the 1.0 mg fed group. It should be noted that IV administration of anti-CD3 mAb to type 1 diabetes subjects induced regulatory CD8+CD25+ T cells [Bisikirska, B. et al. The Journal of clinical investigation 115:2904-2913 (2005)]. A similar pattern for CD8+CD25+ T cells with oral OKT3 was observed in all six subjects dosed with 1.0 or 5.0 mg of OKT3 as well as in two subjects dosed with 0.2 mg (not shown). Measurements of surface makers associated with regulatory T cell function, revealed an increase in both CD25hi Foxp3+ cells and CD25hi CTLA4 cells in subjects given 1.0 mg OKT3 (FIG. 15B FIG. 11C demonstrates also an increase in the expression of TGF-$\beta$ on CD25int/lo T cells.

Example 13

Effect of Oral OKT3 on Antigen Arrays

Antigen microarrays constitute a new tool for studying the immune system in health [Quintana, F. J. and Cohen, I. R. Biomed Pharmacother 58:276-281 (2004); Merbl, Y. et al. Clin. Invest. 117:712-718 (2007); Quintana, F. J. et al. J. Autoimmun. 21:65-75 (2003)] and disease [Goldschmidt, Y. et al. Technical Report MCS03-071-018 (2003); Hueber, W. et al. Arthritis Rheum. 52:2645-2655 (2005)]. The inventors therefore used an antigen microarray containing a broad panel of antigens that included self and non self proteins, heat shock proteins, and infectious agents to investigate the effects of oral OKT3 on the immune repertoire. Both increases and decreases of immunoglobulin reactivities were measured.

FIG. 16A demonstrate that treatment with OKT3 resulted in a dose-dependent change in the T-cell dependent IgG repertoire. Minimal changes were observed at the 0.2 mg dose (only 4 reactivities affected) whereas at 1.0 mg, 37 IgG reactivities were affected and at 5.0 mg, 65 IgG reactivates were affected. At the 1.0 mg dose there was an equal number of downregulated (n=19) as up regulated (n=18) reactivities, whereas at the 5 mg dose more up-regulated reactivates were observed (47 vs. 18). FIG. 16B shows a heatmap of changes in the IgG repertoire following oral administration of 1.0 mg OKT3. No changes occurred in the IgM repertoire.

Example 14

Effect of Oral Administration of GC in Combination with OKT3 on Immune Responses As demonstrated by the present Examples 1 to 8, the invention clearly showed a synergistic effect of oral combination of anti-CD3 plus GC in an animal model of type 2 diabetes. Therefore, in order to test whether such synergistic effect of oral combination of OKT3 plus GC also observed in humans, a combination of 7.5 mg GC with 0.2 mg or 1.0 mg OKT3 was examined. When GC was administered with 1.0 oral OKT3, a similar immune effects to those described above with OKT3 alone, were found, though there was a tendency for more consistent responses when GC was co-administered. This was most prominently observed in the expression of IL-10 and IL-23 in DCs, as shown in FIGS. 17A and 17B, which is in accordance with reports that glycolipids affect the function of DCs [Margalit, M. et al. American journal of physiology 289:G917-925 (2005); Ishikawa, H. et al. Diabetes 56:2103-2109 (2007); Ochi, H. et al. Nature medicine 12:627-635 (2006)].

It should be further noted that similar synergistic anti-inflammatory effect of the combined OKT3+GC composition of the invention was also demonstrated for different T regulatory cells examined, including CD4+CD25 T-reg cells, CD8+CD25 T-reg cells, FoxP3+CD4 T-reg cells, CD25 High T-reg cells, CD127 MFI T-reg cells, CD28 MFI T-reg cells, CTLA4– T-reg cells and HLA-DR T-reg cells (not shown).

The invention claimed is:

1. A method of treating non-alcoholic fatty liver disease in a subject, the method comprising
   selecting a subject who has non-alcoholic fatty liver disease; and
   orally administering to the subject a therapeutically effective amount of a composition, wherein the active ingredients in the composition consist of an anti-CD3 monoclonal antibody, or antigen-binding fragment thereof, and
   glucosylceramide (GC).

2. The method of claim 1, wherein said orally administering said therapeutically effective amount of said composition comprises administering said composition in a therapeutically effective amount to reduce fat accumulation in the liver.

3. The method of claim 1, wherein said orally administering said therapeutically effective amount of said composition comprises administering said composition in a therapeutically effective amount to reduce a level of at least one liver enzyme.

4. The method of claim 1, wherein said therapeutically effective amount is sufficient to decrease at least one of IL-2, IL-17, IL-23, IFN-$\gamma$, IL-6 and to increase at least one of TGF-$\beta$ and IL-10.

5. The method according to claim 1, wherein said therapeutically effective amount is sufficient to modulate a Th1/Th2, Th3 cell balance in the subject.

6. The method according to claim 5, wherein said therapeutically effective amount modulates the Th1/Th2, Th3 cell balance toward an anti-inflammatory Th2, Th1/Th3 immune response in the subject.

* * * * *